United States Patent
Tomiyama et al.

(10) Patent No.: US 6,858,724 B2
(45) Date of Patent: Feb. 22, 2005

(54) NON-MUCIN TYPE SYNTHETIC COMPOUNDS OR ITS CARRIER CONJUGATED COMPOUNDS

(75) Inventors: Hiroshi Tomiyama, Nagano-ken (JP); Naoto Ueyama, Nagano-ken (JP); Masahiro Yanagiya, Nagano-ken (JP); Yasufumi Ohkura, Nagano-ken (JP)

(73) Assignee: Kotobuki Pharmaceutical Co., Ltd., Nagano (JP)

( * ) Notice: Subject to any disclaimer, the term of this patent is extended or adjusted under 35 U.S.C. 154(b) by 130 days.

(21) Appl. No.: 09/925,537

(22) Filed: Aug. 10, 2001

(65) Prior Publication Data

US 2002/0107224 A1 Aug. 8, 2002

(30) Foreign Application Priority Data

Aug. 11, 2000 (JP) ......................... 2000-244567

(51) Int. Cl.$^7$ .............................. C07H 7/02; C07H 5/04; A61K 31/70
(52) U.S. Cl. ........................... 536/53; 536/18.7; 514/23
(58) Field of Search .................... 536/53, 18.7; 514/23, 514/8

(56) References Cited

U.S. PATENT DOCUMENTS 5,977,079 A * 11/1999 Good et al.

OTHER PUBLICATIONS

Cipolla et al. (Tetrahedron Asymmetry (2000), 11(1), 295–303).*
Bioconjugate Chem., 2001, vol. 12(3), pp., 325–328.
J. Chem. Soc. Perkin Trans. 1, 1994, vol. 18, pp. 2647–2655.
J. Org. Chem, 1997, vol. 62(23) pp. 8114–8124.
Organic Letters, 2000, vol. 2(25), pp. 4051–4054.
Tetrahedron: Asymmetry, 2000, vol. 11(1), pp. 295–303.
Chemical Abstracts, Abst. No. 135:44926.
Chemical Abstracts, Abst. No. 122:161118.
Chemical Abstracts, Abst. No. 127:331652.
Chemical Abstracts, Abst. No. 134:101106.
Chemical Abstracts, Abst. No. 133:4858.

* cited by examiner

Primary Examiner—James O. Wilson
Assistant Examiner—Michael C. Henry
(74) Attorney, Agent, or Firm—Sherman & Shalloway

(57) ABSTRACT

The purposes of this invention are preparation of the non-mucin type synthetic compounds-carrier conjugated compounds which are stable against enzymes, and which have the ability of specific reactivity to induce immune response for cancer and HIV.

A compound of the general formula (1),

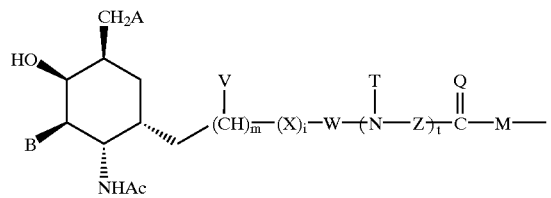

(1)

wherein A represents OH or sialic acid and/or it's derivatives, and B represents OH or galactose and/or it's derivatives; T represents H or protecting groups of amine; M represents H or OH; X represents oxygen atom, —NH— or S(O)z (where z is 0, 1 or 2); Q is H or oxygen atom; V represents lower alkyl or H; W is straight or branched alkylene groups from 0 to 5; Z is straight or branched alkylene groups from 1 to 5; i, m, and t is 0 or 1;

non-mucin type synthetic compounds or it's carrier conjugated compounds, which have above mentioned compounds as a core structure of antigen.

16 Claims, No Drawings

NON-MUCIN TYPE SYNTHETIC COMPOUNDS OR ITS CARRIER CONJUGATED COMPOUNDS

BACKGROUND OF THE INVENTION

1. The Subject of the Invention

The present invention concerns non-mucin type synthetic compounds which were linked to carrier, that is, non-mucin type synthetic compounds or it's carrier conjugated compounds. The present invention further concerns the use of non-mucin type synthetic compounds or it's carrier conjugated compounds for preparation of monoclonal antibodies, human immunodeficiency virus (HIV) agents, antitumor agents and immunostimulants.

2. Current Technology

Mucin type antigens such as Tn (GalNAc α 1→O-Ser/Thr), TF (Gal β 1→3GalNAc α 1→O-Ser/Thr), STn (NeuAc α 2→6GalNAc1→O-Ser/Thr) as shown in following below figure, are highly expressed in tumor tissues, and appearance in the nomal tissues are restricted. (G. F. Springer, J. Natl, Cancer Inst., 1975, 54, 335., S. Hakomori, Advanced in Cancer Research, 1989, 52, 257)

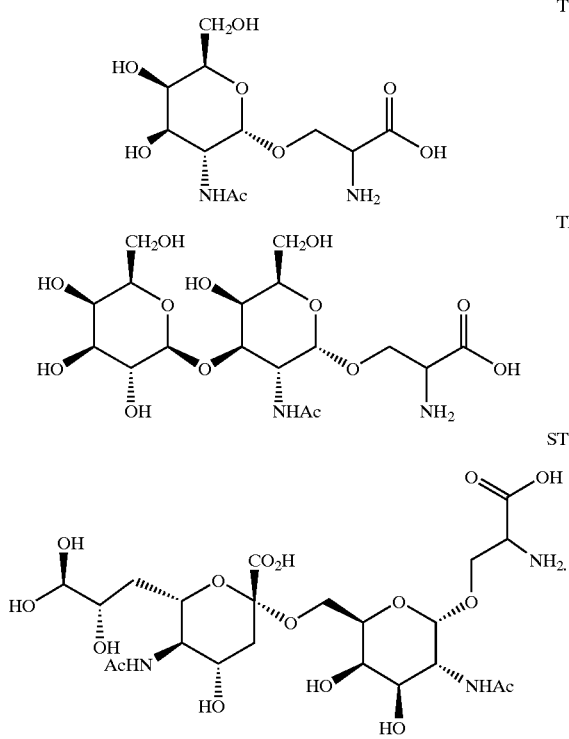

Recentry, Tn and STn epitopes, were found on the gp120 as human immunodeficiency virus (HIV) specific glycoprotein. (Hanse, J. E., J. Viol.; 1990, 64, 2833., J. Viol., 1991, 65, 6416.; Arch. Viol., 1992, 126, 11.) And it was reported that the monoclonal antibodies for the O-linked oligosaccharide block HIV infections. (Hanse, J. E., J. Viol.; 1990, 64, 2833.; Kumar A., Virology, 2000, 274, 149.)

The administration of mucin type tumor antigens and/or attached to pharmaceutically acceptable carriers are expected as a specific immunotherapy for cancer and HIV. Wherein these carriers are pharmaceutically acceptable proteins such as albumine (ALB), Keyhole limpet hemocyanin (KLH), BCG, or synthetic compounds such as palmitoyl derivatives, aromatic compounds, aliphatic compounds, alkyl, aminoalkyl, peptide and peptoid, which can obtain induction of immune response. (S. J. Danishefsky, J. Am. Chem. Soc. 1998, 120, 12474.; G. Ragupathi, Glycoconjugate J., 1998, 15, 217.; B. M. Sandmeier, J. Immunotherapy, 1999, 22(1), 54.; A. Singhal, Cancer Res., 1991, 51, 1406.; T. Shimizu, 1987, 55, 2287–2289.)

However, above mentioned mucine type antigens-carrier have O-glycoside linkage between sugar and carrier moiety. Therefore, considering about their metabolic stability and immunogenicity, these O-glycoside linkage are susceptible to hydrolyze by glycosidase such as N-acetyl galactosaminidase (EC 3.2.1.49) (Eq A), or hydrolyze of peptide bond by peptidase,as shown in following equation (Eq B), and their activities are anticipated to decrease or attenuate.

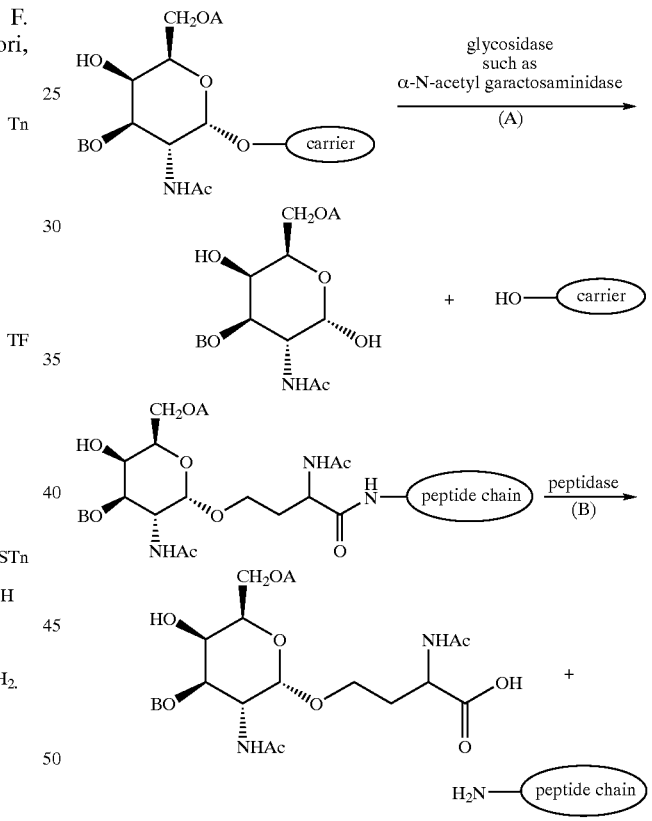

On the other hand, Beau et al have been synthesized the C-glycosides (GalNAc α 1→CH$_2$-Ser) that have the carbon atom instead of the oxygen atom which connect with serine and N-acetyl galactosamine as a metabolically stable Tn antigen, shown in following equation (A). This Tn antigen is stable against glycosidase such as N-acetyl galactosaminidase (Beau et al, J. C. S. Chem. Commun., 1998, 955.). But, when these C-glycosides are attached to peptides, these compounds could be hydrolyzed by peptidases, and their stabilities are not satisfactory in a living body.

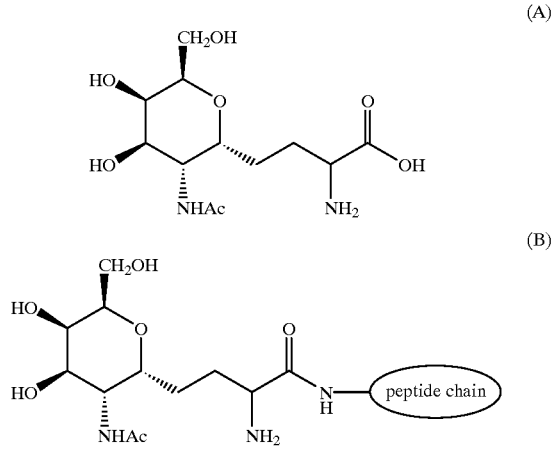

(A)

(B)

And Roy et al have been synthesized the glycopeptoids as the metabolic stable mimic of carbohydrate antigen, which was attached to peptoid that is metabolically stable against hydrolysis by peptidase, as shown in following equation (Tetrahedron Lett., 1997, 38, 3487.). But, his reported compounds are thought to be unstable, because it is also expected to be hydrolyzed by glycosidases such as N-acetyl galactosaminidase.

Beau and Roy have not reported to pharmacological activities of Tn antigen linked to carrier proteins.

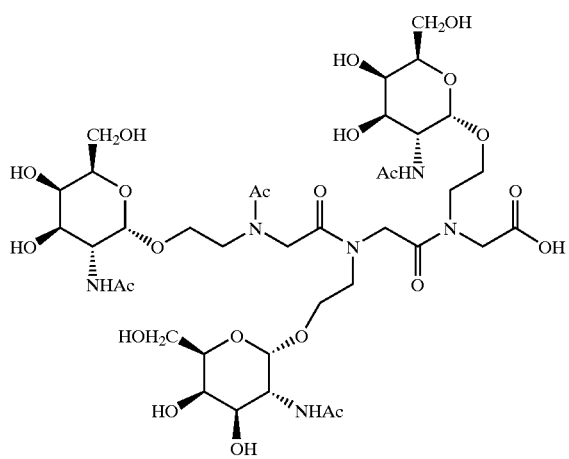

As mentioned above, the compound, prepared from a coupling of the precedented naturally occuring mucin type antigen and the carrier, is hydrolyzed at it's glycoside bond by glycosidase which exists widely in a living body and at it's peptide bond by peptidase. Therefore it is expected to obtain an insufficient effect.

3. The Subject of Invention

Under these situations, this invention was attained to solve these problems. The purposes of this invention are to prepare the non-mucin type synthetic compounds-carrier conjugated compounds which are stable to hydrolyze against both enzymes, glycosidase and peptidase.

And to prepare non-mucin type synthetic compounds-carrier conjugated compounds which have the ability of specific reactivity to induce immune response for cancer and HIV and have excellent active immunization activities.

And to prepare non-mucin type synthetic compounds-carrier conjugated compounds which are able to obtain selective monoclonal antibodies for cancer and HIV.

And to prepare anti-tumor agents, anti-HIV agents and immunostimulants which contain this non-mucin type synthetic compounds-carrier conjugated compounds as active ingredients.

And the method to prepare N-acetyl galactosamine in cost effectively, starting material of non-mucin type synthetic compounds-carrier conjugated compounds, is the another object of present invention.

4. A Solution of the Problem

Under these backgrounds, we maked effort to consider to prepare the metabolic stable compounds, having C-glycoside and peptoid, against to glycosidase and peptidase and the non-mucin compound as shown in following figure, were synthesized for the first time. These compounds are, so to speak, C-glycopeptoid and new compounds.

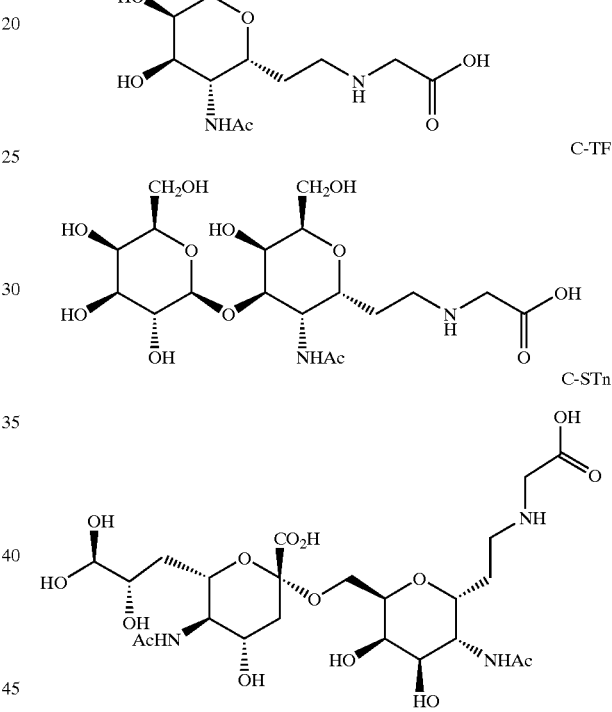

These C-glycopeptoids are more metabolically stable against glycosidase and peptidase than known vaccines. Furthermore, they are able to show their effects for longer time and to store for long term at room temperature. When these novel C-glycopeptoids which are attached to pharmaceutically acceptable carrier proteins, these compounds are more metabolically stable in a living body than known vaccines against glycosidase and peptidase and also expected to show the excellent active immunization activities. It is expected that these novel C-glycopeptoids have potent passive immunogenicities for cancer and HIV. Monoclonal antibodies which were prepared using these compounds are expected to have activities for cancer therapy as a possive immune response. And these compounds have antitumor, anti HIV activity and immunopotentiation.

As a result of investigation of novel compounds as anti HIV agents and immunostimulant, the antibodies which was prepared using novel compound have excelent antitumor, anti HIV activity and immunostimulaion as shown in general formura (1).

DETAILED DESCRIPTION OF THE INVENTION

A compound of the general formula (1),

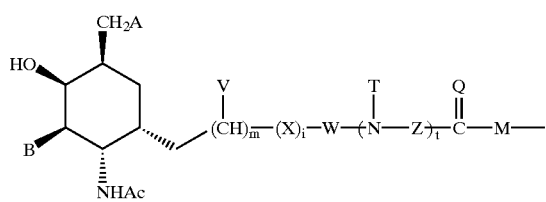

(1)

wherein A represents OH or sialic acid and/or it's derivatives, and B represents OH or galactose and/or it's derivatives; T represents H or protecting groups of amine; M represents H or OH; X represents oxygen atom, —NH— or S(O)z (where z is 0, 1 or 2); Q is H or oxygen atom; V represents lower alkyl or H; W is straight or branched alkylene groups from 0 to 5; Z is straight or branched alkylene groups from 1 to 5; i, m, and t is 0 or 1;

non-mucin type synthetic compounds or it's carrier conjugated compounds, which have above mentioned compounds as a core structure of antigen.

In the explanation of T, protecting groups of amin are alkyl, acetyl, t-butyloxycarbonyl, benzyloxycarbonyl group, and others. W is straight or branched alkylene groups from 0 to 5. And general formura (1) is called non-mucin compound in this invention.

Compound (1) have immunopotentiation and non-mucin type synthetic compounds or it's carrier conjugated compounds can be prepared from compound (1) or 2-5 clustered of compound (1) linked with the synthetic compounds such as palmitoyl derivatives which can obtain inductions of immune response.

A compound of the general formula (2),

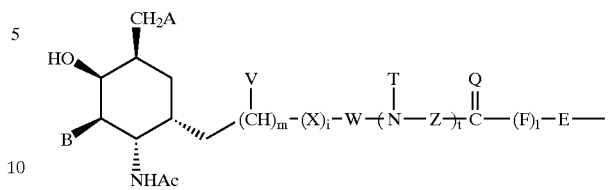

(2)

wherein A, B, T, X, Q, V, W, Z, i, m, and t have above-mentioned meanings; E represents pharmaceutically acceptable carrier compounds; l is 0 or 1; F is showed followings,

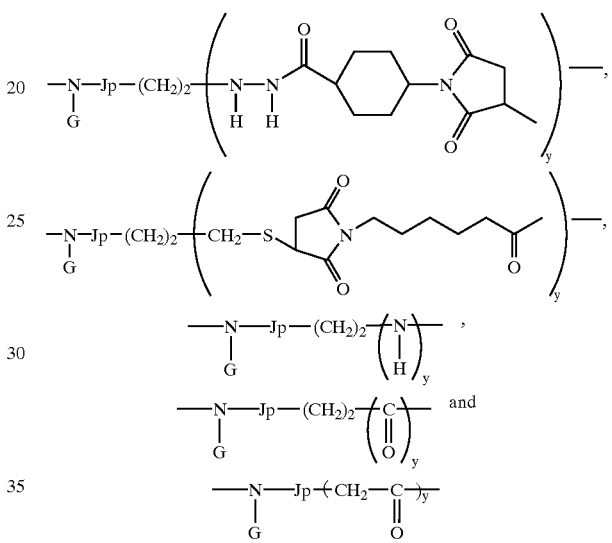

wherein J is —CH$_2$CH$_2$X— or —N(L)—CH$_2$CO— (where X have above-mentioned meanings; L is H or lower alkyl); G is H or lower alkyl; p is 0 to 3; y is 0 or 1;

non-mucin type synthetic compounds or it's carrier conjugated compounds, which have above compounds as a core structure of antigen.

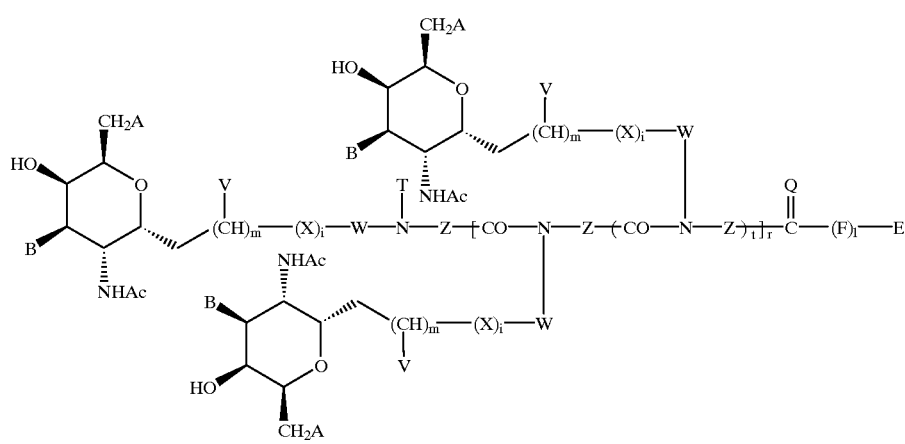

(3)

wherein A, B, T, X, Q, V, W, Z, i, m, t, E, and l have above-mentioned meanings; r is from 1 to 4; non-mucin type synthetic compounds or it's carrier conjugated compounds, which have above compounds as a core structure of antigen.

A compound of the general formula (4),

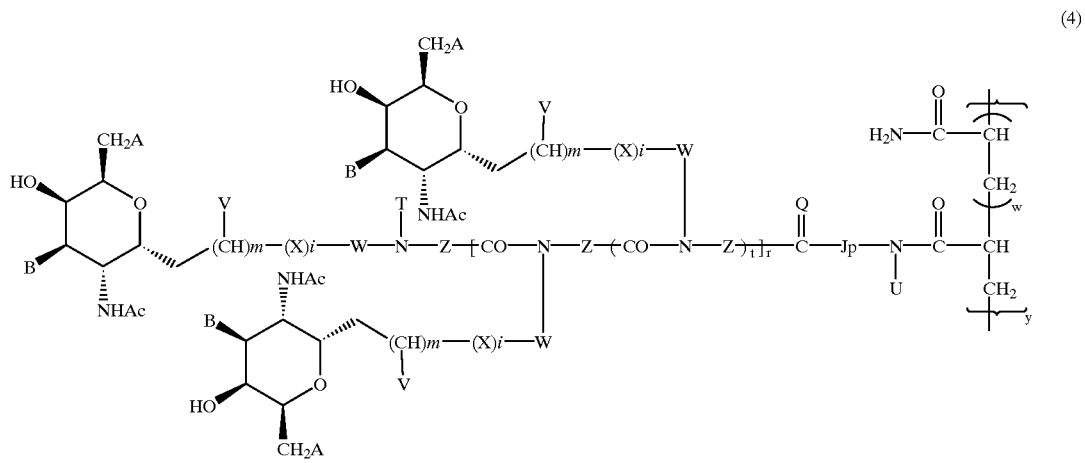

(4)

wherein A, B, T, X, Q, V, W, Z, J, i, m, t, p, and r, have above-mentioned meanings; U represents H or lower alkyl; w is 0 to 50; y is 1 or 50.

In the explanation of E, pharmaceutically acceptable proteins are such as albumins (ALB), Keyhole limpet hemocyanin (KLH), BCG, or synthetic compounds such as palmitoyl derivatives, aromatic compounds, aliphatic compounds, alkyl, aminoalkyl, peptide and peptoid, which can obtain induction of immune response.

Non-mucin type synthetic compounds or it's carrier conjugated compounds contain general formula (1) as a core structure. These compounds are able to apply to mammal such as human, and these are used as anti-tumor agents and/or anti-HIV agents having immunostimulate activities. These compounds are also used for the preparation of monoclonal antibodies. These novel compounds are able to elongate of effective time, to decrease of dosage, and to reduce of side effects, further the compounds of the invention are expected to have the potent immunogenicities for cancer and HIV than known vaccines. It is expected that monoclonal antibodies, prepared from this invention, have excellent antitumor and anti HIV activity. Furthermore, when neuraminidase inhibitors such as Zanamivir or Oseltamivir are co-administrated with sialic acid contained compounds in this invention, these sialic acid contained compounds are expected to be more stable in a living body.

N-acetyl galactopyranose moiety in mucin type (O-Tn, O-STn, O-TF) or non-mucin type (C-Tn, C-STn, C-TF) antigens was synthesized from N-acetyl galactosamine that is very expensive as a starting material. On the other hand, N-acetyl glucosamine, isomer of N-acetyl galaccosamine at C-4 hydroxy group, is cheaper and readily available. So it is hoped to use cheaper N-acetyl glucosamine as starting material.

Following this invention N-acetyl galactosamine derivatives can be synthesized from N-acetyl glucosamine via inversion of C-4 hydroxy group.

That is to say the process for the preparation of N-acetyl galactosamine derivatives, general formula (6) can be prepared from the inversion of $OR_2$ group to $OR_1$ group at C-4 position in N-acetyl glucosamine derivatives, general formula (5).

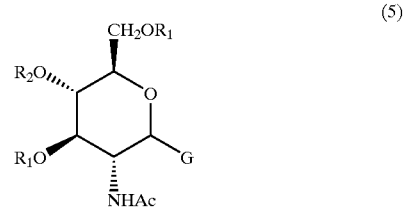

(5)

wherein $R_1$ is H or a protecting group of a hydroxy group such as acetyl group; $R_2$ is a leaving group such as tosylate, trifluoromesylate or methansulfonate; G is allyl or protected hydroxyl groups.

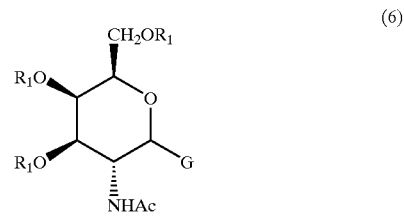

(6)

Herein we descrived the method for preparing the key intermediate, galactose derivatives, (1a-1l), and also general formula (1).

1) Synthesis of Intermediate 1a-11

(i) Route 1-a

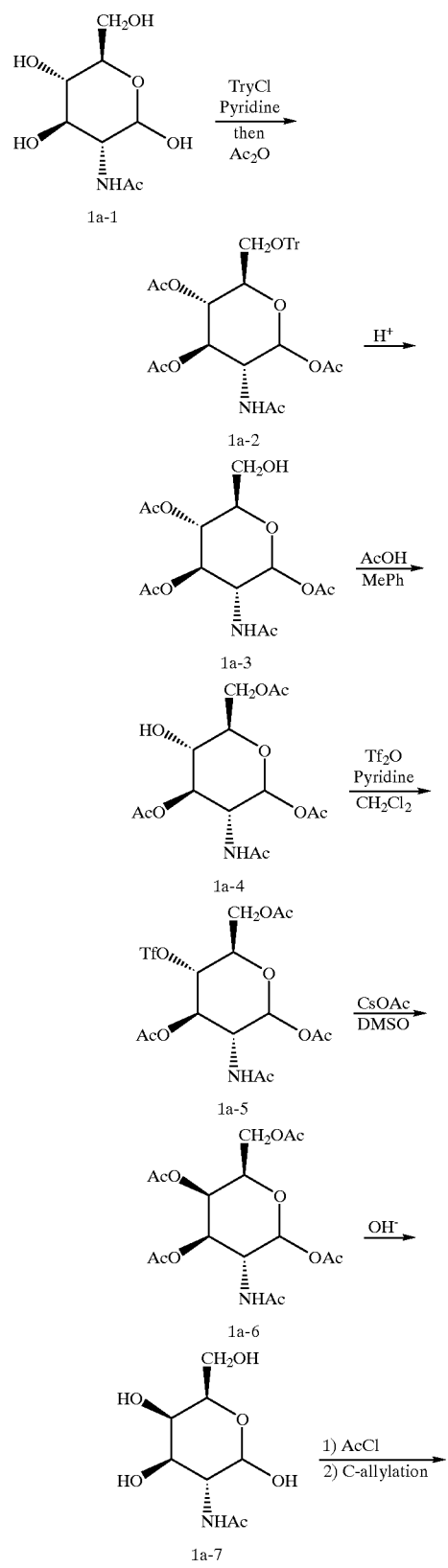

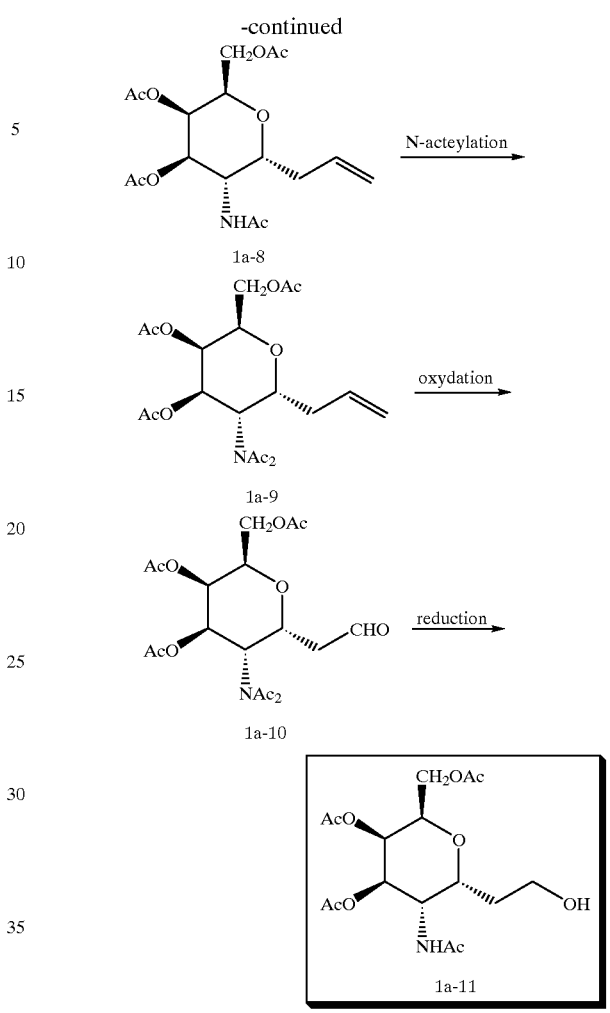

The intermediate 1a-11 is synthesized starting from readily available N-acetylgulucosamine as shown in route 1-a via inversion of C-4 hydroxy group.

N-acetylglucosamine is selectively protected by trityl ether at C-6 position (B. Helferich et al, Ann., 1920, 450, 219.), followed by acetylation at C-3, 4 and treated with formic acid aford compound 1a-3 (M. Bessodes, Tetrahedron Lett., 1986, 27, 579.).

The 4-hydroxyl intermediate 1a-4 is obtained via acetyl migration of the compound 1a-3 by heating with a acetic acid in toluene (D. Chaplin et al, *J. Chem. Soc. Perkin Trans. 1*, 1992, 235.).

The preparation of 4-hydroxyl derivative is selectively protected as benzoyl or pivaloyl ester at position C-3 and 6 by only one step procedure.

4-hydroxyl group is transformed to triflate 1a-5 and the inversion step is carried out using cesium acetate to give N-acetyl-1,3,4,6-tetra-O-acetyl-D-galactosamine 1a-6.

Methanesulfonyl chloride or p-toluenesulfonyl chloride can be used instead of trifluoromethanesulfonyl chloride. Then compound 1a-6 is deacetylated to N-acetyl-D-galactosamine. And this epimerization at C-4 position was carried out by the procedure of Cipolla et al (Tetrahedron Asymmetry, 2000, 295–303). Allyl group is introduced into compound 1a-7 by Horton's procedure (Carbohydr. Res., 1996, 309, 319–330).

Compound 1a-7 is reacted with acetyl chloride, followed by allylation using allyltributyltin and 2,2'-azobis isobutylonitril (AIBN) to obtain compound 1a-8. But, the method of allylation is not restricted by this allylation method.

2-Acetamide group is protected as N,N-diacetyl using isopropenyl acetate in the presence of catalytic amount of acid to afford compound 1a-9 (J. Oui. Horton et al, Carbohydr. Res, 1996, 309, 319–330.). Compound 1a-9 is reacted with osumium oxide and NaIO₄ to obtain aldehyde compound 1a-10. Compound 1a-10 is subjected to reduction using sodium brohydride to give compound 1a-11.

(ii) Route 1-b

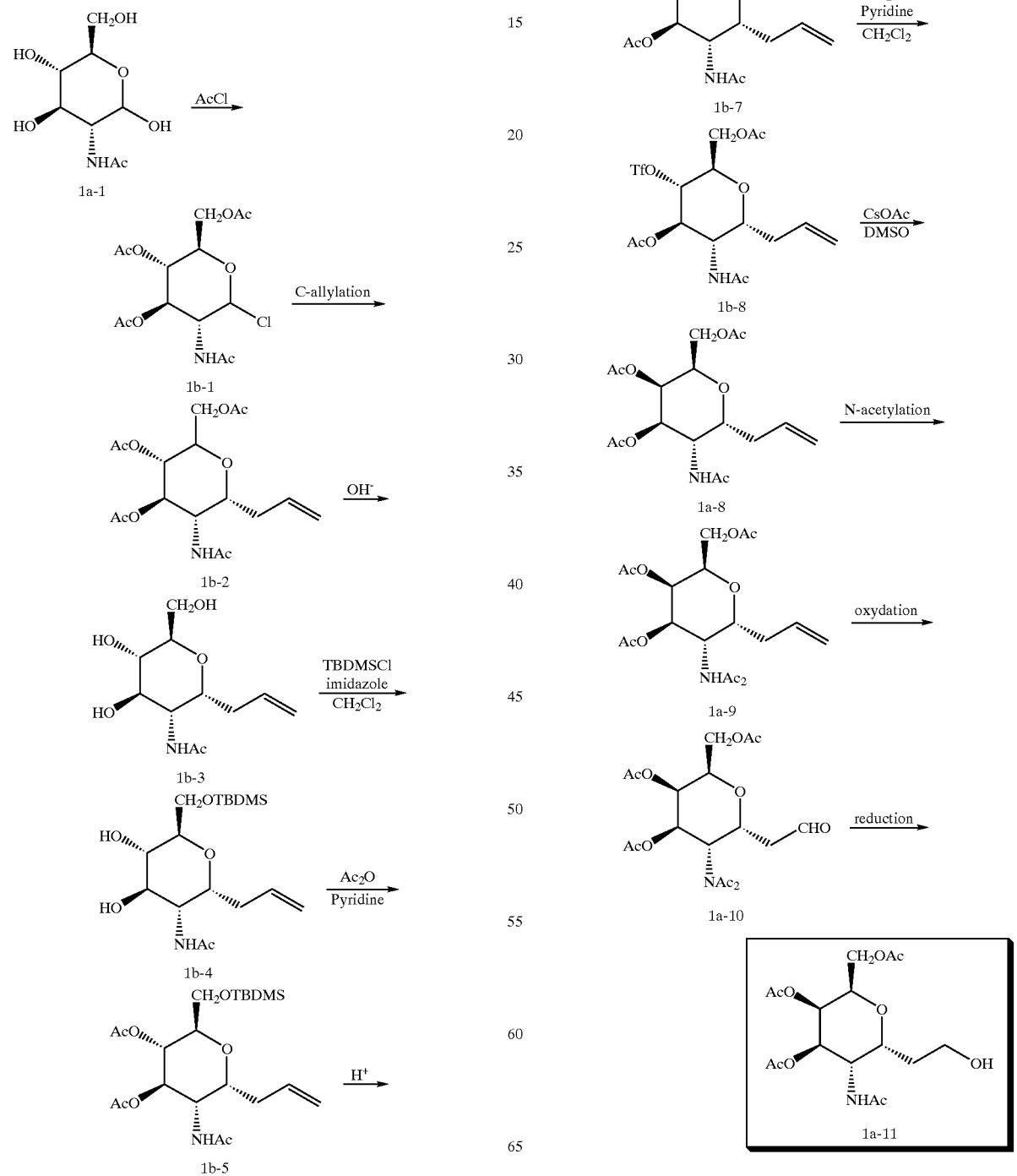

The intermadiate 1a-11 is also synthesized starting from N-acetyl-D-glucosamineas shown in route 1-b. The compound 1a-1 is inverted at C-4 hydroxyl group after induction of allyl group (B. A. Roe et al, J. Org. Chem, 1996, 61, 6442–6445.). N-acetyl-D-glucosamine is treated with acetyl chloride followed by C-allylation with allyltributyltin afford compound 1b-2. Compound 1b-2 is deacetylated with NaOMe to afford compound 1b-3. Then compound 1b-3 is selectively protected as t-butyldimethylsilyl (TBS) ether at C-6 position, followed by acetylation with acetic anhydride under basic conditions to give compound 1b-5. Compound 1b-5 is desilylated by acids and rearrengement to compound 1b-7 by heating with a catalytic amount of acetic acid in toluene.

Synthesis of compound 1a-11 from 4-hydroxyl compound 1b-7 is obtained by simillar method as described in route 1-a.

2) Synthesis of Compound 2-5: Route 2

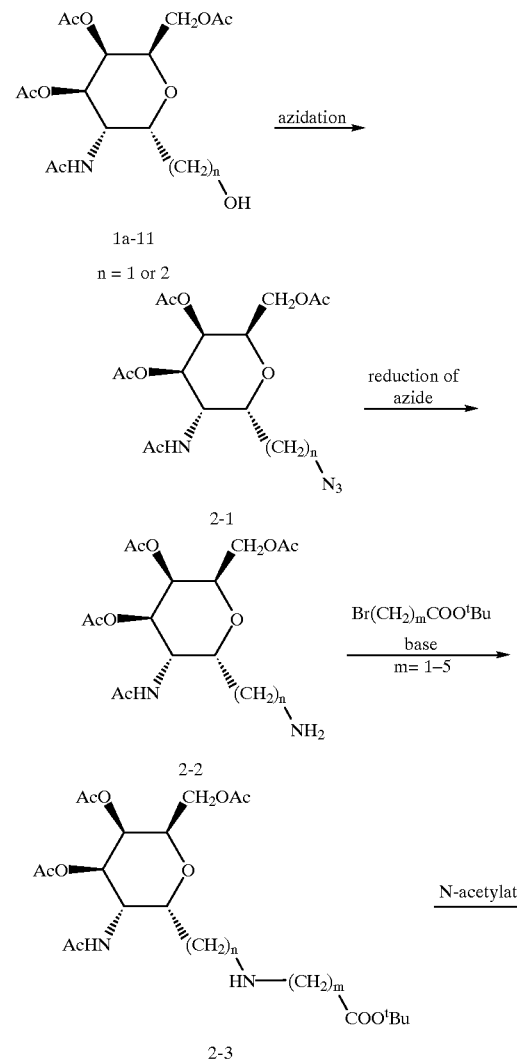

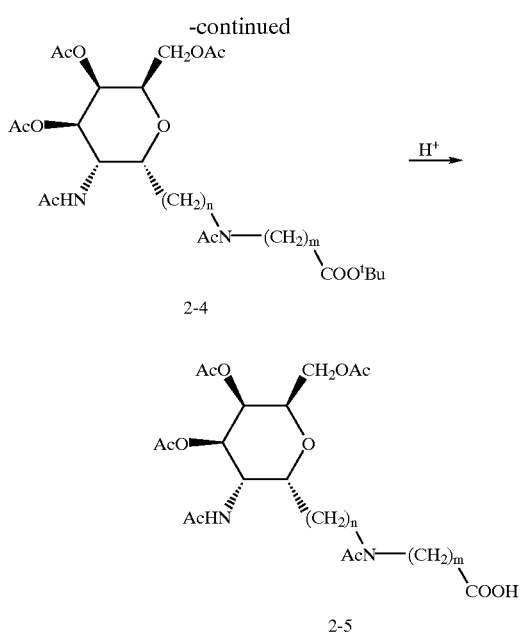

Compound 1a-11 is converted to 2-1 by Mitsunobu reaction (O. Mitsunobu, Synthesis, 1, 1981.). Then azide group of compound 2-1 is reduced to primary amine; for example hydrogenation using Pd—C.

Alkylation of compound 2-2 with haloester, for example butyl bromo acetate, give compound 2-3. Compound 2-3 is protected as acetamide using acetic anhydride or acetyl chloride. Compound 2-5 was obtained by deprotection of compound 2-4.

3) Synthesis of Compound 2-3: Route 3

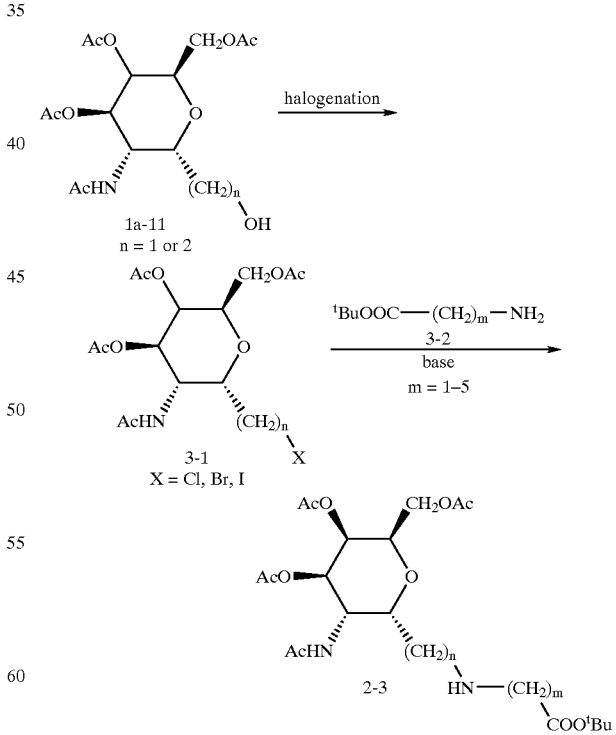

The hydroxyl group in compound 1a-11 is converted to leaving group such as halogen, followed by coupling with compound 3-2 in the presence of base give compound 2-3. But, the leaving group is not restricted to halogens.

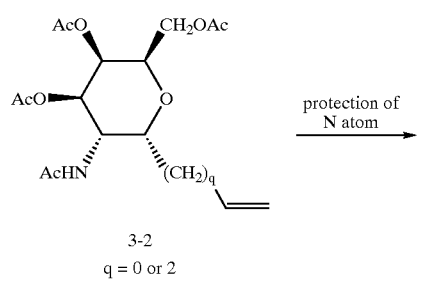

3-2
q = 0 or 2

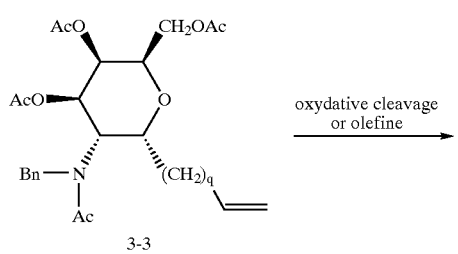

3-3

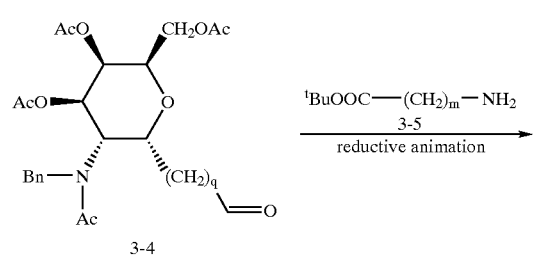

3-4

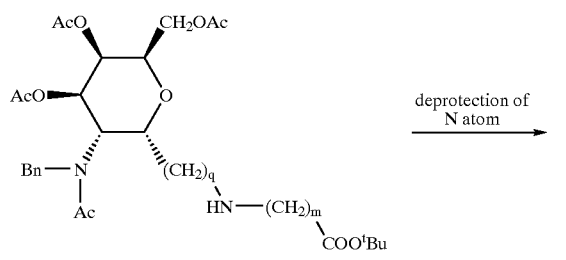

3-6

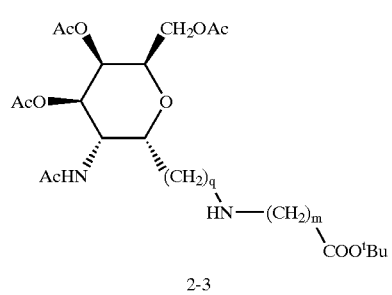

2-3

Acetamide group in compound 3-2 is protected as suitable protecting group, for example benzylamide, followed by oxdative-cleveage of olefine to provide aldehyde 3-4. Reductive amination with compound 3-5, followed by deprotection give compound 2-3.

4) Synthesis of Compound 4-5: Route 4

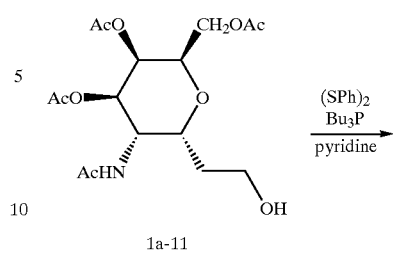

1a-11

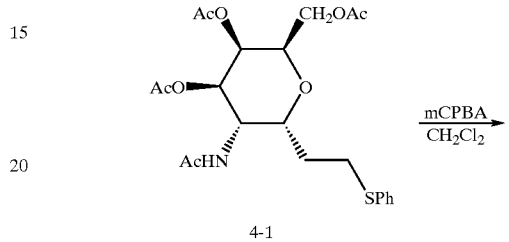

4-1

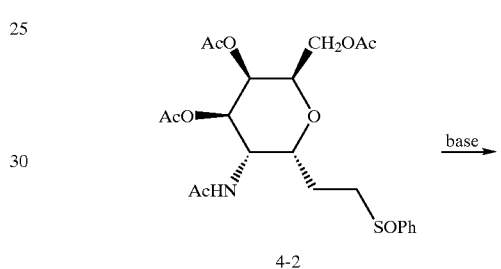

4-2

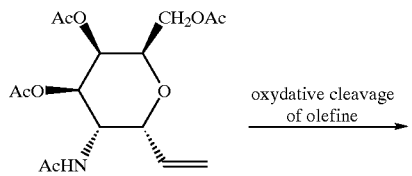

4-3

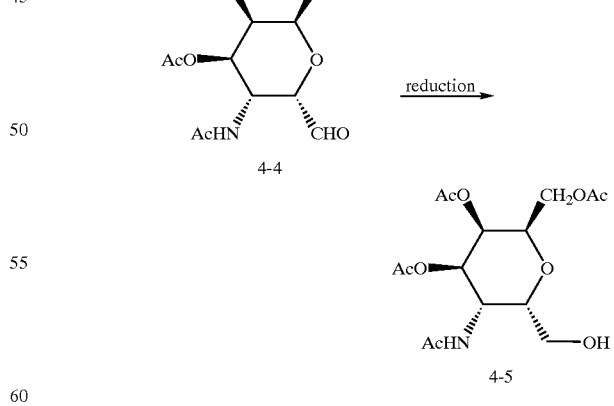

4-4

4-5

Compound 1a-11 is reacted with diphenyldisulfide to give compound 4-1, followed by oxdation using m-chloroperbenzoic acid to give compound 4-2. Then, heating in the presence of amine give olefin compound 4-3. The compound 4-3 is oxidized, followed by reduction give compound 5-8 as described route 1.

5) Synthesis of Compound 5-8: Route 5

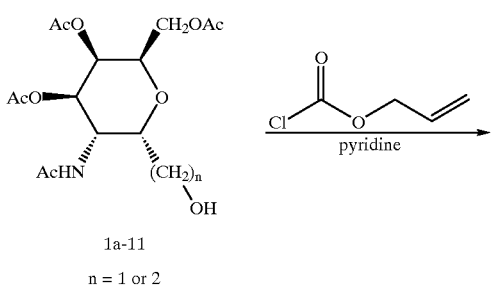

1a-11
n = 1 or 2

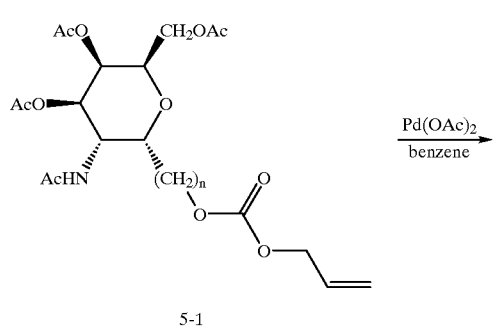

5-1

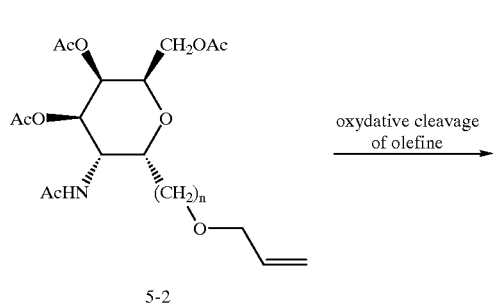

5-2

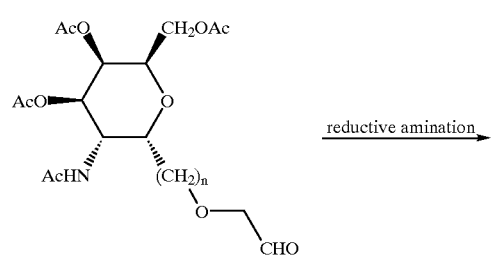

5-3

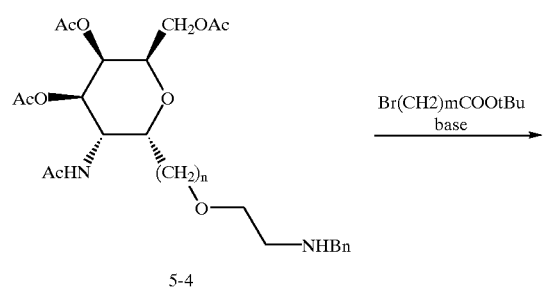

5-4

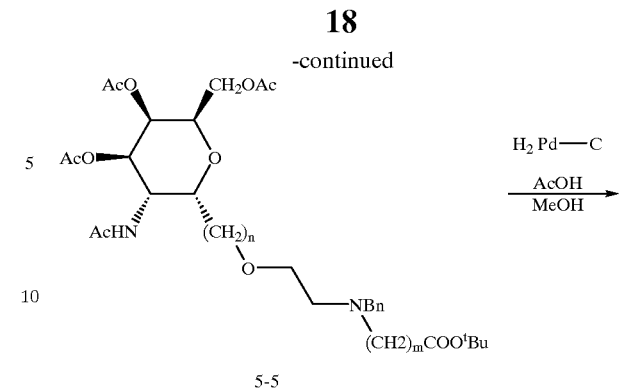

5-5

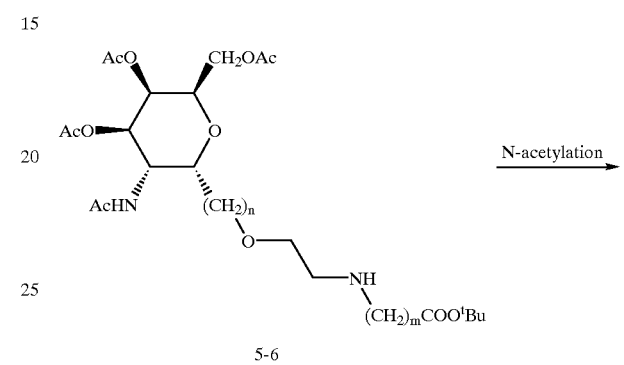

5-6

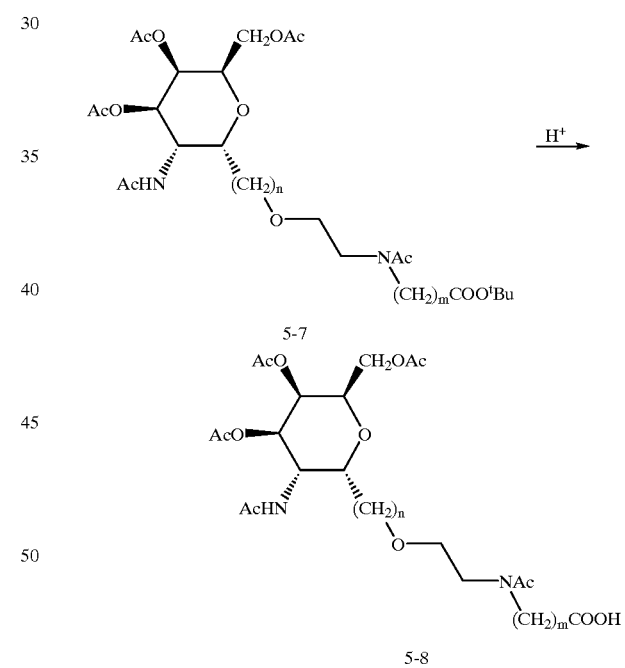

5-7

5-8

Allyl group is introduced into compound 1a-11 by the method of Curibe et al (Tetrahedron Lett., 1981, 22, 3591–94). Ozonolysis or oxidative cleveage of compound 5-2 afford compound 5-3 by $OsO_4$. The reductive amination of compound 5-3 using amine, for example benzylamine, give compound 5-4. The compound 5-4 is coupled with haloester (for example butyl bromoacetate) provide compound 5-5. Then amino group of the compound 5-5 is deprotected by hydrogenation, followed by acetylation and debutylation give compound 5-8.

6) Synthesis of Sialyl Acid Derivatives: Route 6
   (i) Route 6-a
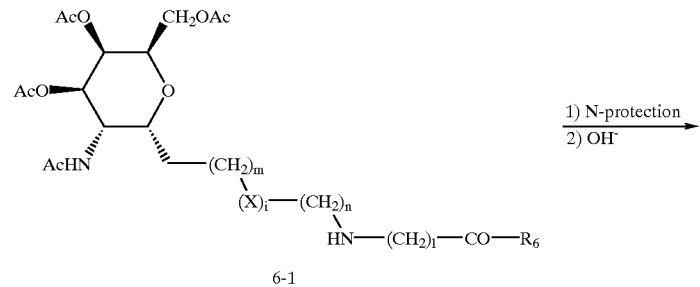
6-1
m = 1 or 0
n = 1–5      $R_6 = O^tBu$
l = 1–5
X = O, S, NH    NH—$(CH_2CH_2O)_u$—$CH_2CH=CH_2$
i = 0 or 1
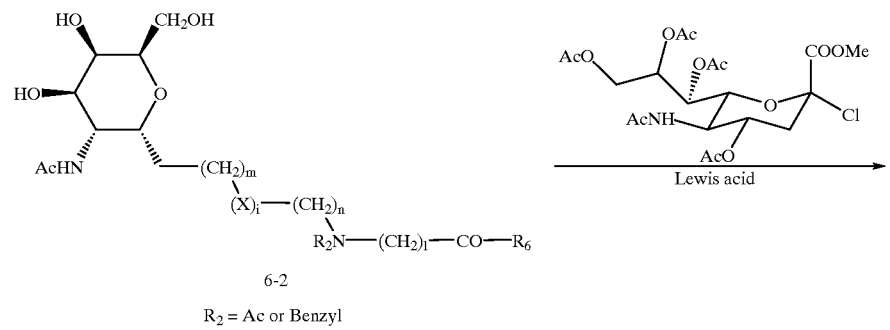
6-2
$R_2$ = Ac or Benzyl
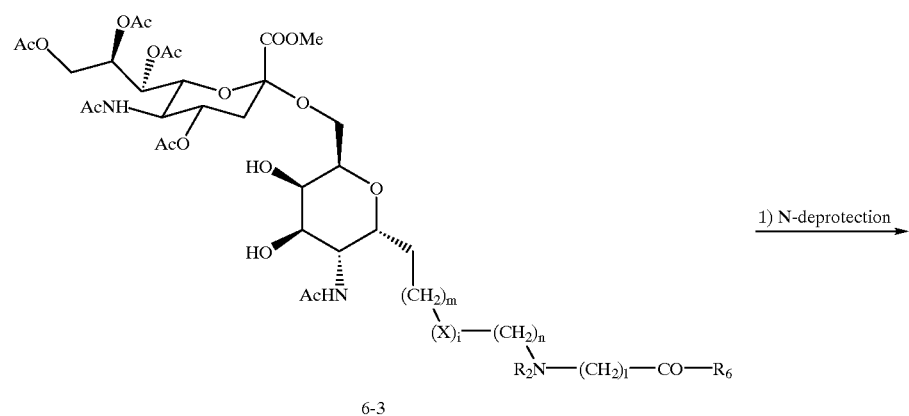
6-3
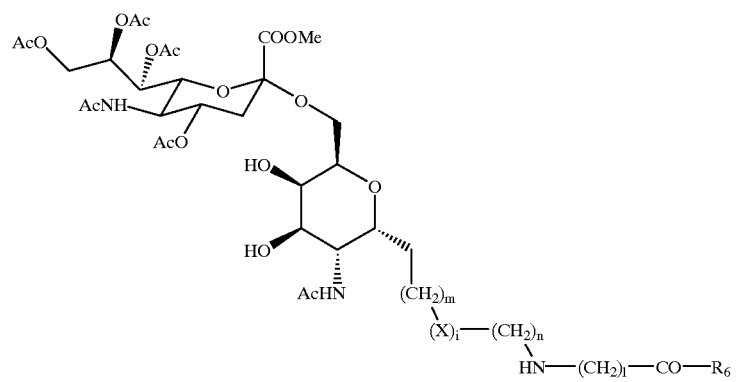
6-4

The protection of amino group, followed by deacetylation give compound 6-2. The compound 6-2 is glycosilated with sialic acid derivatives by Danishefsky's procedure (J. Am. Chem. Soc., 1999, 121, 2662–2673.). And, leaving group in this reaction is not restricted to halogens. Obtained compound 6-3 can be converted to compound 6-4 as a intermadiate of cluster.

(ii) Route 6-b

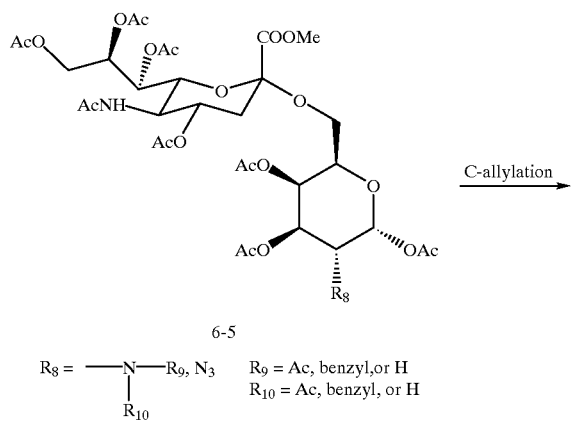

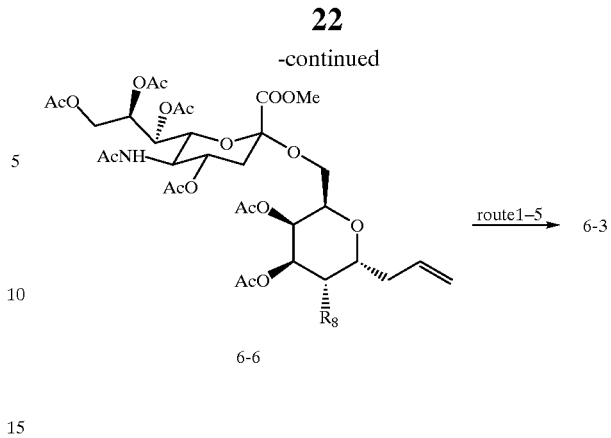

The α-C-glycoside 6-6 is obtained by C-allylation of compound 6-5. Synthesis of compound 6-3 from compound 6-6 is simillar to described route 1-5. And this reaction also can be proceeded using sialyl transferase and sialic acid derivatives (C. Pauison et al. J. Am. Chem. Soc., 1990, 112, 9308–9309).

7) Synthesis of Galactose Derivatives: Route 7

(i) Route 7-a

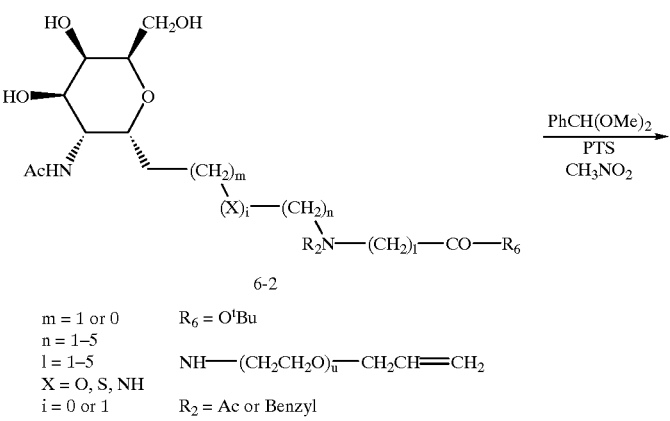

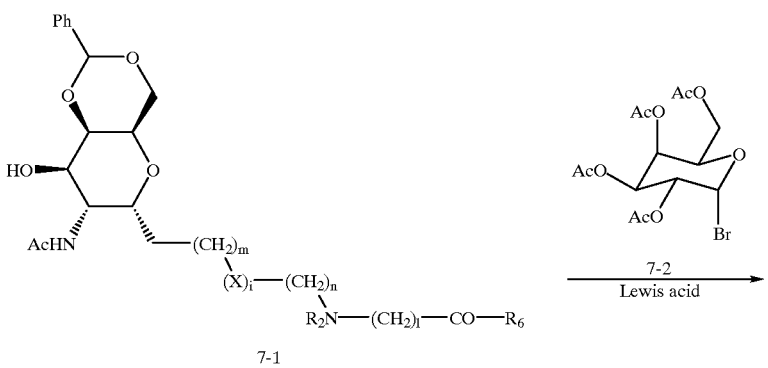

-continued

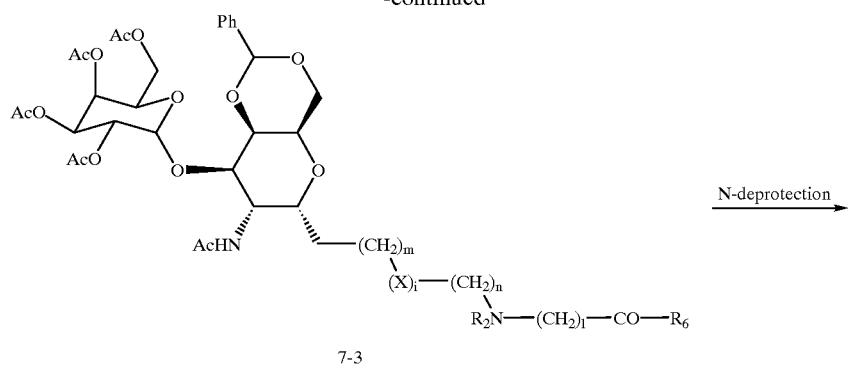

7-3

→ N-deprotection

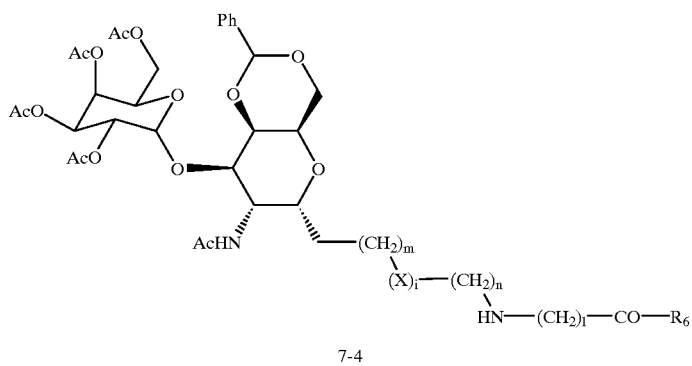

7-4

Compound 7-1 is obtained by hydroxyl group protection of compound 6-2. The compound 7-1 is glycosilated with acetobromo galactose to give compound 7-3. And, the leaving groups in this reaction is not restricted to halogen. Compound 7-3 can converted to compound 7-4 as a intermadiate of cluster.

(ii) Route 7-b

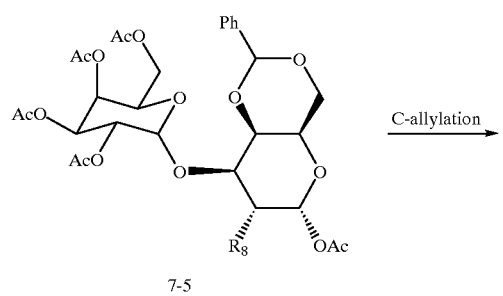

7-5

$R_8 =$ —N—$R_9$, $N_3$   $R_9$ = Ac, benzyl, or H
         |
         $R_{10}$              $R_{10}$ = Ac, benzyl, or H → C-allylation -continued

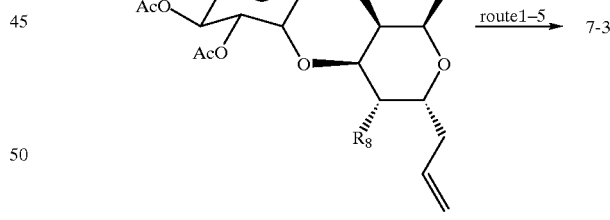

7-6

→ route1–5 → 7-3

The α-C-glycoside 7-6 is obtained by C-allylation of compound 7-5. Synthesis of compound 7-3 from compound 7-6 is simillar to described route 1-5. And this reaction also can be proceeded using sialyl transferase and sialic acid derivatives (C. Pauison et al. J. Am. Chem. Soc., 1990, 112, 9308–9309).

8) Synthesis of Culster Derivatives: Route 8

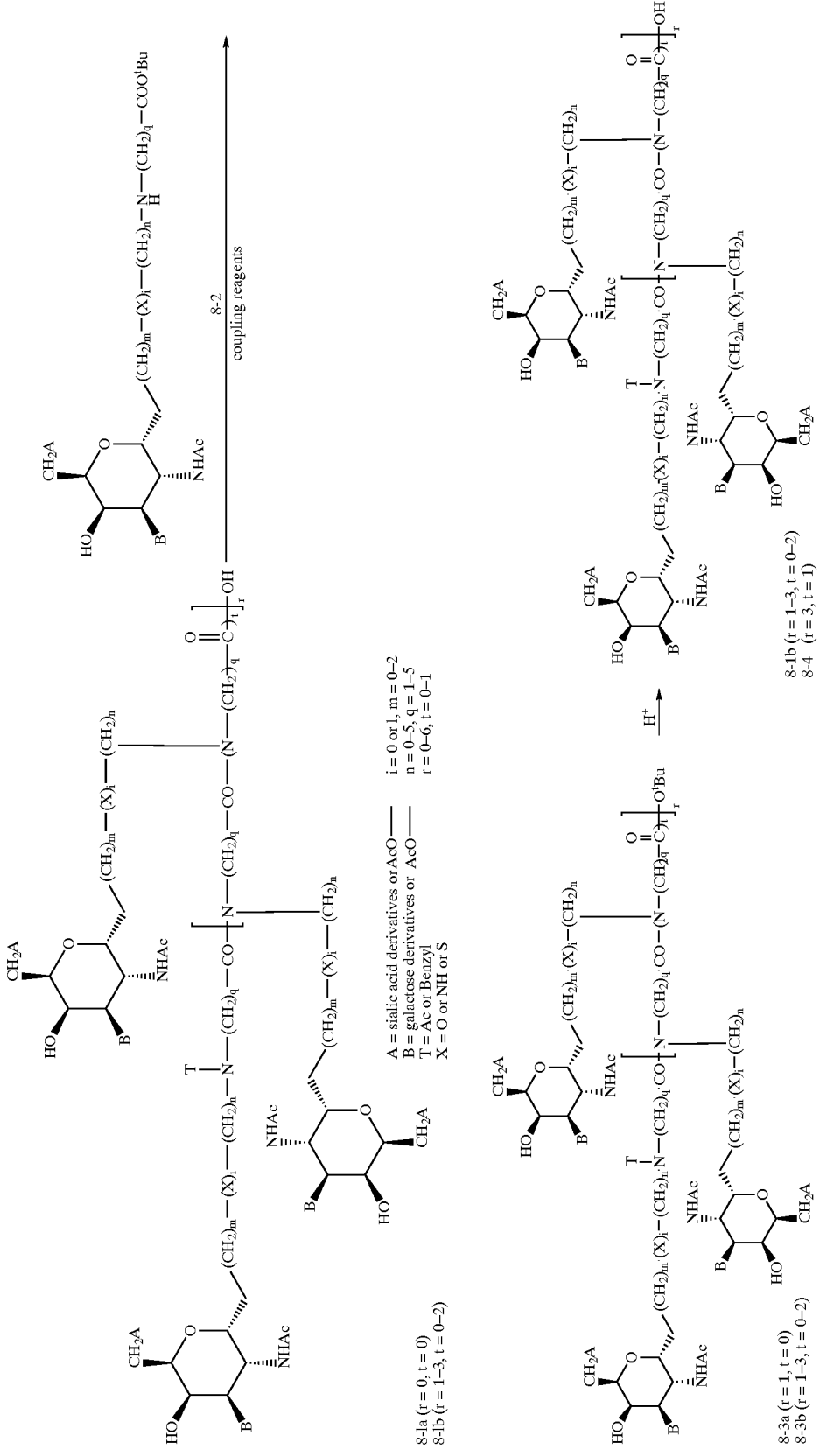

Compound 8-3 is obtained by coupling compound 8-1a with compound 8-2 by P. Roy's procedure (Tetrahedron Lett., 1997, 38, 13478–13490.). Compound 8-1b is synthesized by deprotection of compound 8-3, followed by coupling with compound 8-2 afford compound 8-3b. Compound 8-1b, 4 is obtained by deprotection of ester in compound 8-3a, b.
9) Coupling Linker with Haptens: Route 9
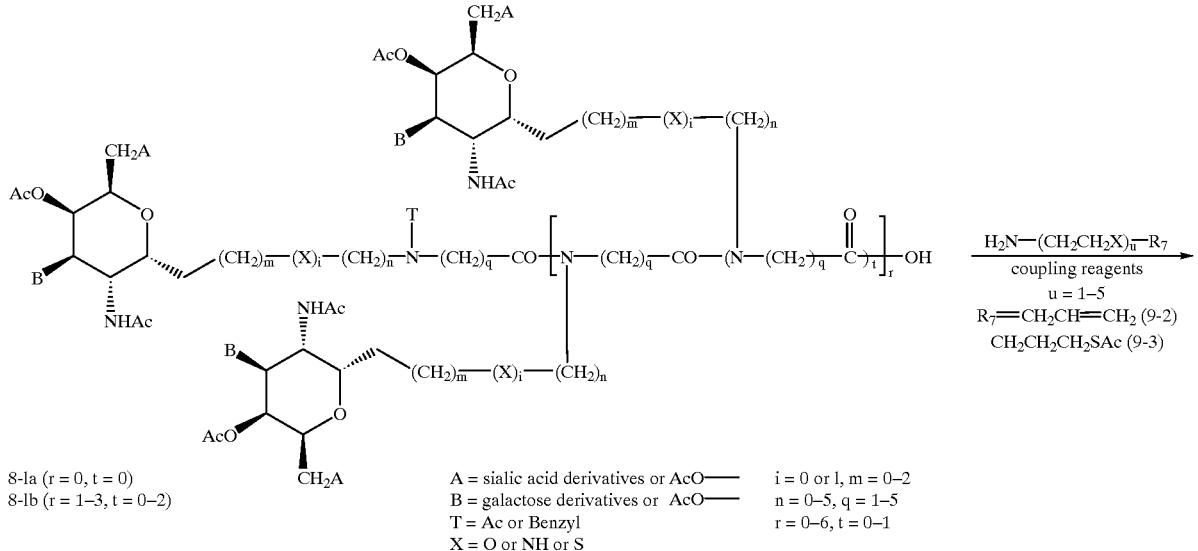
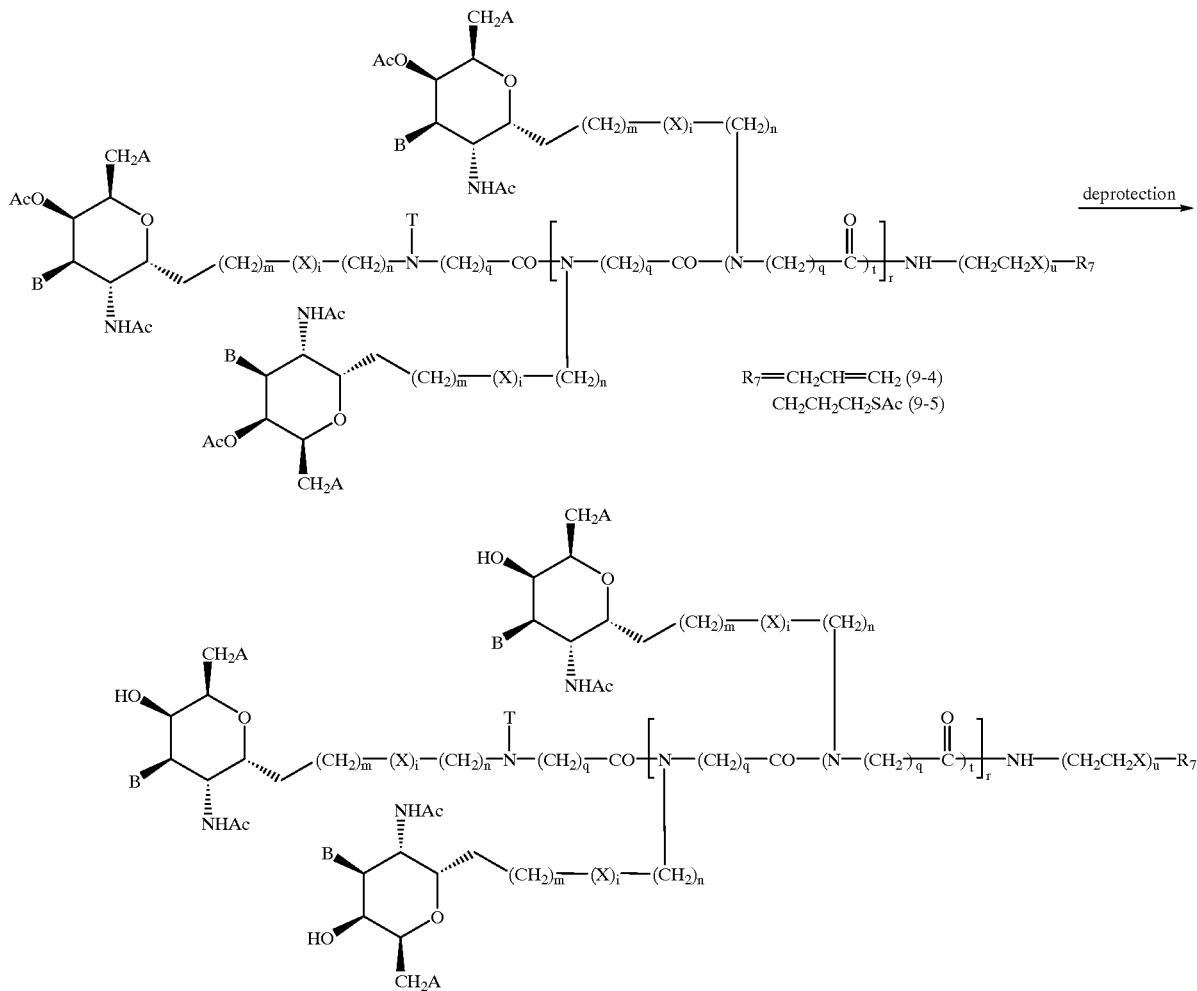

Compound 9-4 and 9-5 are prepared from coupling linker 9-2 or 9-3 with compound 9-1 respectively (P. Roy et al, Tetrahedron Lett., 1997, 38, 3478–3490). And this coupling can be proceeded used to other reagents such as N,N-dicyclocarbodiimide, Danishefsky's procedure (J. Am. Chem. Soc., 1998, 120, 12474–12485) or 2-isobutyl-1-isobutoxycarbonyl-1,2-dihydroquinoline. Compound 9-7 is obtained by deprotection of hydroxy group.

10) Coupling Carrier with Hapten: Route 10

Compound 9-5 is coupled with maleimidated protein by Khono's method (J. Clin. Lab. Anal., 1999, 10, 91.) afford compound 10-12.

Compound 10-7 is obtained by coupling carboxylic group in compound 10-1 with amino groups. Compound 10-13 is obtained by coupling aminogroup in compound 10-8 with carboxylic groups in protein. And Coupling compound 10-1 with palmitoyl derivatives by Danishefsky's method (J. Am. Chem. Soc., 1999, 121, 2662–2673.) give compound 10-6.

11) Synthesis of Polymer Derivatives: Route 11-a

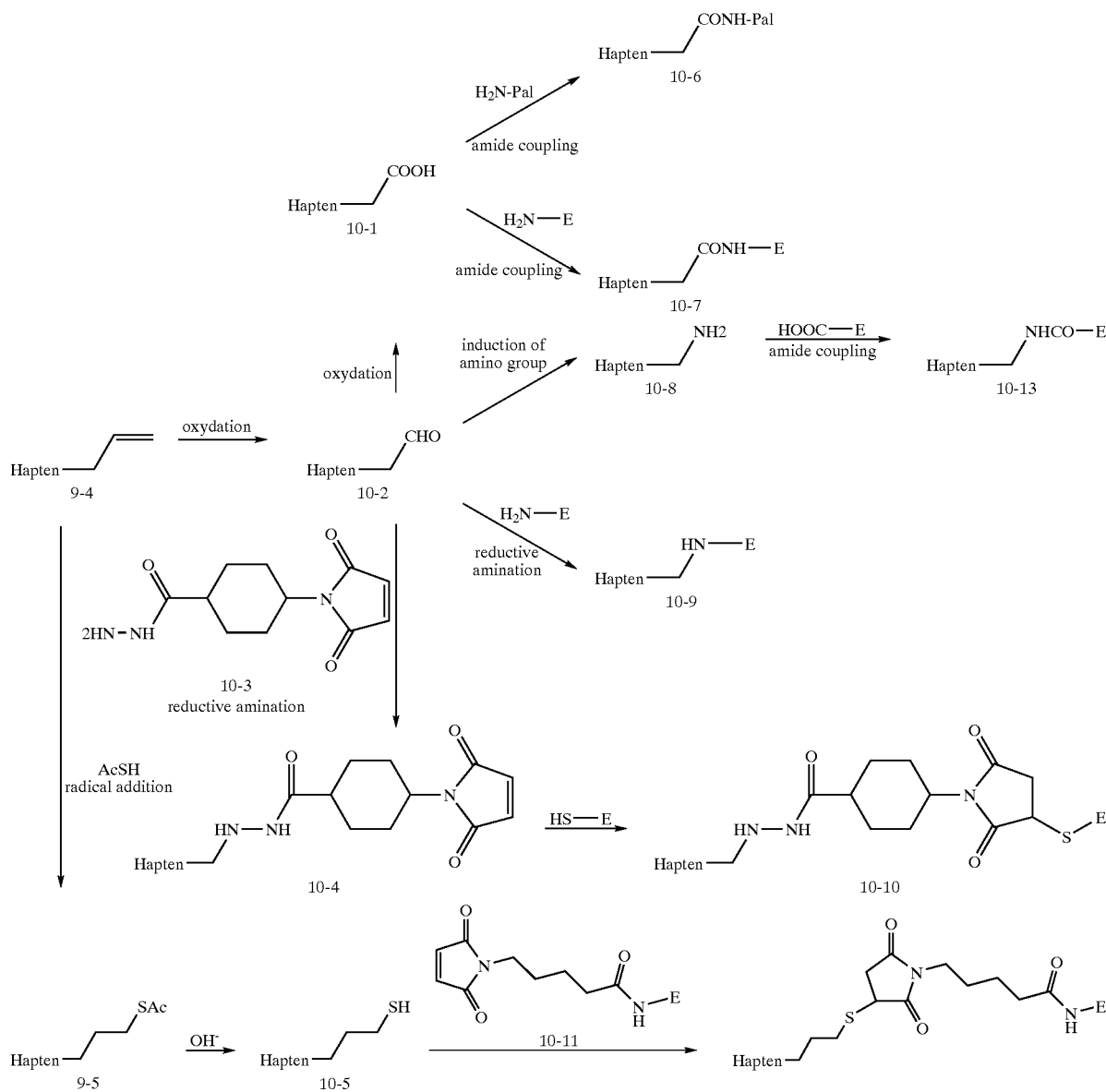

Compound 9-4 is oxidized to aldehyde 10-2, followed by reductive amination with protein using sodium cyanoborohydride in phosphate buffer (pH7.2) affod compound 10-9 by Livingston's method (Glycoconjugate Journal, 1998, 115, 217–221.). Compound 9-4 is also coupled with protein by Slovin's method (Proc. Nat. Acad. Sci. USA, 1999, 96, 5710.). Compound 9-4 is converted to maleimide compound 10-4, followed by coupling with thiol group in protein or compound 9-4 is converted to thioacetate compound 9-5.

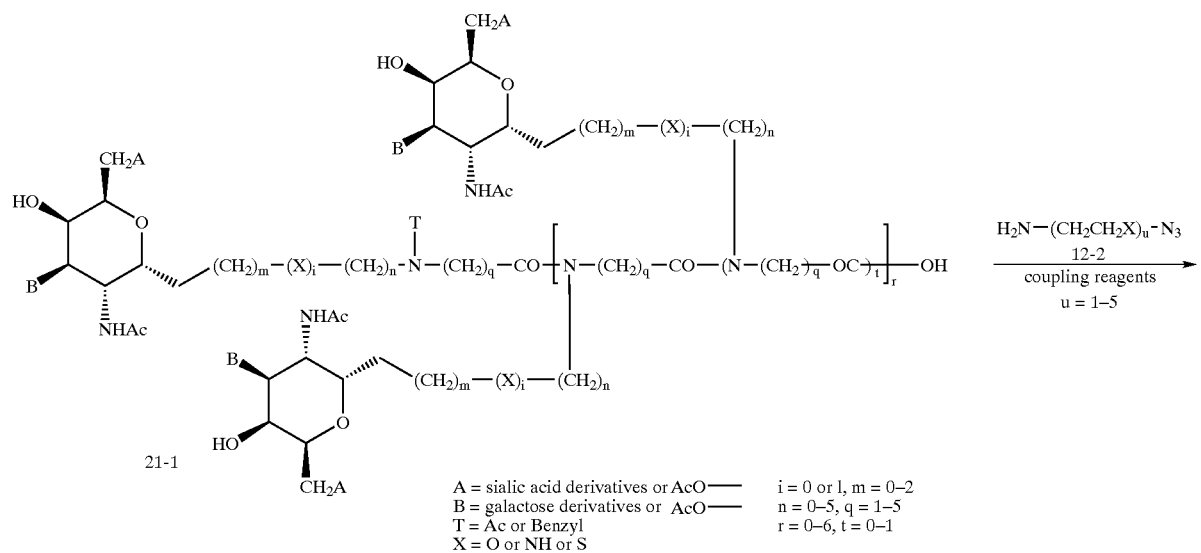
A = sialic acid derivatives or AcO—  i = 0 or l, m = 0–2
B = galactose derivatives or AcO—  n = 0–5, q = 1–5
T = Ac or Benzyl  r = 0–6, t = 0–1
X = O or NH or S
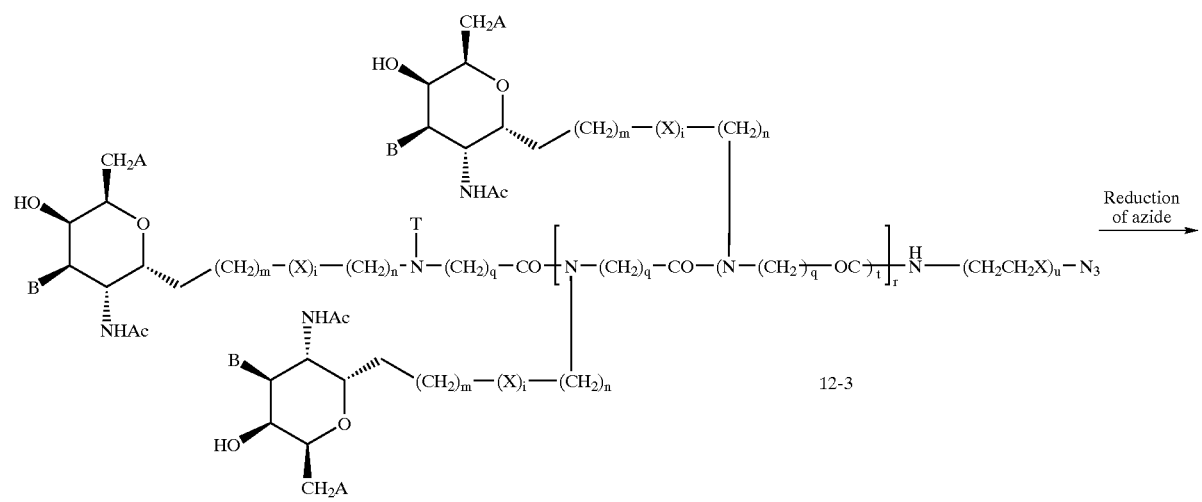
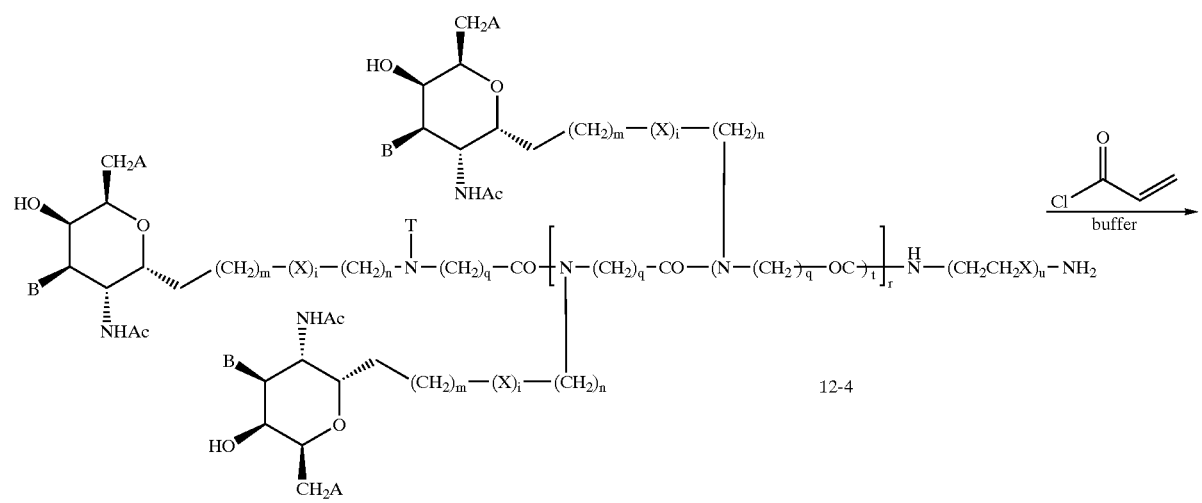

-continued

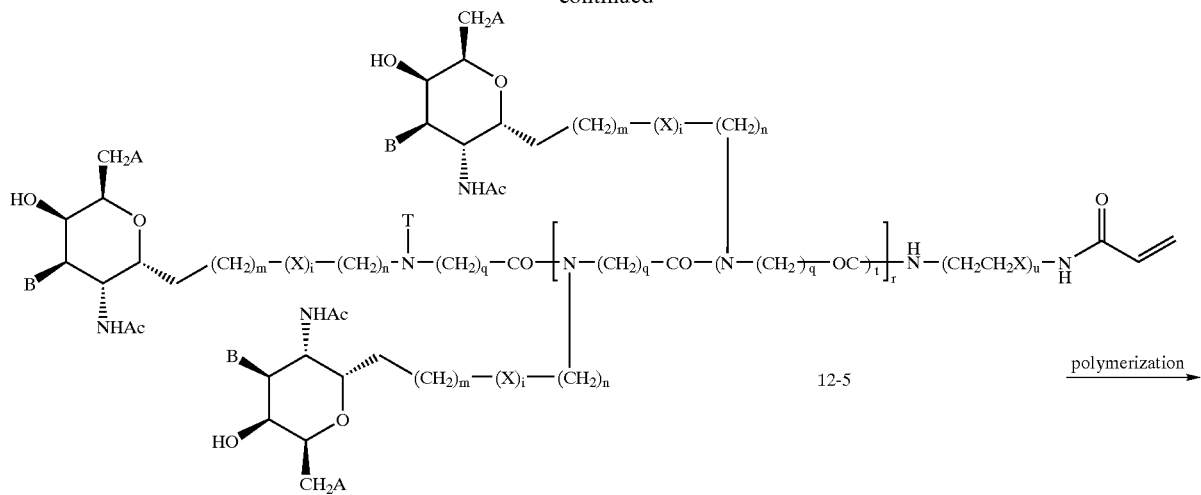

12-5 polymerization →

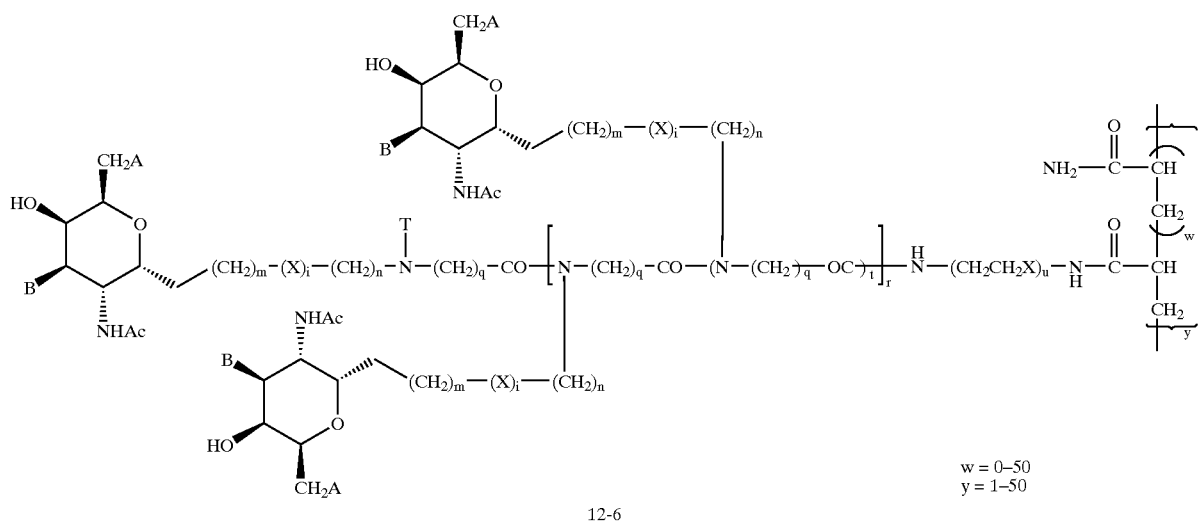

12-6 w = 0–50
y = 1–50

To couple a linker 12-2 with carboxylic acid compound 12-1 afford compound 12-3. Compound 12-3 is reduced to compound 12-4, followed by condensation with acroyl chloride and afforded compound 12-5. Compound 12-5 is converted to compound 12-6 by the method of K. Eklind et al (J.Carbohydrate Chem., 1996, 15, 1161) or J.Domb et al (J.Med.Chem., 2000, 43, 2591). The method of polymerization is not restricted to this method.

(ii) Route 11-b
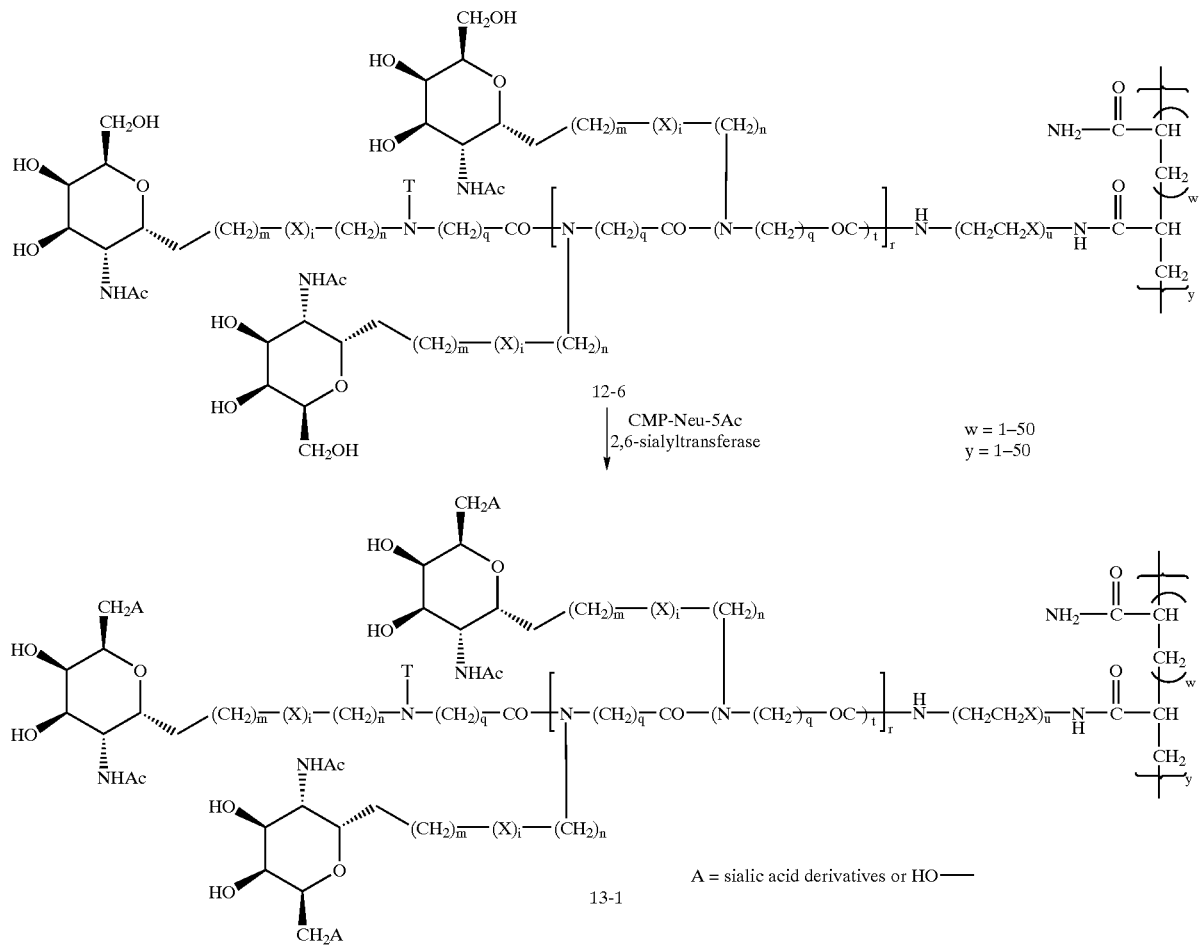
w = 1–50
y = 1–50
A = sialic acid derivatives or HO—
Synthesis of sialic acid derivative 13-1, having a polymer, can be achieved using CMP-Neu-5Ac and sialyltransferase from compound 12-6 (C. Pauison, J. Am. Chem. Soc., 1990, 112, 9308–9309).

(iii) Route 11-c

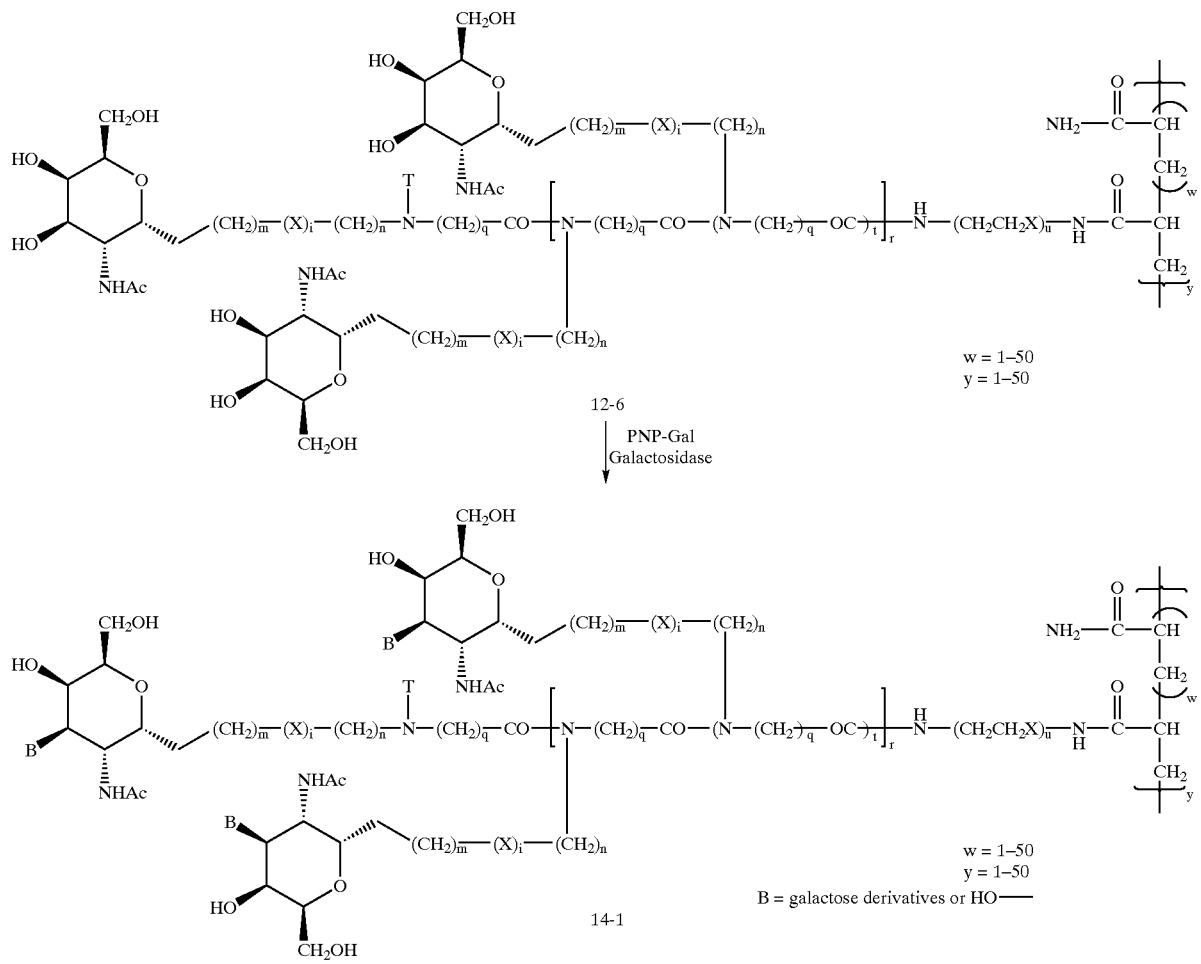

Synthesis of galactose derivative 14-1 can be achieved from compound 12-6 using galactosiase and galactose derivatives PNG-Gal after polymerization (C. Pauison, J. Am. Chem. Soc., 1990, 112, 9308–9309).

The Biological stability for glycosidase such as N-acetyl galactosaminidase was tested using allyl derivatives (11-1, 11-2) by Mark von Itzstein's method (Org. Leyy., 1999, 443–446).

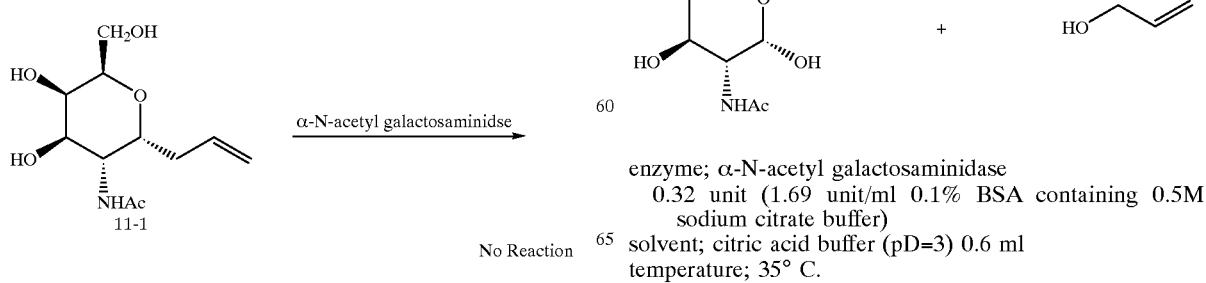

enzyme; α-N-acetyl galactosaminidase
0.32 unit (1.69 unit/ml 0.1% BSA containing 0.5M sodium citrate buffer)
solvent; citric acid buffer (pD=3) 0.6 ml
temperature; 35° C.

procedure; Substrate (2 mg) was disolved in citric acid buffer (0.6 ml) and α-N-acetyl galactosaminidase (0.32 unit) was added. NMR spectrum was determined in every constant time.

Results of this test, Substrate persistence, were shown in table 29.

TABLE 29

| substrate | time | | | | | | | |
|---|---|---|---|---|---|---|---|---|
| | 2 | 4 | 6 | 8 | 10 | 12 | 18 | 24 |
| 11-2 | 89 | 79 | 68 | 57 | 50 | 45 | 40 | 22 |
| 11-1 | 100 | 100 | 100 | 100 | 100 | 100 | 100 | 100 |

From above results, evidently, 78% of O-glycoside linkage allyl ether (11-2) that have was hydrolyzed after 24 h. As it is expected, compound 11-1, replaced ether bond to C—C bond, was unaffected by enzyme, degradation was not observed after 24 h.

This result show the C-glycoside is metabolic and catabolic more stable than O-glycoside.

One or more than two medicinal compounds can be contained compounds that of described general formula (I) in the present invention as active ingredients. And the general formula (1) can be administered to human. And monoclonal antibodies of general formula (I) can be administered to human. The compounds with the invention is concerned may be prepared for administration by any route consistent with their pharmacokinetic propaties. And the compound itself and/or it can be formed injections, powders, granules, tablets, capsules, troches, dry-syrups, lipozome preparations and others. The appropriate dose and dosage times, that of the compound of the present invention, must be determined by the conditions of patient, age, body weight etc.

The compounds are exemplified as follow, but the invention is not limited to these compounds.

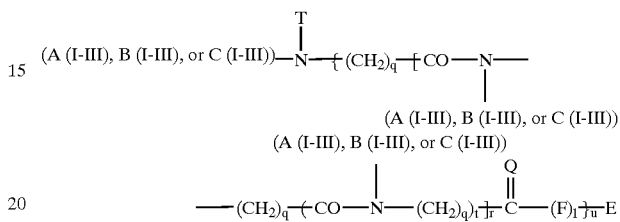

(wherein T, E, F, Q, t, l, and r have above-mentioned meaning; q represents 0 to 5; u is 0 or 1.) A (I), A (II), A (III), B (I), B (II), B (III), C (I), C (II), and C (III) in above equation and table 1–28 were shown in bellow aquation

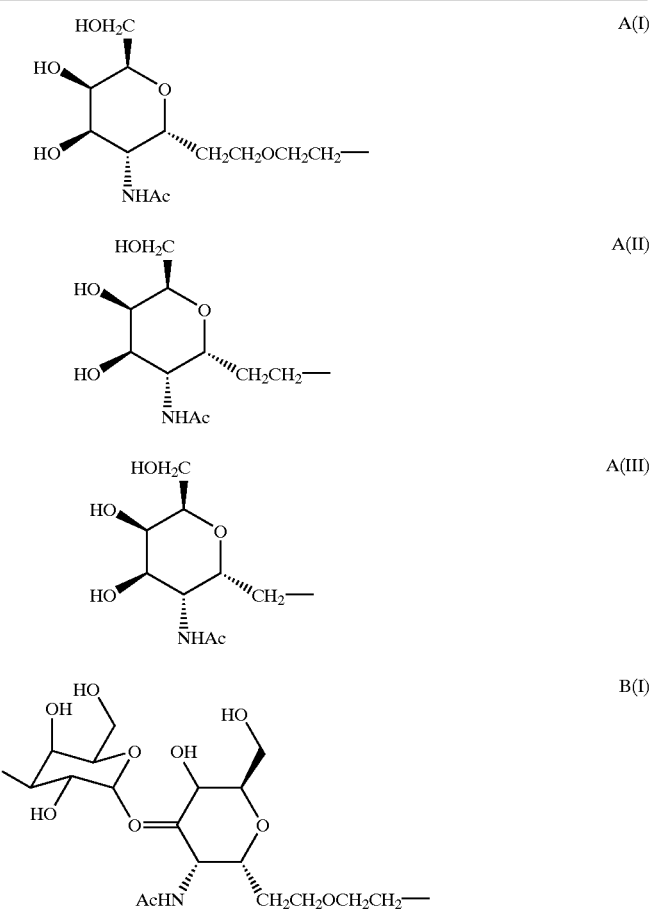

-continued
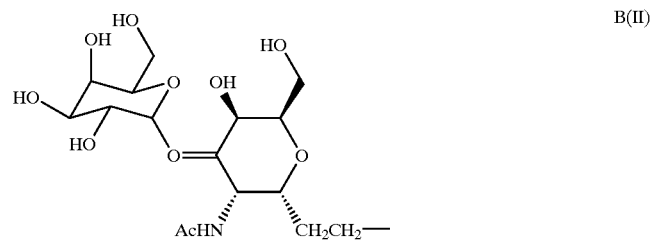 B(II)
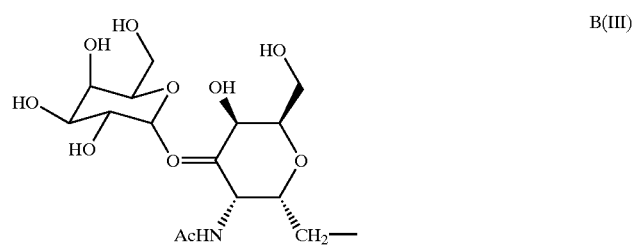 B(III)
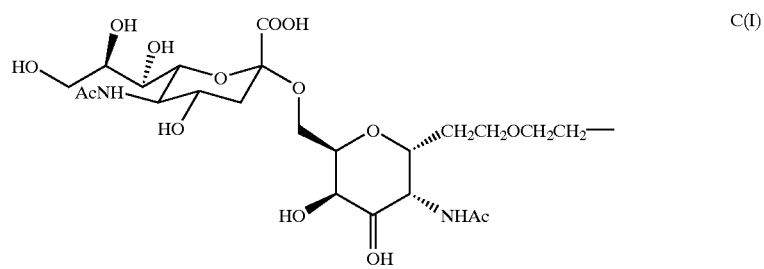 C(I)
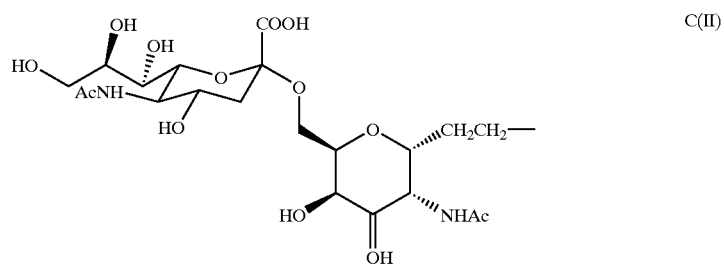 C(II)
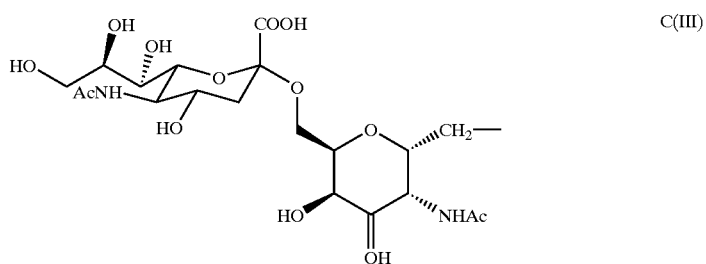 C(III)
R-HN-KLH
| Number | R |
|---|---|
| 1 | A(I) |
| 2 | B(I) |
| 3 | C(I) |

-continued
4 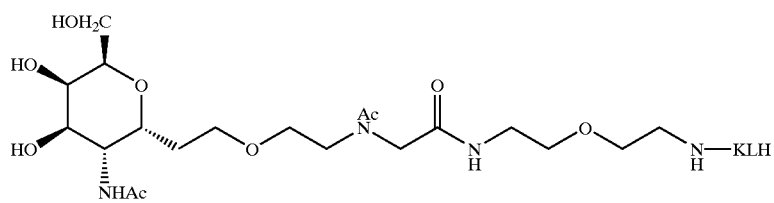
5 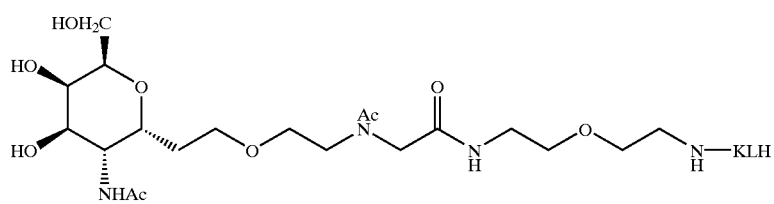
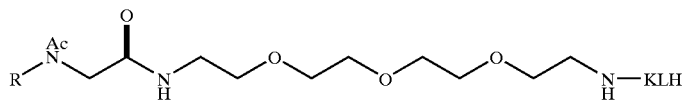
| Number | R |
|---|---|
| 6 | A(I) |
| 7 | A(II) |
| 8 | A(III) |
| 9 | B(I) |
| 10 | B(II) |
| 11 | B(III) |
| 12 | C(I) |
| 13 | C(II) |
| 14 | C(III) |
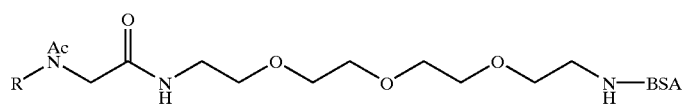
| Number | R |
|---|---|
| 15 | A(I) |
| 16 | A(II) |
| 17 | A(III) |
| 18 | B(I) |
| 19 | B(II) |
| 20 | B(III) |
| 21 | C(I) |
| 22 | C(II) |
| 23 | C(III) |
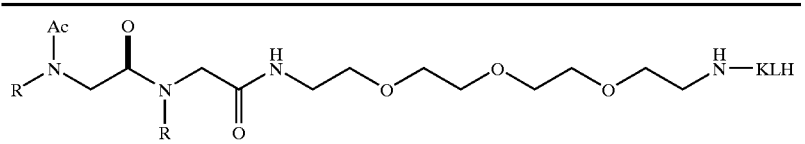
| Number | R |
|---|---|
| 15 | A(I) |
| 16 | A(II) |

-continued
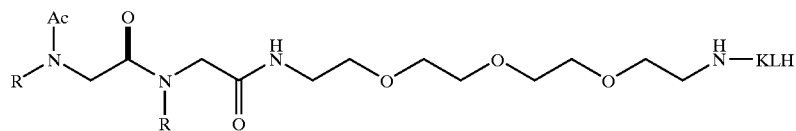
| Number | R |
|---|---|
| 17 | A(III) |
| 18 | B(I) |
| 19 | B(II) |
| 20 | B(III) |
| 21 | C(I) |
| 22 | C(II) |
| 23 | C(III) |
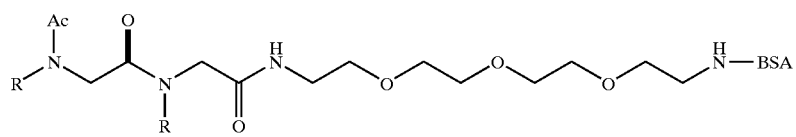
| Number | R |
|---|---|
| 24 | A(I) |
| 25 | A(II) |
| 26 | A(III) |
| 27 | B(I) |
| 28 | B(II) |
| 29 | B(III) |
| 30 | C(I) |
| 31 | C(II) |
| 32 | C(III) |
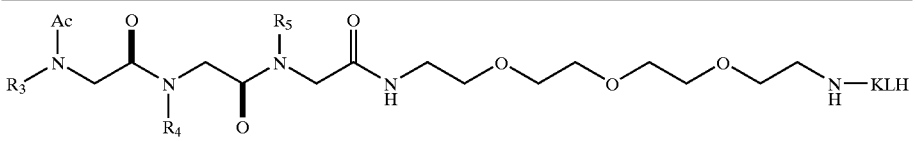
| Number | $R_3$ | $R_4$ | $R_5$ |
|---|---|---|---|
| 33 | A(I) | A(I) | A(I) |
| 34 | A(II) | A(II) | A(II) |
| 35 | A(III) | A(III) | A(III) |
| 36 | B(I) | B(I) | B(I) |
| 37 | B(II) | B(II) | B(II) |
| 38 | B(III) | B(III) | B(III) |
| 39 | C(I) | C(I) | C(I) |
| 40 | C(II) | C(II) | C(II) |
| 41 | C(III) | C(III) | C(III) |
| 42 | A(II) | B(II) | A(II) |
| 43 | B(II) | A(II) | B(II) |
| 44 | A(II) | C(II) | A(II) |
| 45 | C(II) | A(II) | C(II) |
| 46 | B(II) | C(II) | B(II) |
| 47 | C(II) | B(II) | C(II) |
| 48 | A(II) | B(II) | C(II) |

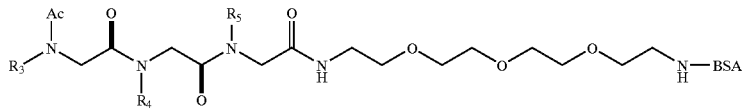
| Number | R₃ | R₄ | R₅ |
| --- | --- | --- | --- |
| 49 | A(I) | A(I) | A(I) |
| 50 | A(II) | A(II) | A(II) |
| 51 | A(III) | A(III) | A(III) |
| 52 | B(I) | B(I) | B(I) |
| 53 | B(II) | B(II) | B(II) |
| 54 | B(III) | B(III) | B(III) |
| 55 | C(I) | C(I) | C(I) |
| 56 | C(II) | C(II) | C(II) |
| 57 | C(III) | C(III) | C(III) |
| 58 | A(II) | B(II) | A(II) |
| 59 | B(II) | A(II) | B(II) |
| 60 | A(II) | C(II) | A(II) |
| 61 | C(II) | A(II) | C(II) |
| 62 | B(II) | C(II) | B(II) |
| 63 | C(II) | B(II) | C(II) |
| 64 | A(II) | B(II) | C(II) |
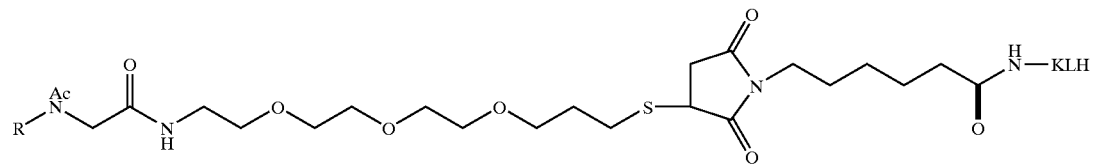
| Number | R |
| --- | --- |
| 65 | A(I) |
| 66 | A(II) |
| 67 | A(III) |
| 68 | B(I) |
| 69 | B(II) |
| 70 | B(III) |
| 71 | C(I) |
| 72 | C(II) |
| 73 | C(III) |
| Number | R |
| --- | --- |
| 74 | A(I) |
| 75 | A(II) |
| 76 | A(III) |
| 77 | B(I) |
| 78 | B(II) |
| 79 | B(III) |
| 80 | C(I) |
| 81 | C(II) |
| 82 | C(III |

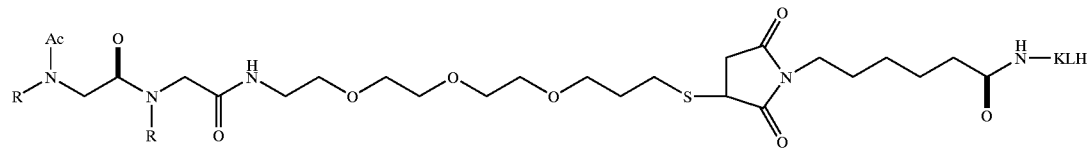
| Number | R |
|---|---|
| 83 | A(I) |
| 84 | A(II) |
| 85 | A(III) |
| 86 | B(I) |
| 87 | B(II) |
| 88 | B(III) |
| 89 | C(I) |
| 90 | C(II) |
| 91 | C(III) |
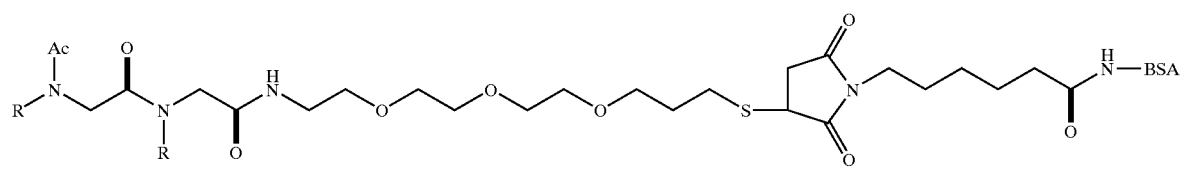
| Number | R |
|---|---|
| 92 | A(I) |
| 93 | A(II) |
| 94 | A(III) |
| 95 | B(I) |
| 96 | B(II) |
| 97 | B(III) |
| 98 | C(I) |
| 99 | C(II) |
| 100 | C(III) |
| Number | $R_3$ | $R_4$ | $R_5$ |
|---|---|---|---|
| 101 | A(I) | A(I) | A(I) |
| 102 | A(II) | A(II) | A(II) |
| 103 | A(III) | A(III) | A(III) |
| 104 | B(I) | B(I) | B(I) |
| 105 | B(II) | B(II) | B(II) |
| 106 | B(III) | B(III) | B(III) |
| 107 | C(I) | C(I) | C(I) |
| 108 | C(II) | C(II) | C(II) |
| 109 | C(III) | C(III) | C(III) |
| 110 | A(II) | B(II) | A(II) |
| 111 | B(II) | A(II) | B(II) |
| 112 | A(II) | C(II) | A(II) |
| 113 | C(II) | A(II) | C(II) |
| 114 | B(II) | C(II) | B(II) |
| 115 | C(II) | B(II) | C(II) |
| 116 | A(II) | B(II) | C(II) |

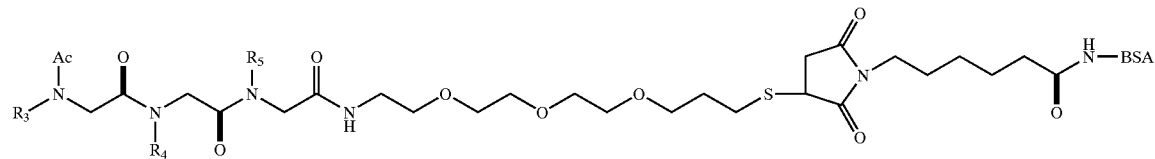
| Number | $R_3$ | $R_4$ | $R_5$ |
|---|---|---|---|
| 117 | A(I) | A(I) | A(I) |
| 118 | A(II) | A(II) | A(II) |
| 119 | A(III) | A(III) | A(III) |
| 120 | B(I) | B(I) | B(I) |
| 121 | B(II) | B(II) | B(II) |
| 122 | B(III) | B(III) | B(III) |
| 123 | C(I) | C(I) | C(I) |
| 124 | C(II) | C(II) | C(II) |
| 125 | C(III) | C(III) | C(III) |
| 126 | A(II) | B(II) | A(II) |
| 127 | B(II) | A(II) | B(II) |
| 128 | A(II) | C(II) | A(II) |
| 129 | C(II) | A(II) | C(II) |
| 130 | B(II) | C(II) | B(II) |
| 131 | C(II) | B(II) | C(II) |
| 132 | A(II) | B(II) | C(II) |
TABLE 15
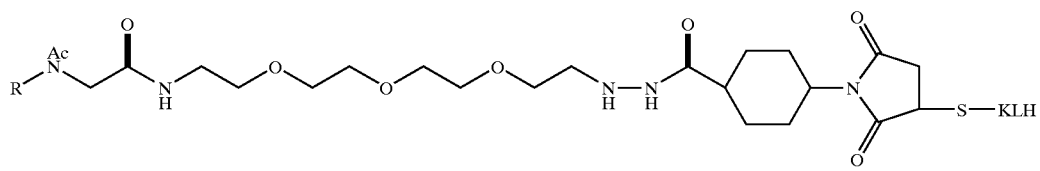
| Number | R |
|---|---|
| 133 | A(I) |
| 134 | A(II) |
| 135 | A(III) |
| 136 | B(I) |
| 137 | B(II) |
| 138 | B(III) |
| 139 | C(I) |
| 140 | C(II) |
| 141 | C(III) |
TABLE 16
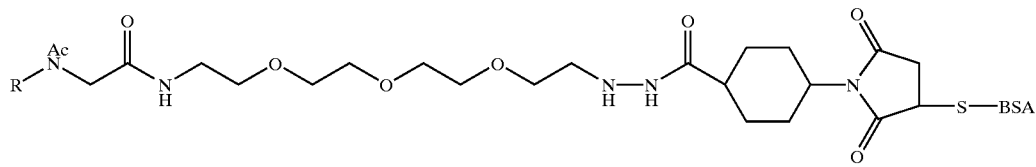
| Number | R |
|---|---|
| 142 | A(I) |
| 143 | A(II) |
| 144 | A(III) |
| 145 | B(I) |
| 146 | B(II) |
| 147 | B(III) |
| 148 | C(I) |
| 149 | C(II) |
| 150 | C(III) |

TABLE 17
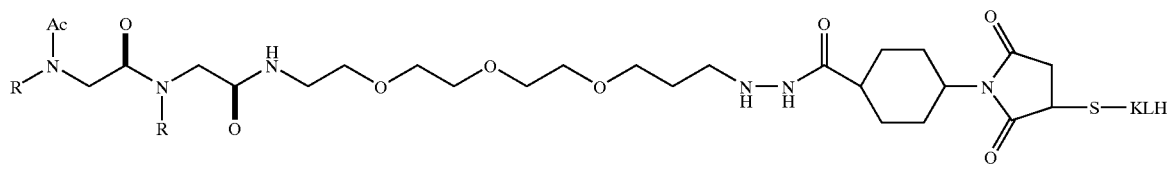
| Number | R |
|---|---|
| 151 | A(I) |
| 152 | A(II) |
| 153 | A(III) |
| 154 | B(I) |
| 155 | B(II) |
| 156 | B(III) |
| 157 | C(I) |
| 158 | C(II) |
| 159 | C(III) |
TABLE 18
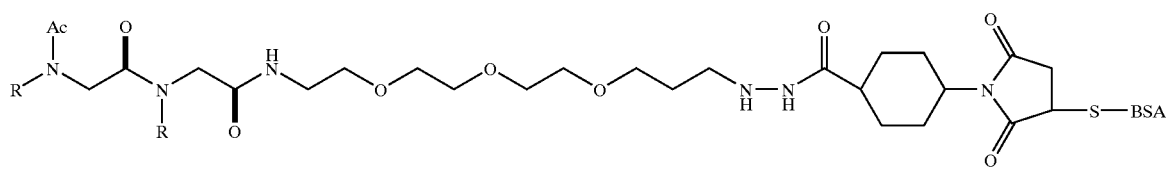
| Number | R |
|---|---|
| 160 | A(I) |
| 161 | A(II) |
| 162 | A(III) |
| 163 | B(I) |
| 164 | B(II) |
| 165 | B(III) |
| 166 | C(I) |
| 167 | C(II) |
| 168 | C(III) |
TABLE 19
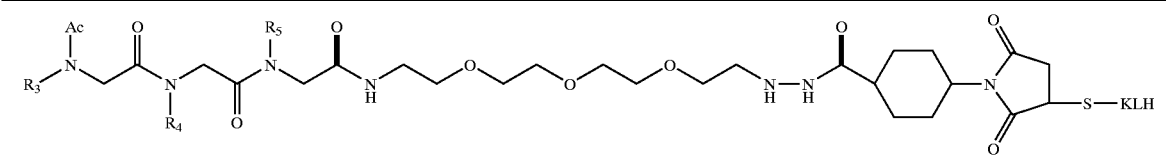
| Number | $R_3$ | $R_4$ | $R_5$ |
|---|---|---|---|
| 169 | A(I) | A(I) | A(I) |
| 170 | A(II) | A(II) | A(II) |
| 171 | A(III) | A(III) | A(III) |
| 172 | B(I) | B(I) | B(I) |
| 173 | B(II) | B(II) | B(II) |
| 174 | B(III) | B(III) | B(III) |
| 175 | C(I) | C(I) | C(I) |
| 176 | C(II) | C(II) | C(II) |
| 177 | C(III) | C(III) | C(III) |
| 178 | A(II) | B(II) | A(II) |
| 179 | B(II) | A(II) | B(II) |
| 180 | A(II) | C(II) | A(II) |
| 181 | C(II) | A(II) | C(II) |
| 182 | B(II) | C(II) | B(II) |
| 183 | C(II) | B(II) | C(II) |
| 184 | A(II) | B(II) | C(II) |

TABLE 20

[Structure diagram: Ac-N(R3)-CH2-C(O)-N(R4)-CH2-C(O)-N(R5)-CH2-C(O)-NH-CH2CH2-O-CH2CH2-O-CH2CH2-O-CH2CH2-NH-NH-C(O)-cyclohexyl-N(succinimide)-S-BSA]

| Number | R₃ | R₄ | R₅ |
| --- | --- | --- | --- |
| 185 | A(I) | A(I) | A(I) |
| 186 | A(II) | A(II) | A(II) |
| 187 | A(III) | A(III) | A(III) |
| 188 | B(I) | B(I) | B(I) |
| 189 | B(II) | B(II) | B(II) |
| 190 | B(III) | B(III) | B(III) |
| 191 | C(I) | C(I) | C(I) |
| 192 | C(II) | C(II) | C(II) |
| 193 | C(III) | C(III) | C(III) |
| 194 | A(II) | B(II) | A(II) |
| 195 | B(II) | A(II) | B(II) |
| 196 | A(II) | C(II) | A(II) |
| 197 | C(II) | A(II) | C(II) |
| 198 | B(II) | C(II) | B(II) |
| 199 | C(II) | B(II) | C(II) |
| 200 | A(II) | B(II) | C(II) |

TABLE 21
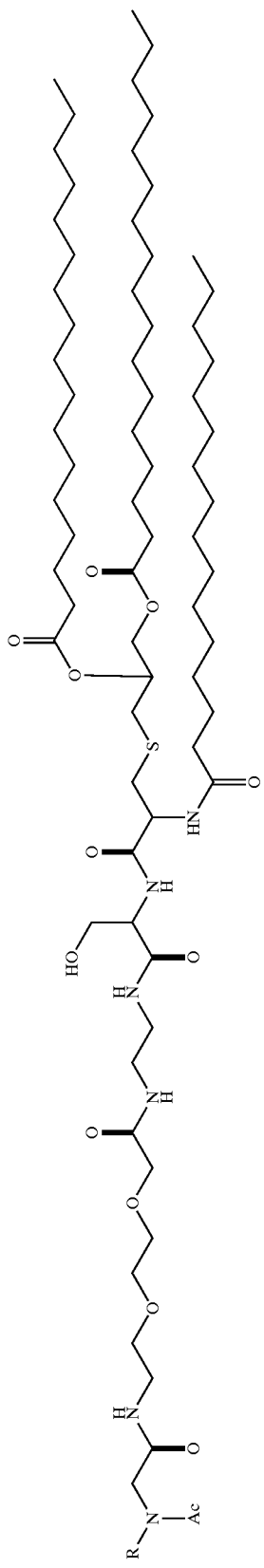
| Number | R |
|---|---|
| 201 | A(I) |
| 202 | A(II) |
| 203 | A(III) |
| 204 | B(I) |
| 205 | B(II) |
| 206 | B(III) |
| 207 | C(I) |
| 208 | C(II) |
| 209 | C(III) |

TABLE 22
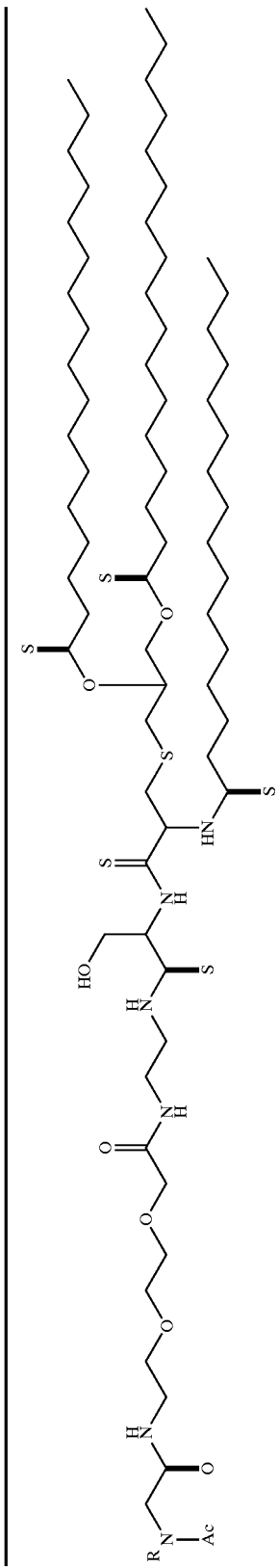
| Number | R |
|---|---|
| 210 | A(I) |
| 211 | A(II) |
| 212 | A(III) |
| 213 | B(I) |
| 214 | B(II) |
| 215 | B(III) |
| 216 | C(I) |
| 217 | C(II) |
| 218 | C(III) |

TABLE 23
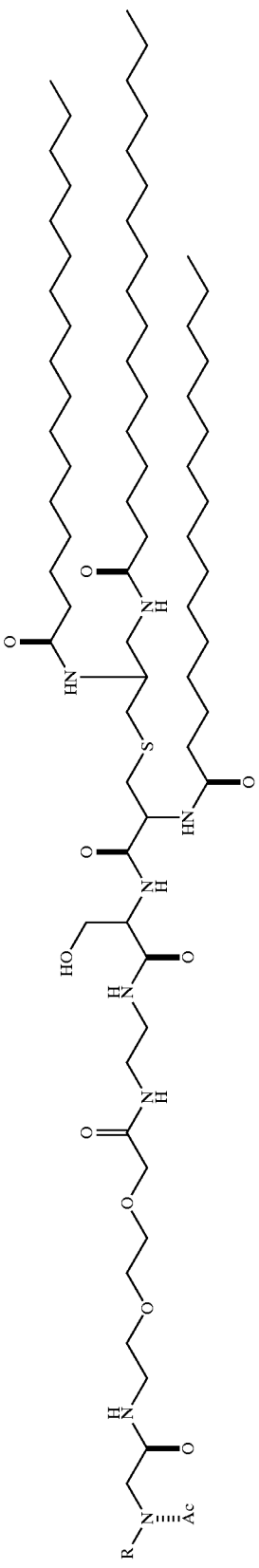
| Number | R |
|---|---|
| 219 | A(I) |
| 220 | A(II) |
| 221 | A(III) |
| 222 | B(I) |
| 223 | B(II) |
| 224 | B(III) |
| 225 | C(I) |
| 226 | C(II) |
| 227 | C(III) |

TABLE 24
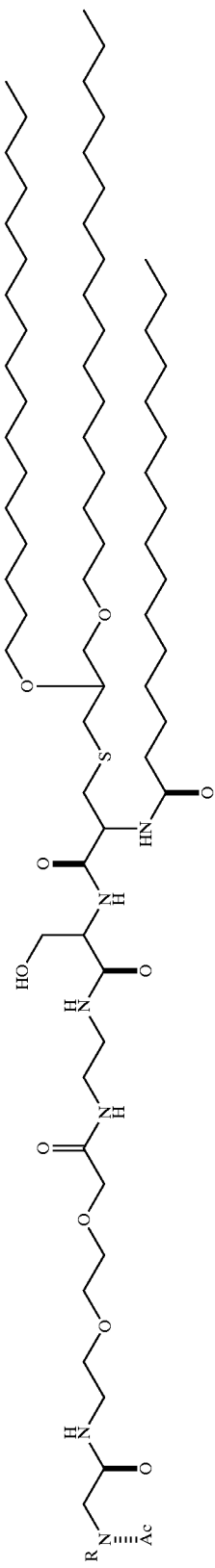
| Number | R |
|--------|------|
| 228 | A(I) |
| 229 | A(II) |
| 230 | A(III) |
| 231 | B(I) |
| 232 | B(II) |
| 233 | B(III) |
| 234 | C(I) |
| 235 | C(II) |
| 236 | C(III) |

TABLE 25
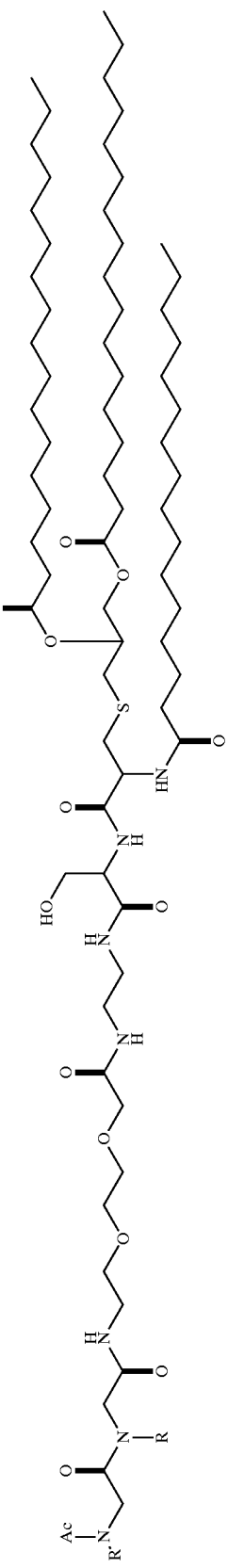
| Number | R |
|---|---|
| 237 | A(I) |
| 238 | A(II) |
| 239 | A(III) |
| 240 | B(I) |
| 241 | B(II) |
| 242 | B(III) |
| 243 | C(I) |
| 244 | C(II) |
| 245 | C(III) |

TABLE 26
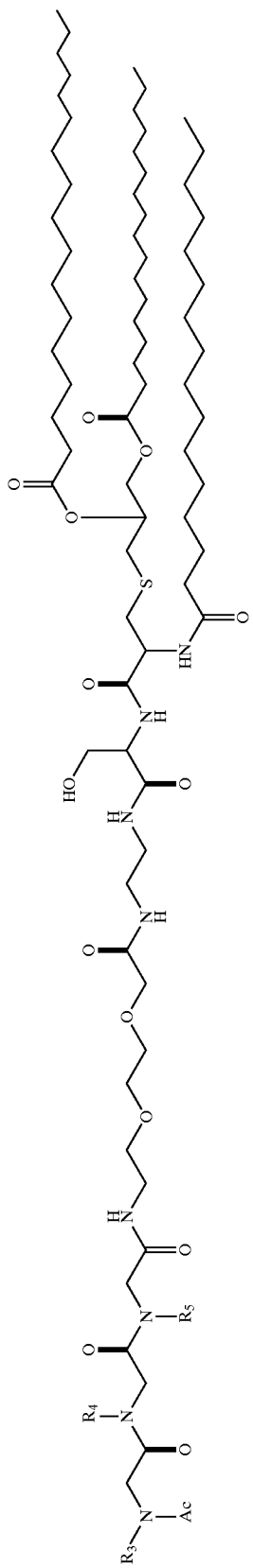
| Number | R₃ | R₄ | R₅ |
|---|---|---|---|
| 246 | A(I) | A(I) | A(I) |
| 247 | A(II) | A(II) | A(II) |
| 248 | A(III) | A(III) | A(III) |
| 249 | B(I) | B(I) | B(I) |
| 250 | B(II) | B(II) | B(II) |
| 251 | B(III) | B(III) | B(III) |
| 252 | C(I) | C(I) | C(I) |
| 253 | C(II) | C(II) | C(II) |
| 254 | C(III) | C(III) | C(III) |
| 255 | A(II) | B(II) | A(II) |
| 256 | B(II) | A(II) | B(II) |
| 257 | C(II) | C(II) | A(II) |
| 258 | B(II) | A(II) | C(II) |
| 259 | C(II) | C(II) | B(II) |
| 260 | A(II) | B(II) | C(II) |
| 261 | B(II) | B(II) | C(II) |

TABLE 27

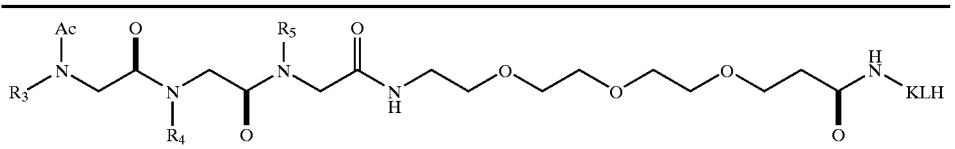

| Number | $R_3$ | $R_4$ | $R_5$ |
| --- | --- | --- | --- |
| 262 | A(I) | A(I) | A(I) |
| 263 | A(II) | A(II) | A(II) |
| 264 | A(III) | A(III) | A(III) |
| 265 | B(I) | B(I) | B(I) |
| 266 | B(II) | B(II) | B(II) |
| 267 | B(III) | B(III) | B(III) |
| 268 | C(I) | C(I) | C(I) |
| 269 | C(II) | C(II) | C(II) |
| 270 | C(III) | C(III) | C(III) |
| 271 | A(II) | B(II) | A(II) |
| 272 | B(II) | A(II) | B(II) |
| 273 | A(II) | C(II) | A(II) |
| 274 | C(II) | A(II) | C(II) |
| 275 | B(II) | C(II) | B(II) |
| 276 | C(II) | B(II) | C(II) |
| 277 | A(II) | B(II) | C(II) |

TABLE 28

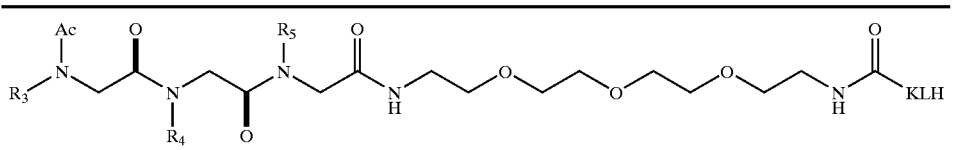

| Number | $R_3$ | $R_4$ | $R_5$ |
| --- | --- | --- | --- |
| 278 | A(I) | A(I) | A(I) |
| 279 | A(II) | A(II) | A(II) |
| 280 | A(III) | A(III) | A(III) |
| 281 | B(I) | B(I) | B(I) |
| 282 | B(II) | B(II) | B(II) |
| 283 | B(III) | B(III) | B(III) |
| 284 | C(I) | C(I) | C(I) |
| 285 | C(II) | C(II) | C(II) |
| 286 | C(III) | C(III) | C(III) |
| 287 | A(II) | B(II) | A(II) |
| 288 | B(II) | A(II) | B(II) |
| 289 | A(II) | C(II) | A(II) |
| 290 | C(II) | A(II) | C(II) |
| 291 | B(II) | C(II) | B(II) |
| 292 | C(II) | B(II) | C(II) |
| 293 | A(II) | B(II) | C(II) |

Pharmacological Experiment

Immunization and Antiserum Preparation

Vaccine used to immunize were prepared as below. Glycoproteinic antigen (ex. 1 mg) suspended in phosphate buffered saline (ex. 1 mg) were mixed with equivalent volume of adjuvant (ex. freund complete adjuvant, and BCG etc.). Female BALB/c mice (6 weeks of age) were subcutaneously immunized with 200 µl/mouse of vaccine. Mice were injected on days 0, 14, 28, and bled 1 week after the 3rd immunization. Antiserum (−) was obtained from the blood centrifused at 1,200×g for 20 min.

Measurement of Antibody Titer.

Microtiter 96-well plate were coated with Tn antigen. IgG and IgM antibody titers were measured by ELISA with horse anti-mouse IgG antibody and anti-mouse IgM antibody, respectively, as second antibody. Human colon carcinoma cell line LS-174T cells cultured in microtiter 96-well plates, and were imorbilized with methanol. As described, IgG and IgM antibody titers were measured by ELISA. Effects of each compounds described below on antibody titer were evaluated by this assay.

1 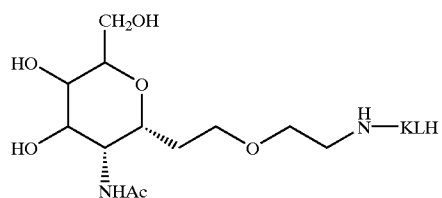
3 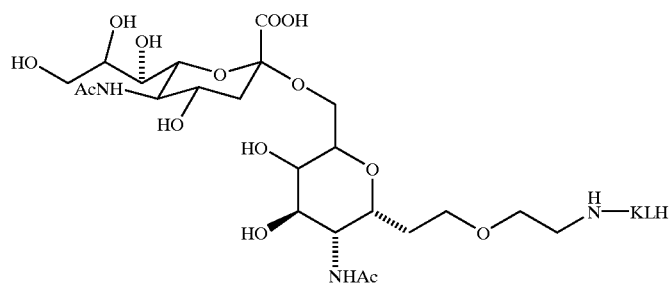
4 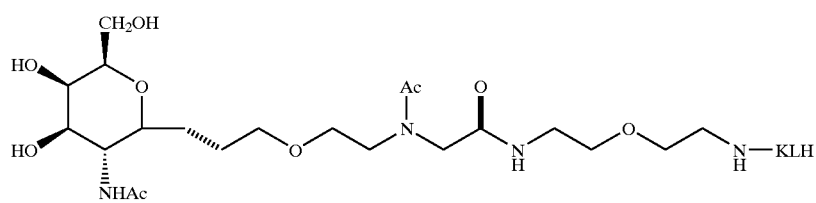
5 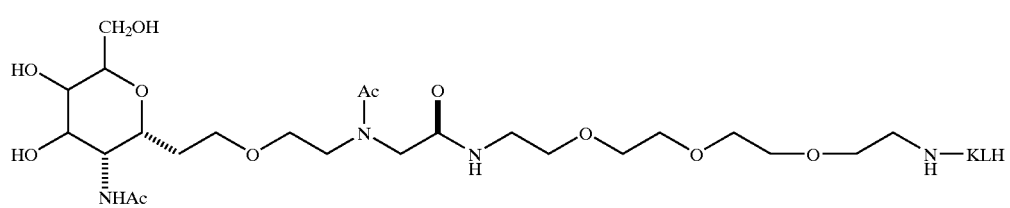
6 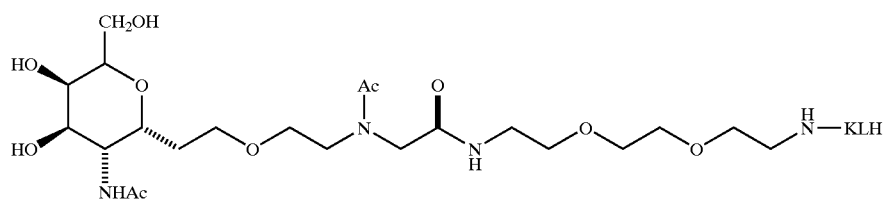
12 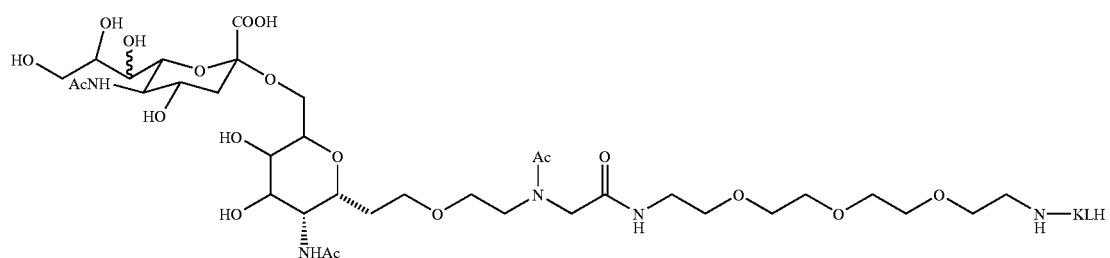

15
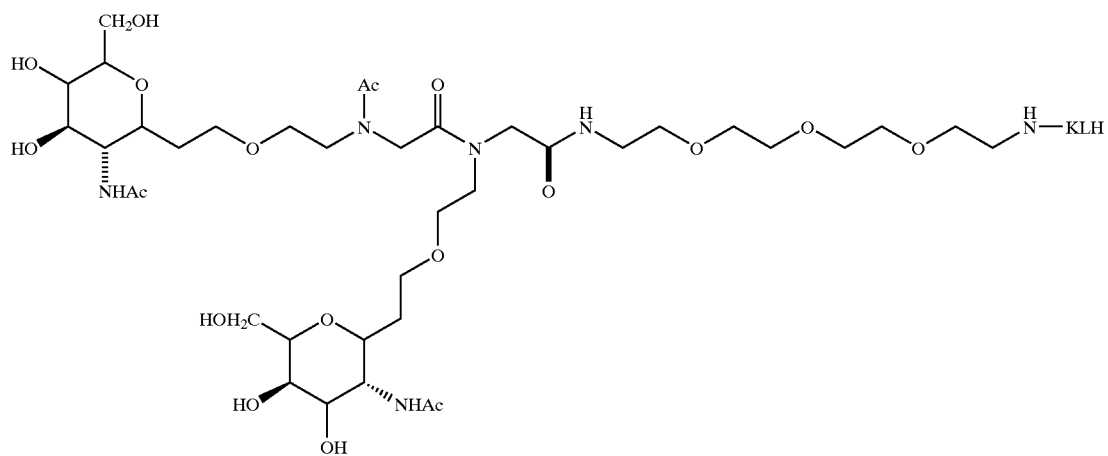
33(a)
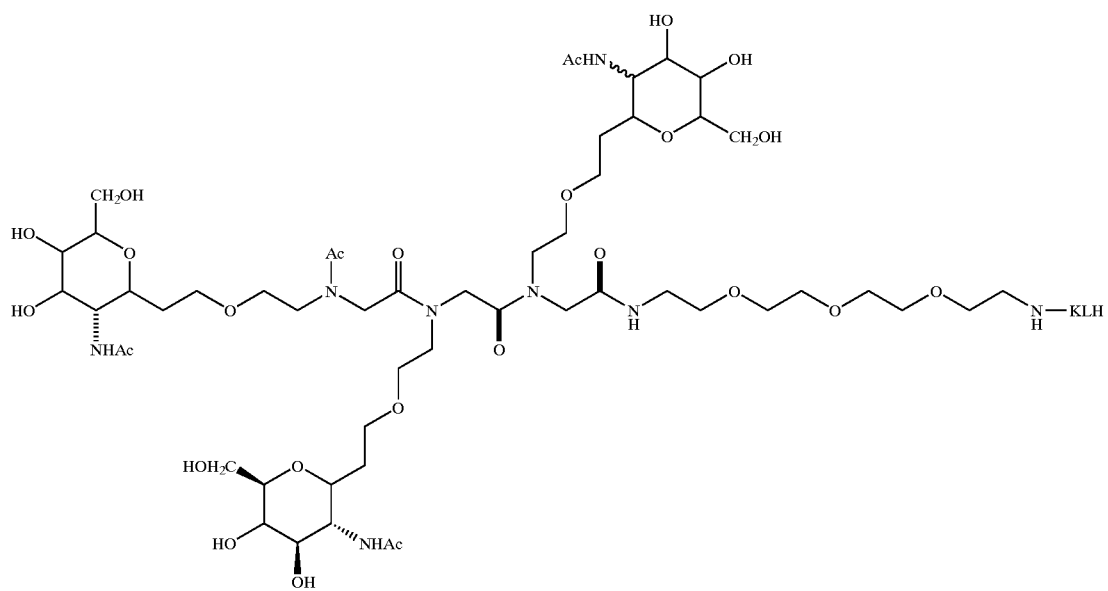
33(b)
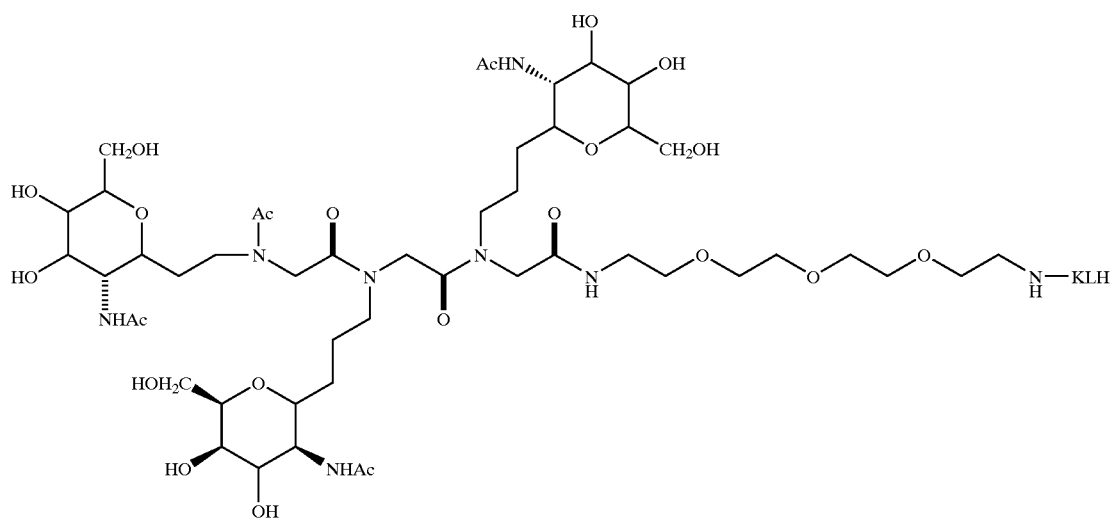

-continued

33(c)

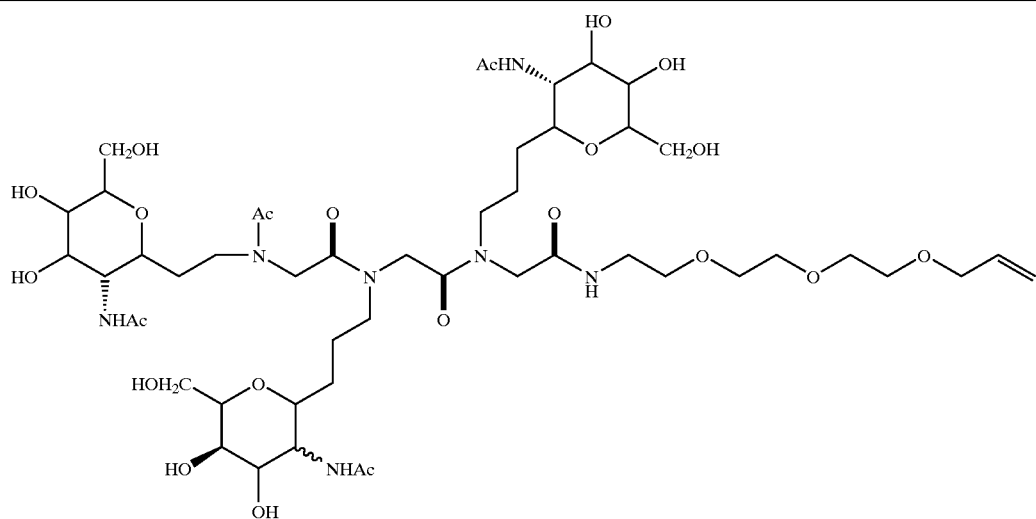

IgG and IgM antibody titer (against Tn antigen) in mouse serum after vaccination were shown in table 30 and 31 respectively. IgG and IgM antibody titer (against LS-174T cell) after vaccination were shown in table 32.

TABLE 30

| Number | dose | Adjuvant | 1st immunization IgG | 2nd immunization IgG | 3rd immunization IgG |
|---|---|---|---|---|---|
| 1 | 10 μg | BCG | Not tested | Not Tested | 2667 ± 3233 |
| 3 | 10 μg | BCG | 800 ± 0 | 2160 ± 1431 | 4960 ± 4879 |
| 5 | 10 μg | BCG | Not tested | Not tested | 2640 ± 1252 |
| 6 | 10 μg | BCG | 200 ± 200 | 1600 ± 980 | 7680 ± 10207 |
| 12 | 1 μg | BCG | 600 ± 283 | 1920 ± 1213 | 7680 ± 10207 |
| 15 | 10 μg | BCG | 560 ± 358 | 2080 ± 1073 | 6400 ± 5879 |
| 33(a) | 1 μg | BCG | 200 ± 346 | 1760 ± 1315 | 6880 ± 10516 |
| 33(b) | 10 μg | BCG | 240 ± 220 | 1920 ± 720 | 7700 ± 3320 |
| 33(c) | 10 μg | BCG | 1040 ± 780 | 1760 ± 1320 | 4840 ± 5010 |

TABLE 31

| Number | dose | Adjuvant | 1st immunization IgM | 2nd immunization IgM | 3rd immunization IgM |
|---|---|---|---|---|---|
| 1 | 10 μg | BCG | Not tested | Not tested | 1333 ± 462 |
| 3 | 10 μg | BCG | 40 ± 89 | 1280 ± 1213 | 2920 ± 3257 |
| 5 | 10 μg | BCG | Not tested | Not tested | 1040 ± 537 |
| 6 | 10 μg | BCG | 0 ± 0 | 360 ± 297 | 600 ± 616 |
| 12 | 1 μg | BCG | 160 ± 358 | 2880 ± 716 | 1600 ± 980 |
| 15 | 10 μg | BCG | 100 ± 173 | 960 ± 358 | 5140 ± 2817 |
| 33 | 1 μg | BCG | 0 ± 0 | 660 ± 313 | 1860 ± 2617 |
| 33(b) | 10 μg | BCG | 100 ± 100 | 1280 ± 440 | 1960 ± 2530 |
| 33(c) | 10 μg | BCG | 10400 ± 5400 | 3400 ± 130 | 400 ± 250 |

TABLE 32

| Number | dose | Adjuvant | IgG | IgM |
|---|---|---|---|---|
| 3 | 10 μg | BCG | 2400 ± 1131 | 1520 ± 1073 |
| 5 | 10 μg | BCG | 800 ± 0 | 2160 ± 1431 |
| 5 | 10 μg | BCG | 640 ± 590 | 1120 ± 438 |
| 6 | 10 μg | BCG | 1120 ± 1242 | 1200 ± 560 |
| 33(a) | 1 μg | BCG | 1520 ± 1073 | 1440 ± 358 |

Antibody Depended Cell Mediated Cytotoxic Response (ADCC)

LS-174T cells used as target cells and mononuclear cells from peripheral blood in human were used as effector cells. The target cells were seeded into microtiter 96-well plate ($1\times10^3$ cells/well/50 μl), and were added 0.5 μCi/well of $^{51}CrCl_2$, the cells supernatants were harvested and counted in a gamma counter. The cytotoxicity was calculated as the persentage of releasable counts subtracting the spontaneous release. The results were shown in Table 33.

TABLE 33

| Dilution | cpm/1000 cells |
|---|---|
| 200 | 913 |
| 400 | 685 |
| 800 | 318 |
| 1600 | 281 |
| 3200 | 103 |
| 6400 | 46 |

Purified Carrier Protein

Keyhole limpet hemocyanin (KLH, CHEMICONINTERNATIONAL INC.) was purified by the previously published method. KLH (500 mg) was suspended in 50 ml phosphate buffered saline (PBS(-)) and centrifuged at 1,200×g for 20 min. Resulted supernatant was centrifuged at 43,000×g for 15 min. Resulted sediment was suspended in PBS(-) and further centrifuged at 43,000×g for 15 min and resulted sediment was used as carrier protein.

Immunization

C-linked Tn-KLH conjugate or C-linked sTn-KLH conjugate (1 to 10 μg) were immunized subcutaneously to female BALB/c mice with BCG(50 μg) 3 times at two weeks interval. One week after the last immunization, mice were anesthetized and bloods were collected from abdominal vein. Antisera were separated by centrifugation, and IgG or IgM antibody titers against gp120 were assayed by ELISA. The titer was defined as the highest dilution yielding an absorbance of greater over that of normal sera. The results were shown in Table 34.

TABLE 34

| Number | IgG | IgM |
|---|---|---|
| 3 | 12,800 | 6,400 |
| 5 | 12,800 | 12,800 |
| 12 | 12,800 | 6,400 |
| 15 | 6,400 | 12,800 |
| 33 | 6,400 | 6,400 |

Our results also shows the potent immunogenicity of metabolic and catabolic stable "C-glycopeptoid" with or even without carrier protein. On other hand, Danishefsky's team reported the O-Tn, O-STn, O-TF antigens have less potent immunogenicity themselves, but attached to carrier proteins such as KLH. (S. J. Danishefsky et al, 1998, 120, 1427–14285.)

We firstely showed the concept and efficacy of using "C-glycopeptoid" for the promising immunotherapy of cancer and HIV.

EXAMPLE

The following Examples are provide only for the purpose of the preparation of the compounds and not restrict to the disclosed invention.

Referencial Example 1

The preparation of 2-Acetylamino-1,3,4-tri-O-acetyl-6-O-triphenylmethyl-2-deoxy-α-D-glucopyranose (compound 1a-2)

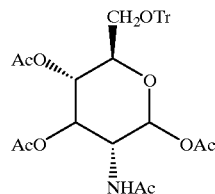

A suspension of N-acetylglucosamine (200 g, 0.9 mol) and trityl chloride (250 g, 0.9 mol) in pyridine (363 ml) was heated to 85° C. After the suspension was dissolved, acetic anhydride (280 ml, 2.97 mol) was added and stirred for 23 h at room temperature. The reaction mixture was slowly poured into ice water-acetic acid. The mixture was stirred for 3 h and the resulting precipitate was collected, followed by washing with water. 400 g (75%) of the objective compound was obtained.

MS (m/z): 590, 531, 452, 243, 165.

IR (cm$^{-1}$) neat: 3364, 1749, 1656, 1218.

$^1$H-NMR (CDCl$_3$) δ: 3.02 (1H, dd, J=10.8, 3.9 Hz), 3.27 (1H, dd, J=10.3, 2.0 Hz), 3.87 (1H, ddd, J=9.3, 2.0, 2.0 Hz), 4.54 (1H, ddd, J=11.2, 9.3, 3.9 Hz), 5.17 (1H, dd, J=11.2, 9.8 Hz), 5.35 (1H, dd, J=9.8, 9.8 Hz), 5.53 (1H, d, J=8.8 Hz), 6.29 (1H, d, J=3.4 Hz), 7.31–7.17 (9H, m), 7.41–7.43 (6H, m).

Referencial Example 2

The preparation of 2-acetylamino-1,3,4-tri-O-acetyl-2-deoxy-α-D-glucopyranose (compound 1a-3)

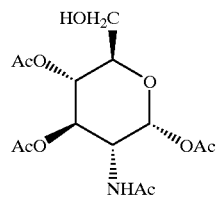

The trityl compound (168 g) obtained from the above mentioned Referencial Example 1 was dissolved in diethylether (420 ml), then formic acid (420 ml) was added at room temperature and the mixture was stirred for 7 h. After the reaction was finished, the reaction mixture was poured into ice cold water and neutralized by NaHCO$_3$, followed by removal of diethylether, and the resulting precipitate was filtrated. The filtrate was extracted with chloroform. After drying (Na$_2$SO$_4$), the solvent was removed under reduced pressure. 46 g (46%) of the objective alcohol was obtained.

MS (m/z): 347, 304, 228, 114.

IR (cm$^{-1}$) neat: 3280, 3076, 1749, 1665, 1221.

$^1$H-NMR (CDCl$_3$) δ: 1.91 (3H, s), 2.04 (3H, s), 2.16 (3H, s), 3.55 (1H, dd, J=12.8, 4.4 Hz), 3.66 (1H, dd, J=12.8, 2.2

Hz), 3.78 (1H, ddd, J=10.1, 4.3, 2.2 Hz), 4.43 (1H, ddd, J=10.9, 9.0, 3.6 Hz), 5.14 (1H, t, J=9.7 Hz), 5.25 (1H, dd, J=10.8, 9.6 Hz), 5.76 (1H, d, J=9.0 Hz), 6.15 (1H, d, J=3.6 Hz).

Referencial Example 3

The preparation of 2-acetylamino-1,3,6-tri-O-acetyl-2-deoxy-α-D-glucopyranose (compound 1a-4)

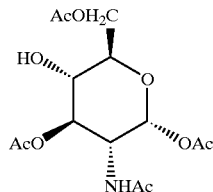

To a solution of the primary alcohol compound (81 g, 0.23 mol) obtained from the above mentioned Referencial Example 2 in toluene (1600 ml) was added acetic acid (16 ml) and the mixture was stirred at 80° C. for 15 h. After the reaction was completed, the reaction mixture was concentrated under reduced pressure. The redsidue was purified by silicagel column chromatography (AcOEt). 99 g (58%) of the objective compound was obtained as a colorless oil.

MS (m/z): 347, 304, 262, 228, 114.

IR (cm$^{-1}$) neat: 3370, 3010, 1737, 1659, 1230.

$^1$H-NMR (CDCl$_3$) δ: 1.93 (3H, s), 2.13 (3H, s), 2.17 (3H, s), 3.70 (1H, dd, J=9.8, 3.5 Hz), 3.84 (2H, d, J=3.5 Hz), 3.90 (1H, dd, J=9.8, 9.2 Hz), 4.30 (1H, ddd, J=11.1, 9.0, 3.7 Hz), 5.12 (1H, dd, J=11.1, 9.2 Hz), 5.71 (1H, d, J=9.0 Hz), 6.11 (1H, d, J=3.6 Hz).

Referencial Example 4

The preparation of 2-acetylamino-1,3,6-tri-O-acetyl-4-O-trifluoromethanesulfonyl-2-deoxy-α-D-glucopyranose
(compound 1a-5)

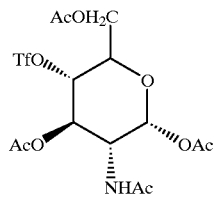

The alcohol compound (5.0 g, 14.3 mmol) obtained from the above mentioned Referencial Example 3 was dissolved in dichloromethane (50 ml) and added pyridine (5 ml). The solution was cooled to −40° C., then triflic anhydride (3.1 ml 18.7 mmol) was added dropwise to the mixture. After stirring for 2 h, the reaction mixture was poured into ice cold water and extracted with dichloromethane. The organic layer was washed with 10% HCl and dried (Na$_2$SO$_4$). The solvent was removed under reduced pressure. 7.83 g of the objective compound was obtained as a colorless oil.

Referencial Example 5

The preparation of 1-(2-acetylamino-3,4,6-tri-O-acetyl-2-deoxy-α-D-galactopyrano-1-yl)-2-propene (compound 1a-6)

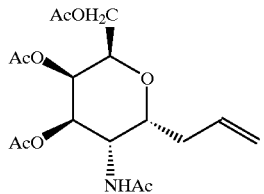

To 2.0 g (9.0 mmol) of N-acetylgalactosamine was slowly added acetyl chloride (4.0 ml) at 0° C. The mixture was stirred for 14 h at room temperature. After the reaction, the mixture was poured into ice cold water and extracted with chloroform. The organic layer was neutralized by satd. NaHCO$_3$, and washed with water and brine. After drying (Na$_2$SO$_4$), the solvent was removed under reduced pressure. 3.3 g of N-acetylamino-1-Chrolo-tri-O-acetyl-2-deoxy-galactosamine was obtained as a colorless oil. To a solution of the obtained compound (3.3 g, 9.0 mmol) in toluene, was added allyltributyltin (8.5 ml) and 2,2'-azobisisobutyronitrile (AIBN) (0.25 g) under argon atmosphere. The reaction mixture was heated to 80° C. and stirred for 6 h. After the reaction was completed, the mixture was cooled to room temperature. The solvent was removed under reduced pressure. The resulting redsidue was purified by silicagel column chromatography (BW-200, AcOEt:n-hexane=4:1). 0.85 g (25.4%) of the oily objective compound was obtained as a colorless oil.

Mass (m/e): 371, 330, 210, 150, 101, 59.

IR (cm$^{-1}$) KBr: 3290, 3071, 1746, 1658, 1020.

$^1$H-NMR(C$_6$D$_6$) δ: 1.47 (3H, s), 1.63 (3H, s), 1.66 (3H, s), 1.67 (3H, s), 1.99 (1H, m), 2.19 (1H, m), 3.94 (1H, m), 4.26 (1H, d,d, J=3, 5 Hz), 4.37 (2H, m), 4.83 (1H, m), 5.00 (2H, m), 5.17 (1H, d, J=7 Hz), 5.43 (1H, t, J=3 Hz), 5.68 (1H, m), 6.19 (1H, S).

Referencial Example 6

The preparation of 1-(2-diacetylamino-3,4,6-tri-O-acetyl-2-deoxy-α-D-galactopyrano-1-yl)-2-propene (compound 1a-9)

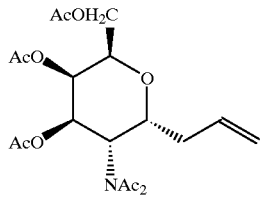

To a solution of the compound (1.5 g, 4.0 mmol) obtained from the above mentioned Referencial Example 5 in iso-propenyl acetate (15 ml) was added p-toluensulfonic acid (20 mg). The reaction mixture was stirred at 55° C. for 42 h. After the mixture was cooled to room temperature, trietlylamine was added and stirred for 15 min. The mixture was concentrated. The residue was purified by silicagel column chromatography (BW-200, AcOEt:n-hexane=1:1). 1.0 g (66%) of the objective diacetate compound was obtained as a colorless oil.

Mass (m/e): 413, 372, 330, 270, 210, 179, 150, 126, 101, 59.

IR (cm$^{-1}$) KBr: 3050, 1749, 1668, 1233, 780

$^1$H-NMR(CDCl$_3$) δ: 1.95 (3H, s), 2.03 (3H, S), 2.16 (3H, s), 2.17 (1H, m), 2.39 (3H, s), 2.75 (1H, m), 4.05 (2H, m), 4.15 (2H, m), 4.61 (1H, d, d, J=4,8 Hz), 5.11 (2H, m), 5.50 (1H, d, J=3 Hz), 5.75 (1H, m), 5.95 (1H, dd, J=3, 11 Hz).

Referencial Example 7

The preparation of 2-(2-acetylamino-3,4,6-tri-O-acetyl-2-deoxy-α-D-galactopyrano-1-yl)-acetaldehyde (compound 1a-10)

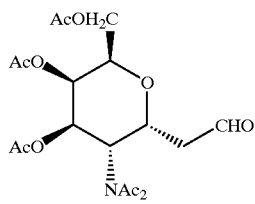

To a solution of the compound (0.74 g, 1.78 mmol) obtained from the above mentioned Referencial Example 6 in tetrahydrofrane (10 ml) was added water (10 ml), NaIO$_4$ (1.9 g, 8.91 mmol) and 4% OsO$_4$ solution under an atmosphere of argon. The mixture was stirried for 4 h at room temperature. After the reaction was completed, the reaction mixture was extracted with ethyl acetate and washed with water and brine. After drying (MgSO$_4$), the solvent was removed under reduced pressure. 0.77 g (98%) of the objective aldehyde compound was obtained as a colorless oil.

IR (cm$^{-1}$) KBr: 1746, 1371, 1230, 1054, 665.

$^1$H-NMR(CDCl$_3$) δ: 1.95 (3H, s), 2.04 (3H, s), 2.16 (3H, s), 2.37 (6H, s), 2.85 (1H, m), 3.17 (1H, dd, J=2,8 Hz), 4.11 (3H, m), 4.75 (2H, m), 5.54 (1H, m), 5.81 (1H, d, d, J=3.5, 11 Hz), 9.67 (1H, s).

Referencial Example 8

The preparation of 2-(2-acetylamino-3,4,6-tri-O-acetyl-2-deoxy-α-D-galactopyrano-1-yl)-ethanol
(compound 1a-11)

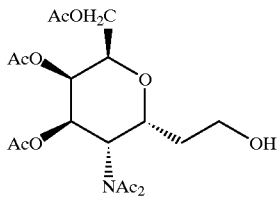

To a solution of the compound (0.77 g, 1.85 mmol) obtained from the above mentioned Referencial Example 7 in methanol (10 ml) was added sodium borohydride (0.1 g, 2.78 mmol) at 0° C. and the mixture was stirred for 10 min. The reaction mixture was poured into satd.NH$_4$Cl and extracted with dichloromethane. The organic layer was washed with water and brine. After drying (MgSO$_4$), the solvent was removed under reduced pressure. The resulting residue was purified by silicagel column chromatography (BW-200, ACOEt:MeOHe=10:1). 0.25 g (36%) of the oily objective compound was obtained as a colorless oil.

Mass (m/e): 357(M$^+$), 316, 238, 183, 141, 101, 59.

IR (cm$^{-1}$) KBr: 1743, 1680, 1398, 1236.

$^1$H-NMR(CDCl$_3$) δ: 1.60 (1H, m), 1.95 (1H, m), 2.00 (3H, s), 2.09 (3H, m), 2.10 (3H, s), 2.12 (3H, s), 3.17 (1H, dd, J=3, 8 Hz), 3.76 (2H, m), 4.05–4.18 (3H, m), 4.42 (3H, m), 5.32 (1H, t, J=3 Hz), 5.73 (1H, d, J=8 Hz).

Referencial Example 9

The preparation of 1-(2-acetylamino-3,4,6-tetra-O-acetyl-2-deoxy-α-D-glucopyrano-1-yl)-2-propene (compound 1b-2)

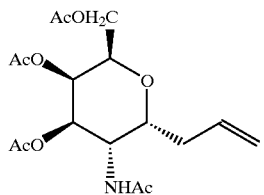

To N-acetylglucosamine 100 g (0.45 mol) was added acetyl chloride (200 ml) at 0° C. and stirred for 23 h. After the reaction, the mixture was extracted with chloroform and the mixture was poured into ice cold water and stirred for 10 min. The organic layer was neutralized by satd. NaHCO$_3$ and dried (Na$_2$SO$_4$). The solvent was removed under reduced pressure. Diethyl ether was added to the residue and the resulting precipitate was collected. 117 g (71%) of 2-acetylamino-1-chloro-3,4,6-tetra-O-acetyl-2-deoxy-α-D-galactose was obtained as a colorless solid. To a solution of the obtained compound (78 g, 0.21 mol) in tetrahydrofuran (400 ml) was added allyltributyltin (198 ml, 0.64 mol) and 2,2'-azobisisobutyronitrile (AIBN) (3.4 g, 0.02 mol). The reaction mixture was heated to 80° C. and stirred for 16 h under argon atmosphere. The reaction mixture was concentrated under reduced pressure. The resulting residue was purified by silicagel column chromatography (AcOEt:n-hexane=4:1). The mixture of allyl compound (1.62 g) was obtained. To a solution of the obtained mixture in aceton (10 ml) was added 1% HCl (6 ml) and stirred for 2 h. The mixture was concentrated under reduced pressure and the residue was extracted with chloroform (30 ml). The organic layer was neutralized by satd. NaHCO$_3$ and dried (Na$_2$SO$_4$). The solvent was removed under reduced pressure. The resulting residue was purified by silicagel column chromatography AcOEt:n-hexane=4:1). 73 g (92%) of the objective compound was obtained as a colorless solid.

MS (m/z): 371, 330, 312, 210, 126.

IR (cm$^{-1}$) neat: 3290, 3071, 1746, 1658, 1020.

$^1$H-NMR (CDCl$_3$) δ: 1.47 (3H, s), 1.63 (3H, s), 1.66 (3H, s), 1.67 (3H, s), 1.99 (1H, m), 2.19 (1H, m), 3.94 (1H, m), 4.26 (1H, dd, J=3, 5 Hz), 4.37 (2H, m), 4.38 (1H, m), 5.01 (2H, m), 5.17 (1H, d, J=7 Hz), 5.43 (1H, t, J=3 Hz), 5.68 (1H, m), 6.19 (1H, s).

Referencial Example 10

The preparation of 1-(2-acetylamino-3,4-di-O-acetyl-6-O-tert-butyldimethylsilyl-2-deoxy-α-D-glucopyrano-1-yl)-propene (compound 1b-4)

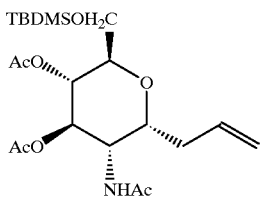

To a solution of the acetate compound (73 g, 0.2 mol) obtained from the above mentioned Referencial Example 9 in methanol (400 ml) was added sodium methoxide (5 g, 0.95 mmol) at 0° C. and stirred for 90 min. After the reaction was completed, the reaction mixture was neutralized by IR-120 resin, filtrated and concentrated. 54.8 g of the triol compound was obtained as a colorless solid. To a solution of the obtained triol compound (54.8 g, 224 mmol) in N,N-dimethylformamide (224 ml) was added imidazole (30.8 g, 448 mmol), tert-butyldimethylsilyl chloride (40.5 g, 268 mmol) and dimethylaminopyridine (2.7 g, 22.4 mmol) and the mixture was stirred for 70 h at 35° C. The reaction mixture poured into water and extracted with chloroform. The organic layer was neutralized by satd. NaHCO$_3$ and dried (Na$_2$SO$_4$). The solvent was removed under reduced pressure and 120 g of the silyl compound was obtained. To the obtained silyl compound was added pyridine (108 ml, 1.34 mol), acetic anhydride (84.7 ml, 0.89 mol) and dimethyaminopyridine (13.7 g, 0.11 mol). The reaction mixture was stirred for 1 h. Aftre the reaction was finished, the mixture was poured into water and extracted with ethyl acetate. After drying (Na$_2$SO$_4$), the solvent was removed under reduced pressure. The resulting residue was purified by silicagel column chromatography (AcOEt:n-hexane= 2:1). 33.4 g (35%) of the objective alcohol compound was obtained as a colerless oil.

MS (m/z): 428, 386, 326, 117.
$^1$H-NMR (CDCl$_3$) δ: 0.84 (9H, s), 1.92 (3H, s), 2.00 (3H, s), 2.02 (3H, s), 2.03 (3H, s), 2.18–2.25 (1H, m), 2.33–2.39 (1H, m), 3.69 (2H, s), 4.04–4.20 (3H, m), 4.93–5.11 (4H, m), 5.71–5.86 (2H, m).

Referencial Example 11

The preparation of 1-(2-acetylamino-3,4-di-O-acetyl-2-deoxy-α-D-glucopyrano-1-yl)-2-propene (compound 1b-6)

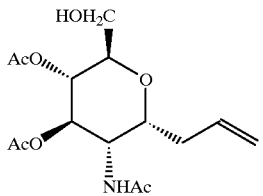

A solution of the silyl compound (10 g, 23.1 mmol) obtained from the above mentioned Referencial Example 10 in a mixture of tetaahydrofrane (10 ml), acetic acid (30 ml) and water (10 ml) was stirred for 62 h at 30° C. The reaction mixture was poured into water and extracted with chloroform, the organic extract was neutralized by satd.NaHCO$_3$, and dried over Na$_2$SO$_4$. The solvent was removed under reduced pressure. The resulting residue was purified by silicagel column chromatography (AcOEt). 7.5 g (100%) of the objective alcohol compound was obtained as a colorless solid.

MS (m/z): 330, 288, 268, 228, 126, 101.
IR (cm$^{-1}$) KBr: 3352, 2926, 1734, 1656, 1233.
$^1$H-NMR (CDCl$_3$) δ: 1.96 (3H, s), 2.05 (3H, s), 2.08 (3H, s), 2.28–2.35 (1H, m), 2.43–2.49 (1H, m), 3.57–3.69 (3H, m), 4.26–4.32 (2H, m), 4.97 (1H, dd, J=8.3, 8.3 Hz), 5.10–5.19 (3H, m), 5.78–5.86 (2H, m).

Referencial Example 12

The preparation of 1-(2-acetylamino-3,6-di-O-acetyl-2-deoxy-α-D-glucopyrano-1-yl)-2-propene (compound 1b-7)

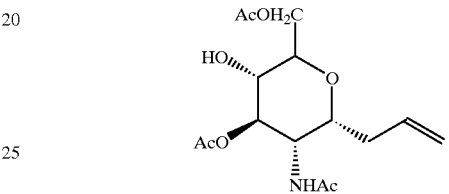

A mixture of the primary alcohol compound (7.5 g, 23.1 mmol) obtained from the above mentioned Referencial Example 11 and acetic acid (0.75 ml) in toluene (75 ml) was stirred for 18 h at 80° C. The mixture was concentrated under reduced pressure and the resulting residue was purified by silicagel column chromatography (AcOEt). 5.24 g (70%) of the objective compound was obtained as a colorless oil.

MS (m/z): 330, 228, 209, 168, 126, 101, 83.
IR (cm$^{-1}$) KBr: 3352, 1734, 1656, 1233.
$^1$H-NMR (CDCl$_3$) δ: 1.95 (3H, s), 2.13 (3H, s), 2.14 (3H, s), 2.30–2.36 (1H, m), 2.40–2.49 (1H, m), 3.55–3.59 (1H, m), 3.66–3.70 (1H, m), 4.18 (1H, dd, J=12.2, 2.9 Hz), 4.22–4.29 (2H, m), 4.51 (1H, dd, J=12.2, 4.9 Hz), 4.99 (1H, dd, J=8.3, 9.7 Hz), 5.10–5.16 (2H, m), 5.72–5.82 (1H, m), 5.90 (1H, d, J=8.3 Hz).

Example 1

The preparation of 2-acetylamino-1,3,4,6-tetra-O-acetyl-2-deoxy-α-D-galactopyranose (compound 1a-7)

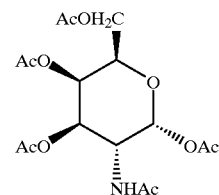

To a solution of cesium acetate (13.7 g, 71.5 mmol) in dimethylsulfoxide (15 ml) was added a solution of the trifrate compound (7.83 g) obtained from the above mentioned Referencial Example 4 in dimethylsulfoxide (15 ml). After the mixture was stirred for 3 h, the mixture was concentrated under reduced pressure. The residue was poured into water and extracted with dichloromethane, then dried over Na₂SO₄. The solvent was removed under reduced pressure. The resulting residue was purified by silicagel column chromatography (AcOEt). 3.4 g (61%) of the objective compound was obtained as a colorless oil.

MS (m/z): 389, 330, 287, 241, 114.

IR (cm$^{-1}$) neat: 1746, 1656, 1218, 1128.

$^1$H-NMR (CDCl₃) δ: 1.88 (3H, s), 1.96 (3H, s), 1.97 (3H, s), 2.10 (3H, s), 3.99 (1H, dd, J=11.2, 6.6 Hz), 4.04 (1H, dd, J=11.2, 6.8 Hz), 4.20 (1H, ddd, J=6.8, 6.6, 0.9 Hz), 4.63 (1H, ddd, J=11.6, 9.0, 3.6 Hz), 5.14 (1H, dd, J=11.7, 3.2 Hz), 5.36 (1H, dd, J=3.1, 0.7 Hz), 5.82 (1H, d, J=9.0 Hz), 6.15 (1H, d, J=3.6 Hz).

Example 2

The preparation of 1-(2-acetylamino-3,4,6-tri-O-acetyl-2-deoxy-α-D-galactopyrano-1-yl)-2-propene (compound 1a-8)

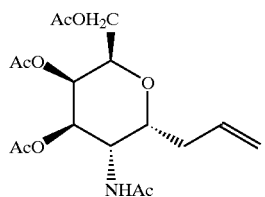

The alcohol compound (13.2 g, 40.1 mmol) obtained from the above mentioned Referencial Example 12 was dissolved in a mixture of dichloromethane (130 ml) and pyridine (13 ml). Then triflic anhydride (8.1 ml, 48.1 mmol) was added dropwise at −40° C. and stirred for 4 h. The mixture was poured into ice cold water and extracted with dichloromethane and the organic extract was washed with 10% HCl and dried over Na₂SO₄. The solvent was removed under reduced pressure and 16.1 g of triflate compound (16.1 g) was obtained. A solution of the obtained triflate compound (16.1 g) in dimethylsulfoxide (60 ml) was added to a solution of cesium acetate (20.0 g, 104 mmol) in dimethylsulfoxide (100 ml). After the mixture was stirred for 3 h, the mixture was concentrated under reduced pressure. The residue was poured into water and extracted with dichloromethane, then dried over Na₂SO₄. The solvent was removed under reduced pressure. The resulting residue was purified by silicagel column chromatography (AcOEt). 10.9 g (84%) of the objective compound was obtained as a colorless solid.

Example 3

The preparation of 2-(2-acetylamino-3,4,6-tri-O-acetyl-2-deoxy-α-D-galactopyrano-1-yl)-ethylazide (compound 2-1a)

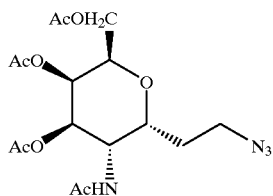

To a solution of the alcohol compound (2.33 g, 6.22 mmol) obtained from the above mentioned Referencial Example 8 in tetrahydrofran (62 ml) was added diphenylphosphoryl azide (2.68 ml, 12.4 mmol) and triphenylphosphine (3.25 g, 12.4 mmol). The solution was cooled to 0° C., diisopropyl azodicarboxylate (2.44 ml, 12.4 mmol) was added slowly to the solution and the mixture was stirred for 1 h. The reaction mixture was concentrated under reduced pressure and the resulting residue was purified by silicagel column chromatography (AcOEt:benzene=1:1). 1.92 g (77%) of the objective compound was obtained as a colorless oil.

MS (m/e): 401, 357, 313, 277, 166, 101.

IR (cm$^{-1}$) neat: 3244, 3046, 2092, 1737, 1656.

$^1$H-NMR (CDCl₃) δ: 1.66–1.72 (1H, m), 1.83–1.89 (1H, m), 2.00 (3H, s), 2.07 (3H, s), 2.08 (3H, s), 2.12 (3H, s), 3.35–3.39 (2H, m), 4.02–4.12 (2H, m), 4.31–4.35 (2H, m), 4.45 (1H, ddd, J=8.3, 8.3, 4.9 Hz), 5.14 (1H, dd, J=8.8, 3.4 Hz), 5.33 (1H, dd, J=3.4, 3.4 Hz), 6.23 (1H, d, J=8.3 Hz).

Example 4

The preparation of 2-(2-acetylamino-3,4,6-tri-O-acetyl-2-deoxy-α-D-galactopyrano-1-yl)-ethylamine (compound 2-2a)

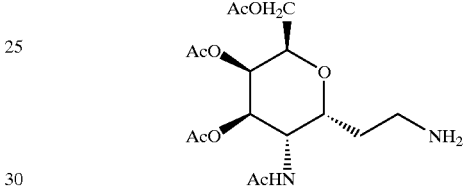

The azide compound (982 mg, 2.46 mmol) obtained from the above mentioned Example 3 was dissolved in methanol (10 ml), acetic acid (0.1 ml) and 10% Pd—C (98 mg) were added to the solution. The reaction mixture was stirred for 88 h under an atmosphere of H₂. The suspension was filtered and the filtrate was concentrated under reduced pressure. The resulting residue was purified by silicagel column chromatography (CHCl₃:MeOH:H₂O=8:2:0.2). 662 mg (72%) of the objective compound was obtained as a colorless oil.

MS (m/e): 374, 317, 256, 166, 115.

IR (cm$^{-1}$) neat: 3280, 2932, 1740, 1656.

$^1$H-NMR (CD₃OD) δ: 1.75–1.79 (1H, m), 1.97–2.01 (1H, m), 1.99 (3H, s), 2.03 (3H, s), 2.05 (3H, s), 2.09 (3H, s), 3.02–3.04 (2H, m), 4.07 (1H, dd, J=11.7, 4.4 Hz), 4.18–4.19 (1H, m), 4.31–4.45 (3H, m), 5.12 (1H, dd, J=9.3, 3.4 Hz), 5.42 (1H, dd, J=3.4, 3.4 Hz).

Example 5

The preparation of tert-butyl2-[2-acetylamino-3,4,6-tri-O-(2-acetyl-2-deoxy-α-D-galactopyrano-1-yl)ethylamino]acetate (compound 2-3a)

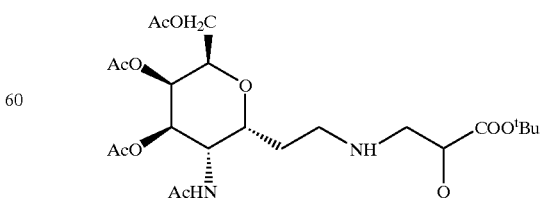

To a solution of the amine compound (590 mg, 1.58 mmol) obtained from the above mentioned Example 4 in dichloromethane (15.8 ml) was added triethylamine (0.33 ml, 2.73 mmol) and tert-butyl bromoacetic acid (0.35 ml, 2.37 mmol). After the mixture was stirred for 2 h at 60° C., the mixture was concentrated under reduced pressure. The resulting residue was purified by silicagel column chromatography (AcOEt:MeOH=10:1). 225 mg (27%) of the objective amide compound was obtained as a colorless oil.

MS (m/e): 489, 414, 387, 224, 164, 88.

IR (cm$^{-1}$) neat: 3328, 1740, 1656, 1233.

$^1$H-NMR (CD$_3$OD) δ: 1.54 (9H, s), 1.61–1.65 (1H, m), 1.96–1.98 (1H, m), 1.96 (3H, s), 2.02 (3H, s), 2.03 (3H, s), 2.10 (3H, s), 2.62–2.77 (2H, m), 3.28–3.37 (2H, m), 4.10 (1H, dd, J=10.7, 4.9 Hz), 4.16 (1H, ddd, J=8.3, 8.3, 2.4 Hz), 4.22 (1H, ddd, J=8.3, 8.3, 3.4 Hz), 4.24–4.32 (1H, m), 4.40 (1H, dd, J=9.8, 4.9 Hz), 5.12 (1H, dd, J=9.8, 2.9 Hz), 5.40 (1H, dd, J=2.9, 2.9 Hz).

Example 6

The preparation of tert-butyl 2-[N-acetyl-2-(2-acetylamino-3,4,6-tri-O-acetyl-2-deoxy-α-D-galactopyrano-1-yl)ethylamino]acetate (compound 2-4a)

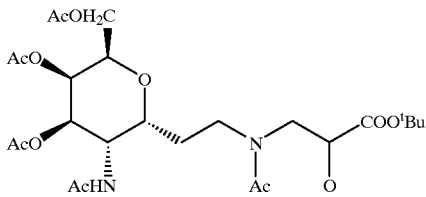

The amine compound (100 mg, 0.205 mmol) obtained from the above mentioned Example 5 was disolved in pyridine (1 ml), acetic anhydride (0.039 ml, 0.41 mmol) and dimethylaminopyridine (12 mg, 0.103 mmol) were added to the solution. After the solution was stirred for 1 h, the mixture was poured into water and extracted with ethyl acetate, the organic layer was washed with satd. CuSO$_4$ and brine, and dred over Na$_2$SO$_4$. The solvent was removed under reduced pressure, then the resulting residue was purified by silicagel column chromatography (AcOEt:MeOH=20:1). 100 mg (92%) of the objective compound was obtained as a colorless oil.

MS (m/e): 530, 487, 429, 387, 222, 57.

IR (cm$^{-1}$) neat: 2968, 1740, 1650, 1230.

$^1$H-NMR (CD$_3$OD) δ: 1.45 (9H, s), 1.73–1.77 (1H, m), 1.92–1.97 (1H, m), 1.97 (3H, s), 2.00 (3H, s), 2.03 (3H, s), 2.10 (3H, s), 2.16 (3H, s), 3.40–3.60 (2H, m), 3.89–4.30 (6H, m), 4.40–4.44 (1H, m), 5.07–5.14 (1H, m), 5.38–5.40 (1H, m).

Example 7

The preparation of 2-[N-acetyl-2-(2-acetylamino-3,4,6-tri-O-acetyl-2-deoxy-α-D-galactopyrano-1-yl) ethylamino]acetic acid (compound 2-5a)

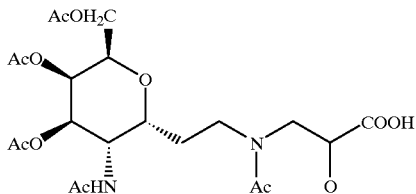

A mixture of the ester compound (90 mg, 0.17 mmol) obtained from the above mentioned Example 6 and trifluoroacetic acid (0.2 ml) in dichloromethane (1 ml) was stirred for 3 h. The mixture was concentrated under reduced pressure and the resulting residue was purified by silicagel column chromatography (CHCl$_3$:MeOH:AcOH=18:2:1). 70 mg (87%) of the objective compound was obtained as a colorless oil.

MS (m/e): 474, 429, 314, 222, 69.

IR (cm$^{-1}$) neat: 1740, 1370, 1230.

$^1$H-NMR (CD$_3$OD) δ: 1.76–1.82 (1H, m), 1.92–1.97 (1H, m), 1.99 (3H, s), 2.03 (3H, s), 2.11 (3H, s), 2.14 (3H, s), 2.17 (3H, s), 3.70–3.52 (2H, m), 4.00–4.30 (6H, m), 4.43–4.46 (1H, m), 5.08–5.14 (1H, m), 5.38–5.40 (1H, m), 4.43–4.46 (1H, m), 5.08–5.14 (1H, m), 5.38–5.40 (1H, m).

Example 8

The preparation of 2-(2-acetylamino-3,4,6-tri-O-acetyl-2-deoxy-α-D-galactopyrano-1-yl)-1-phenylthioethane (compound 4-1)

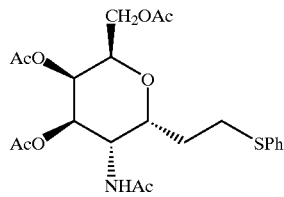

The compound (0.25 g, 0.67 mmol) obtained from the above mentioned Example 7 was dissolved in pyridine (3 ml), tributylphosphine (0.42 ml) and diphenyldisulfide (0.32 g) were added to the solution. The mixture was stirred for 3 h at 60° C. under argon atmosphere. The reaction mixture was extracted with ethyl acetate and washed with water and brine. After drying (MgSO$_4$), the solvent was removed under reduced pressure. The resulting residue was purified by silicagel column chromatography (BW-200, AcOEt:n-Hexane=10:1). 0.18 g (56%) of the objective thiophenyl compound was obtained as a colorless oil.

Mass (m/e): 467 (M$^+$).

$^1$H-NMR(CDCl$_3$) δ: 1.63 (1H, m), 1.94 (3H, s), 1.96 (1H, m), 2.03 (3H, s), 2.06 (3H, s), 2.56 (3H, s), 2.91 (1H, m), 3.24 (1H, m), 3.98 (1H, m), 4.51 (2H, m), 4.32 (1H, m), 4.42 (2H, m), 5.07 (1H, dd, J=4, 9 Hz), 5.29 (1H, t, J=3 Hz), 5.55 (1H, d, J=7 Hz), 7.21–7.38 (5H, m).

Example 9

The preparation of 2-(2-acetylamino-3,4,6-tri-O-acetyl-2-deoxy-α-D-galactopyrano-1-yl)-1-phenylsulufenylethane (compound 4-2)

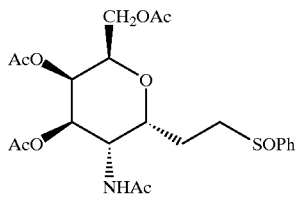

To a solution of the compound (0.14 g, 0.29 mmol) obtained from the above mentioned Example 8 in dichloromethane (2 ml) was slowly added a solution of 3-chloroperoxybenzoic acid in dichloromethane (1.0 ml) at −78° C. After stirring for 30 min, diethyl ether (10 ml) and 10% NaOH (1 ml) was added to the reaction mixture and the mixture was stirred for 15 min. The organic layer was separated and washed with water and brine. After drying (MgSO$_4$), the solvent was removed under reduced pressure. 0.15 g (99%) of the objective compound was obtained as a colorless oil.

Mass (m/e): 483 (M$^+$).

$^1$H-NMR(CDCl$_3$) δ: 1.89 (1H, m), 1.91 (3H, s), 1.95 (3H, s), 2.05 (3H, s), 2.09 (1H, m), 1.96 (1H, m), 2.58 (1H, m), 2.80 (1H, t, J=8 Hz), 3.01 (1H, m), 3.80 (1H, m), 3.95–4.10 (2H, m), 4.20 (1H, m), 4.35 (1H, m), 4.56 (2H, m), 5.10 (1H, dd, J=4, 9 Hz), 5.27 (1H, t, J=3 Hz), 6.50 (1H, d, J=8 Hz), 7.4–7.60 (5H, m).

Example 10

The preparation of (2-acetylamino-3,4,6-tri-O-acetyl-2-deoxy-α-D-galactopyrano-1-yl)-vinylene (compound 4-3)

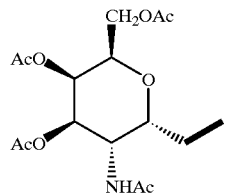

A mixture of the compound (0.14 g), 0.29 mmol) obtained from the above mentioned Example 9 and diisopropylethylamine (0.09 ml) in toluene (2 ml) was refluxed for 18 h. After the reaction mixture was cooled to room temperature, the mixture was extracted with ethyl acetate and washed with water and brine. After drying (MgSO$_4$), the solvent was removed under reduced pressure. The resulting residue was purified by silicagel column chromatography (BW-200, AcOEt). 0.07 g (70%) of the oily objective compound was obtained as a colorless oil.

Mass (m/e): 357 (M$^+$), 298, 255, 165, 101(BP), 59.

$^1$H-NMR(CDCl$_3$) δ: 1.96 (3H, s), 2.05 (3H, s), 2.06 3H, s), 2.16 (3H, s), 4.14 (3H, m), 4.62 (1H, m), 4.76 (1H, m), 5.03 (1H, dd, J=4, 10 Hz), 5.35 (1H, d, J=2 Hz), 5.45 (3H, m), 5.95 (1H, m).

Example 11

The preparation of (2-acetylamino-3,4,6-tri-O-acetyl-2-deoxy-α-D-galactopyranos-1-yl)-1-carbaldehyde (compound 4-4)

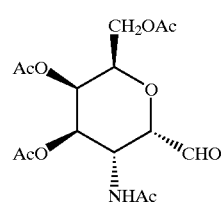

To a mixture of the compound (0.07 g, 0.20 mmol) obtained from the above mentioned Example 10, in tetrahydrofran (2 ml) and water was added NaIO$_4$ (0.16 g, 0.78 mmol) and 4% OsO$_4$ solution (0.01 ml). After the mixture was stirred for 4 h, the reaction mixture was extracted with ethyl acetate and washed with water and brine. After drying (MgSO$_4$), the solvent was removed under reduced pressure. 0.705 g (69.6%) of the objective aldehyde compound was obtained as a colorless oil.

Mass (m/e): 360(M$^{+1}$), 330, 300, 199, 139, 97(BP), 59.

$^1$H-NMR(CDCl$_3$) δ: 1.98 (3H, s), 2.06 (3H, s), 2.02 (3H, S), 2.17 (3H, s), 3.92 (1H, t, J=7 Hz), 4.20 (2H, m), 4.59 (1H, d, J=Hz), 4.80 (1H, m), 5.09 (1H, dd, J=3, 9 Hz), 5.38 (1H, d, J=3 Hz), 6.22 (1H, d, J=9 Hz), 9.83 (1H, S).

Example 12

The preparation of (2-acetylamino-3,4,6-tri-O-acetyl-2-deoxy-α-D-galactopyrano-1-yl)-1-methanol (compound 4-5)

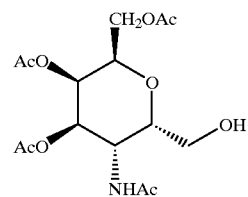

A mixture of the compound (0.77 g, 1.85 mmol) obtained from the above mentioned Example 11 and sodium borohydride (0.1 g, 2.78 mmol) in methanol (10 ml) was stirred for 10 min at 0° C. The reaction mixture was poured into satd. NH$_4$Cl and the mixture was extracted with dichloromethane, the organic layer was washed with water and brine. After drying (MgSO$_4$), the solvent was removed under reduced pressure. The resulting residue was purified by silicagel column chromatography (BW-200, AcOEt). 0.25 g (36%) of the objective alcohol compound was obtained as a colorless oil.

Mass (m/e): 362(M$^{+1}$), 330, 300, 199, 139, 97(BP), 59.

$^1$H-NMR(CDCl$_3$) δ: 1.98 (3H, s), 2.06 (31H, s), 2.02 (3H, s), 2.17 (3H, s), 3.92 (1H, t, J=7 Hz), 4.20 (2H, m), 4.59 (1H, d, J=3 Hz), 4.80 (1H, m), 5.09 (1H, dd, J=3, 9 Hz), 5.38 (1H, d, J=3 Hz), 6.22 (1H, d, J=9 Hz), 9.83 (1H, s).

Example 13

The preparation of 2-(2-acetamino-3,4,6-tri-O-acetyl-2-deoxy-α-D-galactopyrano-1-yl)-ethylvinyloxyformate (compound 5-1a)

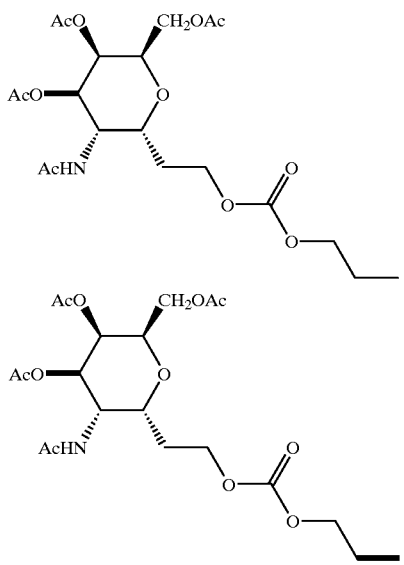

The compound (0.09 g, 2.27 mmol) obtained from the above mentioned Example 8 was disolved in tetrahydrofuran (5 ml), allyl chloroformate (0.026 ml, 2.5 mmol) was added to the solution in the presence of pyridine (1 ml). After the solution was stirred for 30 min, the reaction mixture was extracted with ethyl acetate and the organic layer was washed with water and brine. After drying ($MgSO_4$), the solvent was removed under reduced pressure and the resulting residue was purified by silicagel column chromatography (BW-200, AcOEt:n-hexane=4:1). 0.08 g (70%) of the objective compound was obtained as a colorless oil.

IR ($cm^{-1}$) KBr: 1743, 1392, 1245, 1020.

$^1$H-NMR($CDCl_3$) δ: 1.58 (1H, m), 1.99, (3H, s), 2.07 (3H, s), 2.08 (3H, s), 2.12 (3H, s), 4.12 (2H, m), 4.19–4.35 (4H, m), 4.38 (1H, m), 4.48 (1H, m), 4.62 (2H, d, J=6 Hz), 5.13 (1H, dd, J=3, 8 Hz), 5.27–5.39 (3H, m), 5.64 (1H, d, J=8 Hz).

Example 14

The preparation of 1-[2-(2-acetylamino-3,4,6-tri-O-acetyl-2-deoxy-α-D-galactopyrano-1-yl)-2-propene (compound 5-2a)

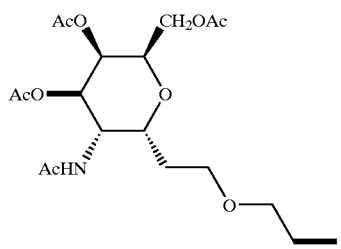

The compound (0.07 g, 0.15 mmol) obtained from the above mentioned Example 13 was disolved in benzene (2 ml), Pd(OAC)$_2$ (0.7 mg) and triphenylphosphine (4 mg) were added to the solution under argon atmosphere. After the mixture was stirred for 2 h at 70° C., the mixture was concentrated. The resulting residue was purified by silicagel column chromatography (BW-200, AcOEt:hexane=4:1). 0.045 g (72.3%) of the objective compound was obtained as a colorless oil.

Mass (m/e): 415(M$^+$), 358, 314, 277, 181, 152, 101, 59.

$^1$H-NMR($CDCl_3$) δ: 1.82 (1H, m), 1.91 (1H, m), 1.97 (3H, s), 2.05 (3H, s), 2.06 (3H, s), 2.12 (3H, s), 3.50 (2H, m), 3.97 (2H, d, J=3 Hz), 4.06 (2H, m), 4.22 (1H, m), 4.28 (1H, m), 4.50 (1H, m), 5.12 (1H, dd, J=3,5 Hz), 5.15 (1H, dd, J=2,7 Hz), 5.30 (1H, m), 5.76 (1H, d, J=8 Hz), 5.90 (1H, m).

Example 15

The preparation of 1-[2-(2-acetylamino-3,4,6-tri O-acetyl-2-deoxy-α-D-galactopyrano-1-yl)ethoxy]-2-benzylamino-ethane (compound 5-3a)

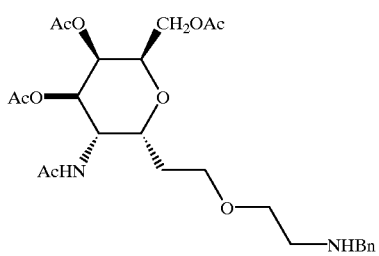

A solution of the compound (0.69 g, 1.65 mmol) obtained from the above mentioned Example 14 in methanol (5 ml) and dichlorometane (5 ml) was ozonized at −78° C. After the reaction was completed, dimethylsulfide was added to the mixture and the solution was stirred at room temperature. The mixture was concentrated and 0.69 g (99%) of the aldehyde was obtained. To a solution of the obtained aldehyde in dichloromethane (5 ml) was added benzylamine (0.22 ml). After stirring for 15 min, sodium triacetoxyborohydride (0.5 g) was added to the mixture and the mixture was stirred for 12 h. The reaction mixture was extracted with chloroform and the organic layer was washed with water and brine. After drying (Na$_2$SO$_4$), the solvent was removed under reduced pressure and the resulting residue was purified by silicagel column chromatography (BW-200, chloroform:methanol=20:1). 0.51 g (64.4%) of the objective compound was obtained as a colorless oil.

Mass (m/e): 449 (M-NHAc), 383, 192, 120, 91.

IR ($cm^{-1}$) KBr: 3290, 2950, 1740, 1660, 1378, 1230, 1000.

$^1$H-NMR($CDCl_3$) δ: 1.87 (1H, m), 1.95 (3H, s), 1.97 (1H, m), 2.05 (6H, m), 2.19 (3H, s), 2.81 (2H, t, J=5.0 Hz), 3.51 (2H, m), 3.57 (2H, t, J=5.0 Hz), 3.84 (1H, s), 4.03 (1H, m), 4.08 (1H, m), 4.38 (1H, m), 4.50 (1H, m), 5.13 (1H, dd, J=8.3, 2.1 Hz), 5.31 (1H, t, J=3 Hz), 5.85 (1H, d, J=8.0 Hz), 7.32 (5H, m).

Example 16

The preparation of tert-butyl 2-{2-[2-(2-acetylamino-3,4,6-tri-O-acetyl-2-deoxy-α-D-galactopyrano-1-yl)ethoxy]-N-benzylethylamino}acetate (compound 5-4a)

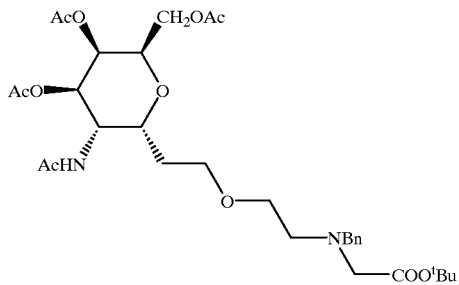

A mixture of the compound (0.51 g, 1.03 mmol) obtained from the above mentioned Example 15 and tert-butyl bromoacetic acid (0.3 ml) in dichloromethane (5 ml) was stirred for 16 h at 60° C. After the reaction was completed, triethylamine was added to the mixture and stirred for 15 min. The mixture was extracted with ethyl acetate and washed with water and brine. After drying (MgSO$_4$), the solvent was removed under reduced pressure and the resulting residue was purified by silicagel column chromatography (ABW-200, CHCl$_3$:MeOH=10:1). 0.23 g (36.9%) of the objective compound was obtained as a colorless oil.

$^1$H-NMR(CDCl$_3$) δ: 1.45 (9H, s), 1.75 (1H, m), 1.84 (1H, m), 1.97 (3H, s), 2.05 (3H, s), 2.06 (3H, s), 2.12 (3H, s), 2.86 (2H, t, J=6.0 Hz), 3.29 (2H, s), 3.40–3.60 (4H, m), 3.83 (2H, s), 4.02 (1H, m), 4.11 (1H, m), 4.20 (1H, m), 4.32 (1H, m), 4.50 (1H, m), 5.11 (1H, dd, J=6.0, 2.0 Hz), 5.31 (1H, t, J=3 Hz), 5.70 (1H, d, J=6.0 Hz), 7.33 (5H, m).

Example 17

The preparation of tert-butyl-2-{2-[2-(2-acetylamino-3,4,6-tri-O-acetyl-2-deoxy-α-D-galactopyrano-1-yl)ethoxy]ethylamino}acetate (compound 5-5a)

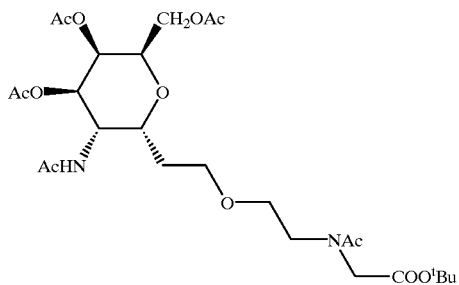

The compound (0.21 g, 0.34 mmol) obtained from the above mentioned Example 16 disolved in methanol (10 ml), acetic acid (0.5 ml) and 10% Pd—C(20 mg) were added to the solution. The reaction mixture was stirred for 3 h under an atmosphere of H$_2$, then the suspension was filtered through celite and the filtrate was concentrated. 0.18 g (99%) of the objective compound was obtained as a colorless oil.

Mass (m/e):431, 373, 314, 91, 78.

$^1$H-NMR(CDCl$_3$) δ: 1.45 (9H, s), 1.91 (1H, m), 1.95 (1H, m), 2.01 (3H, s), 2.05 (6H, s), 2.05 (3H, s), 2.50 (1H, s), 2.87 (2H, t, J=6.0 Hz), 3.40–3.70 (4H, m), 4.10 (2H, m), 4.20–4.41 (3H, m), 4.50 (2H, m), 5.20 (1H, dd, J=6.0, 2.0 Hz), 5.33 (1H, t, J=3 Hz), 6.05 (1H, d, J=6.0 Hz).

Example 18

The preparation of tert-butyl 2-{2-[2-(2-acetylamino-3,4,6-tri-O-acetyl-2-deoxy-α-D-galactopyrano-1-yl)ethoxy]-N-acetylethylamino}acetate (compound 5-6a)

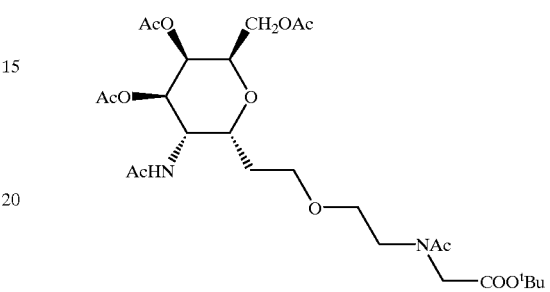

To a solution of the compound (0.18 g, 0.34 mmol) obtained from the above mentioned Example 17 in dichloromethane (5 ml) was slowly added acetyl chloride (0.36 ml) in the presence of diisopropylethylamine (0.1 ml). After the solution was stirred for 2 h, the mixture was concentrated under reduced pressure and the resulting residue was purified by silicagel column chromatography (BW-200, AcOEt). 0.13 g (66.5%) of the objective compound was obtained as a colorless oil.

Mass (m/e): 517 (M-Bu), 501, 431, 358, 314, 199, 144, 99, 72.

$^1$H-NMR(CDCl$_3$) δ: 1.47 9H, s), 1.83 (1H, m), 1.93 (1H, m), 1.86 (3H, s), 1.91–2.20 (15H, m), 3.40–3.60 (10H, m), 3.96–4.40 (9H, m), 4.50 (1H, m), 5.18 (1H, dd, J=6.0, 3.0), 5.30 (1H, t, J=3.0 Hz), 5.75 (1H, m).

Example 19

The preparation of 2-{2-[2-(2-acetylamino-3,4,6-tri-O-acetyl-2-deoxy-α-D-galactopyrano-1-yl)ethoxy]-N-ethylamino}acetic acid (compound 5-7a)

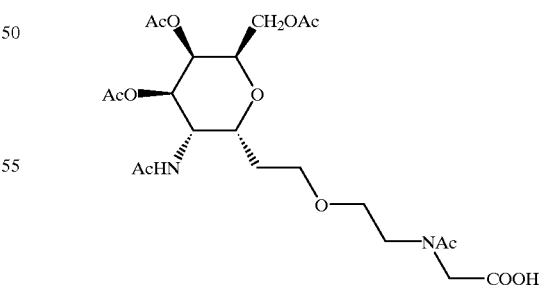

A mixture of the compound (0.15 g, 0.26 mmol) obtained from the above mentioned Example 18 and trifluoroacetic acid (0.4 ml) in dichloromethane (2 ml) was added to the mixture and stirred for 3 h. The reaction mixture was concentrated and 0.13 g (66.8%) of the objective compound was obtained as a colorless oil.

Mass (m/e): 517 (M-Bu), 501, 431, 358, 314, 199, 144, 99, 72.

$^1$H-NMR(CDCl$_3$) δ: 0.89 (1H, m), 0.97 (1H, m), 2.00 (3H, s), 2.03 (3H, s), 2.04 (3H, s), 2.15 (3H, s), 2.19 (3H, s), 3.40–3.65 (6H, m), 3.95–4.18 (3H, m), 4.30 (2H, m), 4.46 (1H, m), 5.10 (1H, d, J=4.0 Hz), 5.18 (1H, m).

Example 20

The preparation of 2-[O-(methyl 5-acetylamino-4,7,8,9-tetra-O-acetyl-3,5-dideoxy-β-D-glycero-D-galacto-2-nonulopyranoside)-(2→6)-(2-acetylamino-3,4-di-O-acetyl-2-deoxy-α-D-galactopyrano-1-yl)]-1-(2-propenyloxy)ethane (compound 6-2a)

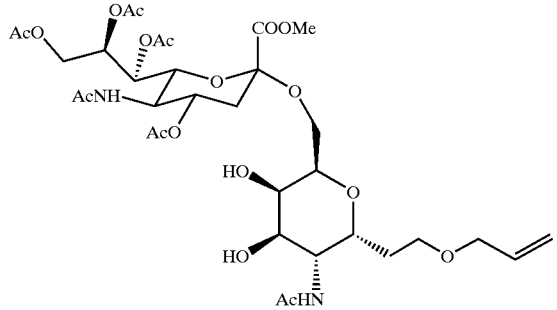

A mixture of the alcohol compound (173 mg, 0.66 mmol) obtained from the above mentioned Example 14 and MS4A (380 g) in tetrahydrufuran (10 ml) was added di-tert-butylpyridine (0.29 ml) and AgOTf (337 mg) and the mixture was stirred for 30 min. After cooling to −78° C., a solution of the sialyl chloride (670 mg, 0.66 mmol) in tetrahydrofurane (8 ml) was added dropwise to the mixture and the mixture was stirred for 28 h. The suspension was filtered through Celite and the filtrate was removed under reduced pressure. The resulting residue was purified by silicagel column chromatography (CHCl3:MeOH=10:1). 81 mg (18%) of the objective compound was obtained as a colorless oil.

MS (ESI, m/e): 785 (M$^+$).

IR (cm$^{-1}$): 3340, 2944, 1744, 1656.

$^1$H-NMR (CDCl$_3$) δ: 1.88 (3H, s), 1.99 (3H, s), 2.03 (3H, s), 2.04 (3H, s), 2.13 (3H, s), 2.14 (3H, s), 2.58 (1H, dd, J=17.4, 4.4 Hz), 2.97 (1H, d, J=3.9 Hz), 3.99–4.10 (4H, m), 4.14–4.27 (2H, m), 4.34 (1H, dd, J=12.2, 2.5 Hz), 4.40–4.43 (1H, m), 4.84–4.91 (1H, m), 5.21–5.39 (4H, m), 5.87–5.96 (1H, m), 6.74 (1H, d, J=5.9 Hz).

Example 21

The preparation of 2-[O-(5-acetylamino-3,5-dideoxy-β-D-glycero-D-galacto-2-nonulopyranoside)-(2→6)-(2-acetylamino-2-deoxy-α-D-galactopyrano-1-yl)]-1-(2-propenyloxy)ethane (compound 6-3a)

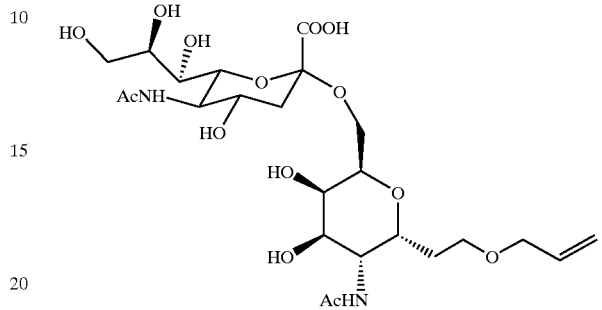

A mixture of the compound (21 mg, 0.027 mmol) obtained from the above mentioned Example 20 and 2% K$_2$CO$_3$ (3 ml) in methanol (9 ml) was stirred for 20 h. The reaction mixture was neutralized by 1% HCl, then the reaction mixture was concentrated under reduced pressure. The resulting residue was purified by silicagel column chromatography (PR-18, H2O:AcOH=100:1). 13 mg (81%) of the objective compound was obtained as a colorless oil.

MS (ESI, m/e): 579 (M−H)$^+$.

IR (cm$^{-1}$) neat: 3268, 1638, 1566.

$^1$H-NMR (CD$_3$OD) δ: 1.60–1.80 (2H, m), 2.01–2.05 (1H, m), 2.01 (3H, s), 2.05 (3H, s), 2.85–2.88 (1H, m), 3.50–3.60 (3H, m), 3.65–3.76 (5H, m), 3.81–3.95 (5H, m), 4.02 (2H, d, J=5.4 Hz), 4.21–4.33 (2H, m), 5.18–5.21 (1H, m), 5.29–5.34 (1H, m), 5.91–6.00 (1H, m).

Example 22

The preparation of 2-(2-{2-[5-acetylamino-3,5-dideoxy-β-D-glycero-D-galacto-2-nonulopyranoside)-(2→6)-(2-acetylamino-2-deoxy-α-D-galactopyrano-1-yl)]ethoxy}-N-acetyl-ethylamino)-N-(2-{2-(2-propenyloxy)ethoxy]ethoxy}ethyl)acetamide (6-3b)

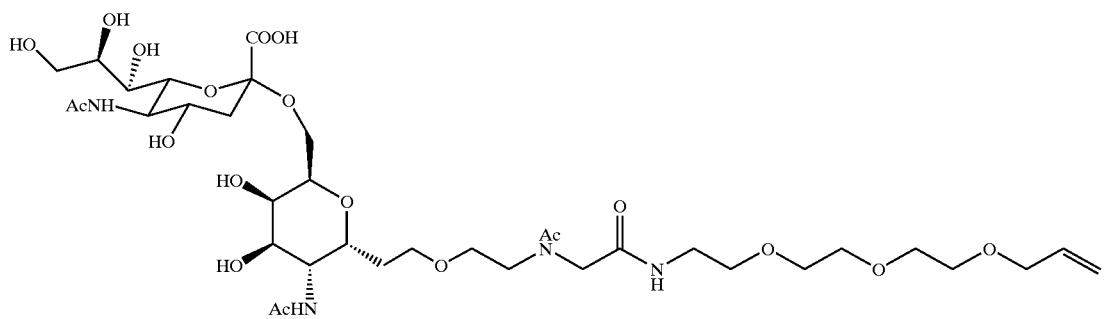

To use of the compound obtained from the following mentioned Example 32, the objective compound was obtained according to the method described in Example 20–21.

MS (ESI, m/e): 877 (M+Na)$^+$.

IR (cm$^{-1}$) KBr: 3400, 2950, 1650, 1400, 1125.

$^1$H-NMR (CD$_3$OD) δ: 1.62 (2H, m), 2.01 (3H, s), 2.04 (3H, s), 2.20 (3H, s), 2.81 (1H, dd, J=2.8 Hz), 3.40–3.98 (30H, m), 4.18 (4H, m), 4.21 (4H, m), 5.20 (1H, d, J=12 Hz), 5.19 (1H, d, J=12 Hz), 6.98 (1H, m).

Example 23

The preparation of the following compound.

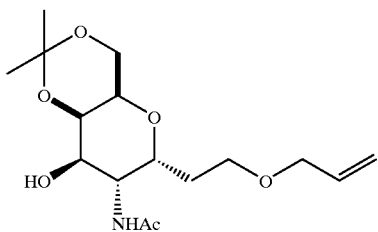

To a solution of the compound (0.12 g, 0.41 mmol) obtained from the above mentioned Example 14 in acetonitrile (10 ml) was added benzaldehyddimethylacetal (0.12 ml) and p-toluensulfonate (3.8 mg) and the mixture was stirred for 6 h at 60° C. under argon atmosphere. After cooling to room temperature, the mixture was extracted with ethyl acetate and the organic layer was washed with water and brine. After drying (MgSO$_4$), the solvent was removed under reduced pressure. The resulting residue was purified by silicagel column chromatography (BW-200, AcOEt). 0.10 g (64.4%) of the objective acetal compound was obtained as a colorless oil.

MS (ESI, m/e) 377 (M)$^+$.

$^1$H-NMR (CDCl$_3$) δ: 1.96 (2H, m), 1.99 (3H, s), 3.43–3.60 (3H, m), 3.75 (1H, d, J=3 Hz), 4.01 (3H, m), 4.11 (2H, m), 4.42 (2H, m), 5.20 (2H, dd, J=3, 8 Hz), 5.60 (1H, s), 5.90 (1H, m), 6.20 (1H, d, J=3 Hz), 7.30–7.56 (5H, m).

Example 24

The preparation of the following compound.

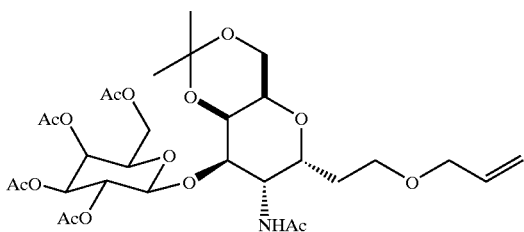

A mixture of the compound (10 mg, 0.41 mmol) obtained from the above mentioned Example 23 and MS4A (380 g) in dichloromethane (10 ml) was added di tert-butylpyridine (0.12 ml) and AgOTf (0.14 g) and the mixture was stirred for 30 min. After cooling to −78° C., a solution of the galactose derivatives (0.22 g 0.41 mmol) in dichloromethane was added dropwise to the mixture. After the reaction was completed, the solvent was removed under reduced pressure. The resulting residue was purified by silicagel column chromatography (BW-200, AcOEt). 0.10 g (64.4%) of the objective compound was obtained as a colorless oil.

MS (ESI, m/e): 707 (M)$^+$.

$^1$H-NMR (CDCl$_3$) δ: 1.96 (2H, m), 1.99 (3H, s), 3.43–3.60 (3H, m), 3.75 (1H, d, J=3 Hz), 4.01 (3H, m), 4.11 (2H, m), 4.42 (2H, m), 5.20 (2H, dd, J=3, 8 Hz), 5.60 (1H, s), 5.90 (1H, m), 6.20 (1H, d, J=3 Hz), 7.30–7.56 (5H, m).

Example 25

The preparation of the following compound.

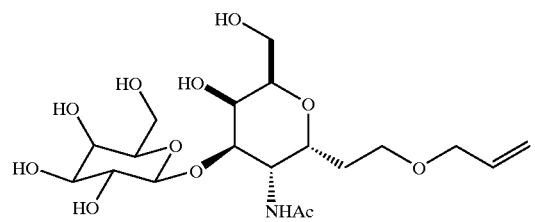

A solution of the compound (0.11 g, 0.16 mmol) obtained from the above mentioned Example 24 in 80% acetic acid was heated to 70° C. and stirred for 2 h. The solvent was removed under reduced pressuremixture and the obtained diol compound was dissolved in methanol (5 ml). Sodium methoxide (2 mg) was added to the solution and the mixture was stirred for 2 h at room temperature. The reaction mixture was neutralized by Amberlite IR-120 and filtrated and the filtrate was concentrated under reduced pressure. 0.1 g (64.4%) of the objective compound was obtained.

MS (ESI, m/e): 451 (M)$^+$.

$^1$H-NMR (CDCl$_3$) δ: 1.75 (1H, m), 2.00 (1H, m), 2.13 (3H, s), 3.16 (1H, m), 3.55 (2H, m), 3.60 (1H, m), 3.69–3.82 (3H, m), 3.98 (2H, m), 4.01–4.10 (5H, m), 4.30 (1H, m), 4.80 (3H, m), 5.11 (1H, m), 5.18 (2H, m), 5.23 (1H, m), 5.40 (1H, m), 5.90 (1H, m).

Example 26

The preparation of tert-butyl 2-{N-[2-(2-acetylamino-3,4,6-tri-O-acetyl-2-deoxy-α-D-galactopyrano-1-yl)ethyl]-2-[2-(2-acetylamino-3,4,6-tri-O-acetyl-2-deoxy-α-D-galactopyrano-1-yl)-N-acetyl-ethylamino]acetylamino}acetate (compound 8-3a)

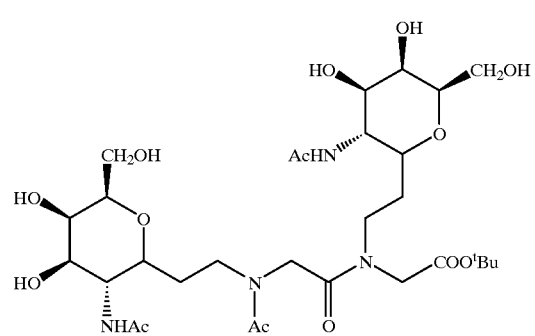

A mixture of carboxylic acid (67 mg, 0.14 mmol) and amine (69 mg, 0.14 mmol) obtained from above mentioned Example 7 and 5 were disolved in acetonitorile (1.4 ml), diisopropylethylamine (0.027 ml) and O-(benzotriazol-1-yl) N,N,N',N'-tetramethylhydroniumtetrafluoroborate (TBTU) (50 mg) were added to the mixture. After the reaction mixture was stirred for 24 h, the mixture was poured into brine and extracted with chloroform, the organic layer was dried over Na$_2$SO$_4$ and the solvent was removed under reduced pressure. The resulting residue was purified by silicagel column chromatography (AcOEt:MeOH=10:1). 72 mg (54%) of the objective compound was obtained as a colorless oil.

MS (ESI, m/e): 944 (M$^+$).

$^1$H-NMR (CD$_3$OD) δ: 1.46 (9H, s), 1.77–1.83 (1H, m), 1.92–1.97 (1H, m), 1.90 (3H, s), 1.91 (3H, s), 1.94 (3H, s), 1.95 (3H, s), 2.00 (3H, s), 2.01 (3H, s), 2.04 (3H, s), 2.05 (3H, s), 2.11 (3H, s), 3.41–3.68 (4H, m), 3.90–4.59 (14H, m), 5.09–5.16 (2H, m), 5.40–5.42 (2H, m).

Example 27

The preparation of 2-{N-[2-(2-acetylamino-3,4,6-tri-O-acetyl-2-deoxy-α-D-galactopyrano-1-yl)ethyl]-2-[N-(2-acetylamino-3,4,6-tri-O-acetyl-2-deoxy-α-D-galactopyrano-1-yl)-N-acetyl-ethylamino]acetylamino}acetic acid (compound 8-1b)

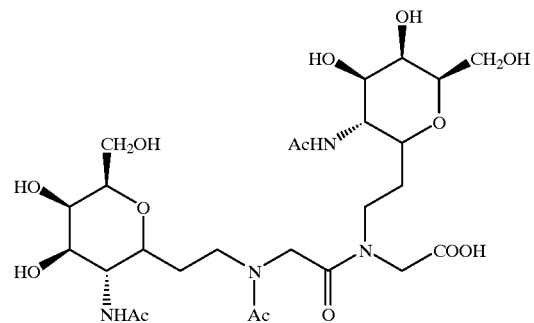

A solution of the ester compound (62 mg, 65.7 μmol) obtained from the above mentioned Example 26 and trifluoroacetic acid (0.2 ml) in dichloromethane (1 ml) was stirred for 4 h. The reaction mixture was concentrated under reduced pressure, and the resulting residue was purified by silicagel column chromatography (CHCl$_3$:MeOH:AcOH= 18:2:1). 50 mg (86%) of the objective compound was obtained as a colorless oil.

MS (ESI, m/e): 888 (M$^+$).

$^1$H-NMR (CD$_3$OD) δ: 1.77–1.82 (2H, m), 1.94 (3H, s), 1.95 (3H, s), 1.97 (3H, s), 1.99 (3H, s), 2.00 (3H, s), 2.02 (3H, s), 2.04 (3H, s), 2.07 (3H, s), 2.11 (3H, s), 3.34–3.77 (4H, m), 4.06–4.87 ((14H, m), 5.10–5.15 (2H, m), 5.33–5.41 (2H, m).

Example 28

The preparation of tert-butyl 2-(2-{2-[2-(2-acetylamino-3,4,6-tri-O-acetyl-2-deoxy-α-D-galactopyrano-1-yl)-N-acetylethylamino]-N-[2-(2-acetylamino-3,4,6-tri-O-acetyl-2-deoxy-α-D-galactopyrano-1-yl)ethyl]acetylamino}-N-[2-(2-acetylamino-3,4,6-tri-O-acetyl-2-deoxy-α-D-galactopyrano-1-yl)ethyl]acetylamino)acetate
(compound 8-3b)

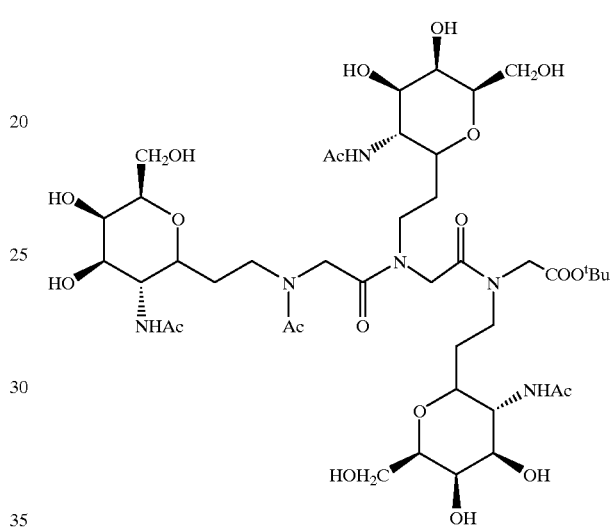

To a solution of carboxylic acid (48 mg, 54.1 μmol) and amine (26.3 mg, 54.1 μmol) obtained from above mentioned Example 27 and 17 in acetonitorile (1 ml) was added diisopropylethylamine (10 μl, 59.5 μmol) and O-(benzotriazol-1-yl) N,N,N',N'-tetramethylhydroniumtetrafluoroborate (TBTU) (19 mg, 59.5 μmol). After stirring for 38 h, the mixture was poured into brine and extracted with chloroform, the organic layer was dried over Na$_2$SO$_4$ and the solvent was removed under reduced pressure. The resulting residue was purified by silicagel column chromatography (AcOEt:MeOH=5:1). 40 mg (54%) of the objective compound was obtained as a colorless oil.

MS (ESI, m/e): 1382 (M+Na)$^+$.

$^1$H-NMR (CD$_3$OD) δ: 1.46 (9H, s), 1.73–1.83 (3H, m), 1.94–2.18 (42H, m), 3.41–3.78 (8H, m), 4.03–4.55 (21H, m), 5.10–5.15 (3H, m), 5.40–5.42 (3H, m).

Example 29

The preparation of 2-(2-{2-[2-(2-acetylamino-3,4,6-tri-O-acetyl-2-deoxy-α-D-galactopyrano-1-yl)-N-acetylamino]-N-[2-(2-acetylamino-3,4,6-tri-O-acetyl-2-deoxy-α-D-galactopyrano-1-yl)ethyl]acetylamino}-N-[2-(2-acetylamino-3,4,6-tri-O-acetyl-2-deoxy-α-D-galactopyrano-1-yl)ethyl]acetylamino)acetic acid (compound 8-1c)

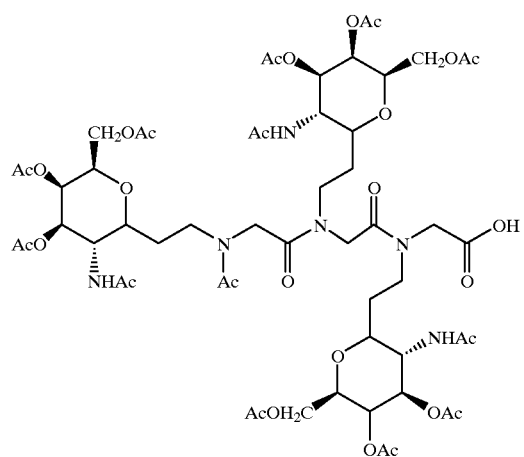

A solution of the ester compound (40 mg, 29.5 μmol) obtained from the above mentioned Example 28 and trifluoroacetic acid (0.2 ml) in dichloromethane (1 ml) was stirred for 16 h. The reaction mixture was concentrated under reduced pressure and the resulting residue was purified by silicagel column chromatography (CHCl$_3$:MeOH:AcOH=18:2:1). 18 mg (47%) of the objective compound was obtained as a colorless oil.

MS (ESI, m/e): 1302 (M$^+$).

$^1$H-NMR (CD$_3$OD) δ: 1.65–1.75 (3H, m), 2.00–2.14 (42H, m), 3.31–3.60 (6H, m), 4.05–4.50 (21H, m), 5.05–5.10 (3H, m), 5.30–5.39 (3H, m).

Example 30

The preparation of the following compound.

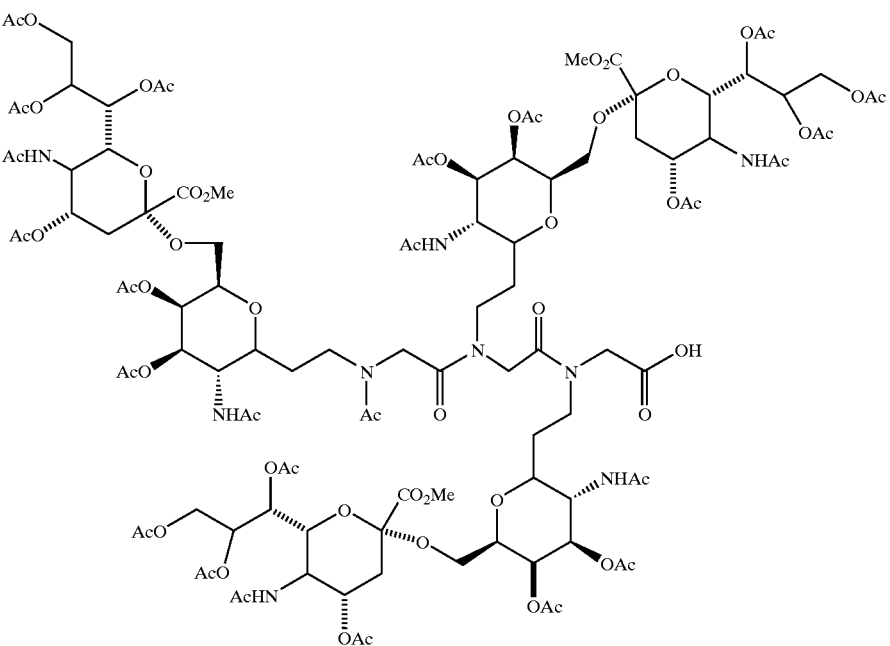

To use of the compound obtained from the above mentioned Example 20, the objective compound was obtained according to the method described in Example 26–28.

¹H-NMR (CD₃OD) δ: 1.80–2.25 (69H, m), 3.01–3.68 (50H, m), 3.90–4.58 (6H, m).

Example 31

The preparation of 2-(2-Acetylamino-3,4,6-tri-O-acetyl-2-deoxy-α-D-galactopyrano-1-yl)-1-(2-{N-[(N-{2-[2-(2-propenyloxy)ethoxy]ethoxy}ethyl)carbamoylmethyl]acetylamino}ethoxy)ethane (compound 8-4)

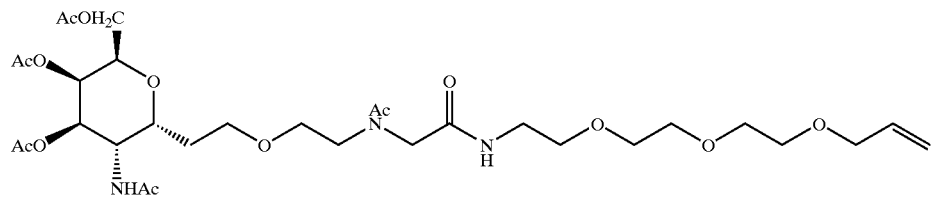

To a solution of carboxylic acid (23 mg, 44.4 μmol) obtained from above mentioned Example 19 and amine (17 mg, 88.8 μmol) in acetonitrile (1 ml) was added diisopropylethylamine (9 μL, 48.8 μmol), O-(benzotriazol-1-yl)N,N,N',N'-tetramethylhydroniumtetrafluoroborate (TBTU) (16 mg, 48.8 μmol). After the mixture was stirred for 4 h, the mixture was poured into brine and extracted with chloroform, the organic layer was washed with 10% HCl and satd. NaHCO₃. After drying (Na₂SO₄), the solvent was removed under reduced pressure and the resulting residue was purified by silicagel chromatography (AcOEt:MeOH= 8:1). 20 mg (65%) of the objective compound was obtained as a colorless oil.

MS (ESI, m/e): 688 (M⁺).

IR (cm⁻¹) neat: 3286, 2860, 1743, 1650.

¹H-NMR (CDCl₃) δ: 1.80–1.86 (1H, m), 2.00 (3H, s), 2.06 (3H, s), 2.12 (3H, s), 2.13 (3H, s), 2.18 (3H, s), 3.42–3.67 (18H, m), 4.40–4.11 (6H, m), 4.20–4.30 (1H, m), 4.34–4.41 (1H, m), 4.42–4.47 (1H, m), 5.10–5.14 (1H, m), 5.17–5.20 (1H, m), 5.25–5.30 (1H, m), 5.31–5.32 (1H, m), 5.86–5.98 (1H, m).

Example 32

The preparation of 2-(2-Acetylamino-2-deoxy-α-D-galactopyrano-1-yl)-1-[2-(N-{[N-(2-{2-[2-(2-propenyloxy)ethoxy]ethoxy}ethyl)carbamoyl]methyl}acetylamino)ethoxy]ethane (compound 8-6)

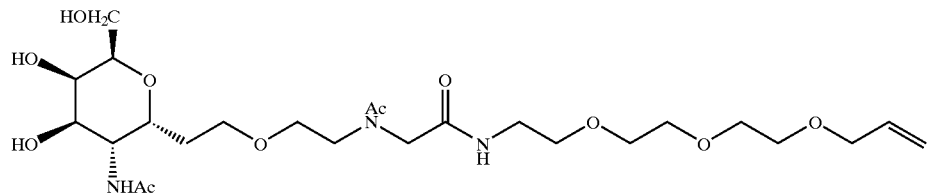

A mixture of the acetate compound (19.5 mg, 29.0 μmol) obtained from the above mentioned Example 31 and sodium methoxide (3 mg, 58.0 μmol) in methanol (1 ml) was stirred for 1.5 h at 0° C. The reaction mixture was neutralized by IR-120, filtered and the filtrate was removed under reduced pressure. 15.7 mg (99%) of the objective compound was obtained as a colorless oil.

MS (ESI, m/e): 562 (M⁺).

IR (cm⁻¹) neat: 3272, 2932, 1636.

¹H-NMR (CD₃OD) δ: 1.68–1.78 (1H, m), 1.92–2.00 (1H, m), 1.92 (3H, s), 2.21 (3H, s), 3.64–3.78 (24H, m), 3.83–3.88 (1H, m), 4.05–4.10 (2H, m), 4.21–4.29 (2H, m), 5.19–5.22 (1H, m), 5.30–5.53 (1H, m), 5.91–6.01 (1H, m).

Example 33

The preparation of the following compound.

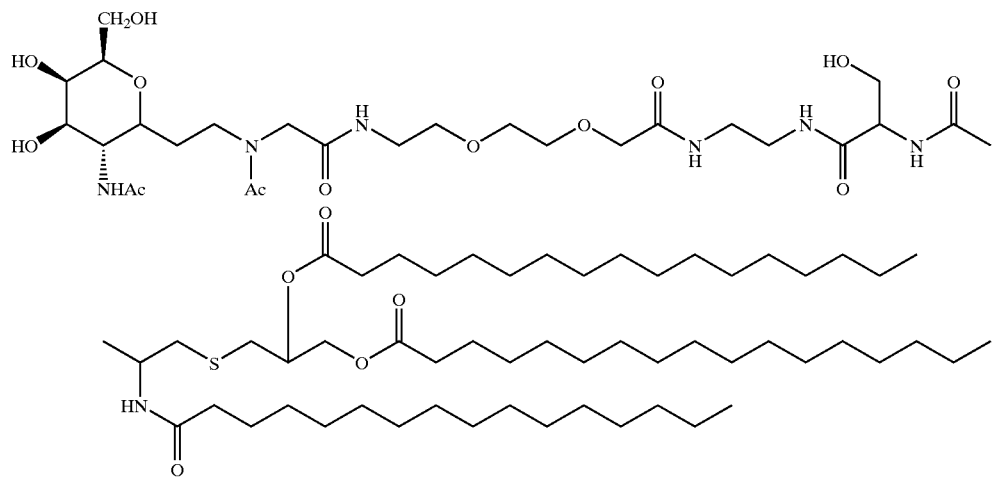

To a solution of the carboxylic acid (20 mg, 57.5 μmol) obtained from the above mentioned Example 7 and amine (136 mg, 115 μmol) in dimethylformamide (1 ml) was added diisopropylethylamine (42 μl, 230 μmol), HATU (87 mg, 230 μmol) and HOAt (16 mg, 115 μmol). After the mixture was stirred for 24 h, the mixture was poured into brine and extracted with chloroform, the organic layer was washed with 10% HCl and satd. NaHCO$_3$. After drying (Na$_2$SO$_4$), the solvent was removed under reduced pressure and the resulting residue was purified by silicagel column chromatography (CHCl$_3$:MeOH:AcOH=18:2:1). 5 mg (6%) of the objective compound was obtained as a colorless oil.

MS (ESI, m/e): 1150.

$^1$H-NMR (CDCl$_3$, ppm): δ1.70–2.12 (45H, m), 3.41–3.79 (15H, m), 4.09–4.58 (26H, m), 5.08–5.36 (1H, m), 5.40–5.48 (3H, m), 5.90–6.05 (1H, m).

Example 34

The preparation of the following compound.

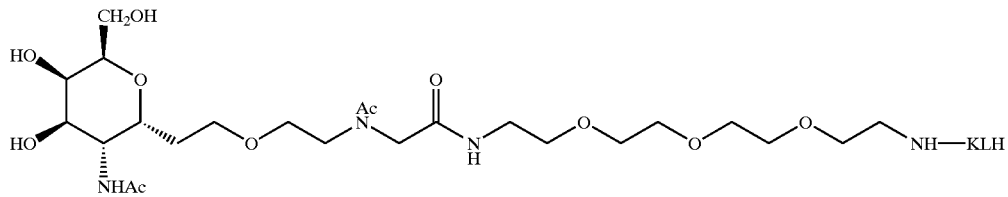

A solution of the compound obtained from the above mentioned Example 32 in methanol and dichlorometane was ozonized at −78° C. The reaction mixture was treated with dimethylsulfide and concentrated to obtain the aldehyde. To the mixture of this aldehyde and KLH in phosphate buffer was added sodium cyanoborohydride and stirred for 30 h. After purified by dialysis using PBS(-), the objective glycoprotein antigen was obtained.

Example 35

The preparation of the following compound.

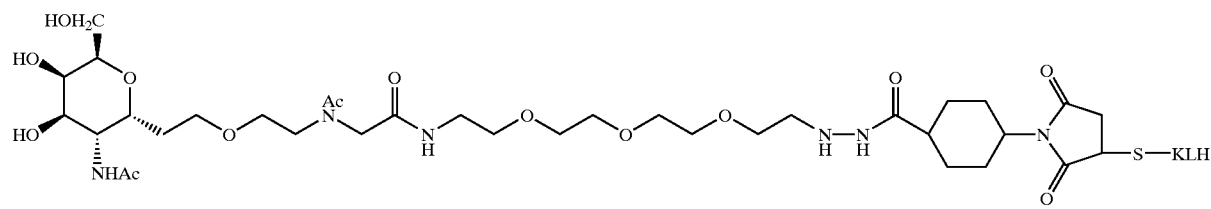

The aldehyde obtained from the above mentioned Example 34 reacted with 4-(4-N-maleimidomethyl)cyclohexyl-1-carbonylhydrzine to obtin a maleimide derivative. To the mixture of this compound and KLH in phosphate buffer was added sodium cyanoborohydride. After purified by dialysis using PBS(-), the objective glycoprotein antigen was obtained.

Example 36

The preparation of 2-(2-acetylamino-3,4,6-tri-O-acetyl-2-deoxy-α-D-galactopyrano-1-yl)-1-[2-(N-{[N-(2-{2-[2-(3-acetylthiopropoxy)ethoxy]ethoxy}ethyl)carbamoyl]methyl}acetylamino)ethoxy]ethane

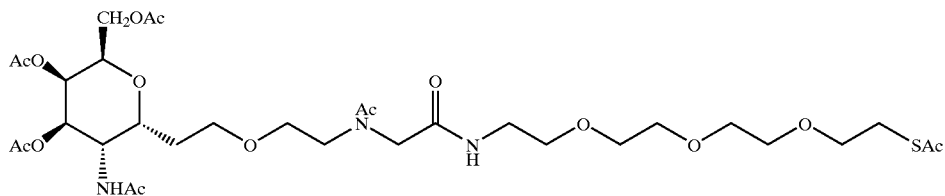

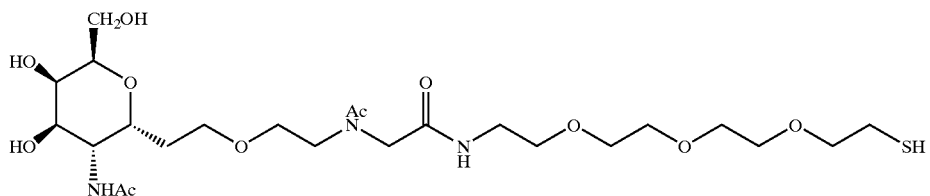

To a solution of the compound (20 mg, 0.029 mmol) obtained from the above mentioned Example 36 in methanol (1 ml) was added sodium methoxide (2 mg, 0.058 mmol) and stirred for 12 h. The reaction mixture neutralized by IR-120, filtered using celite, and the solvent was removed under reduced pressure. 8 mg (51%) of the objective compound was obtained.

Example 38

The preparation of the following compound.

To a solution of the olefine (22 mg, 0.032 mmol) obtained from the above mentioned Example 31 in dioxane (2 ml) was added thioacetic acid (0.02 ml) and the mixture was heated at 80° C. for 6 h. The solvent was removed under reduced pressure. The redsidue was purified by silicagel column chromatography (AcOEt:MeOH=9:1). 0.02 g (82%) of the objective compound was obtained.

Example 37

The preparation of 2-(2-acetylamino-2-deoxy-α-D-galactopyrano-1-yl)-1-[2-(N-{[N-(2-{2-[2-(3-sulfenylpropoxy)ethoxy]ethoxy}ethyl)carbamoyl]methyl}acetylamino)ethoxy]ethane

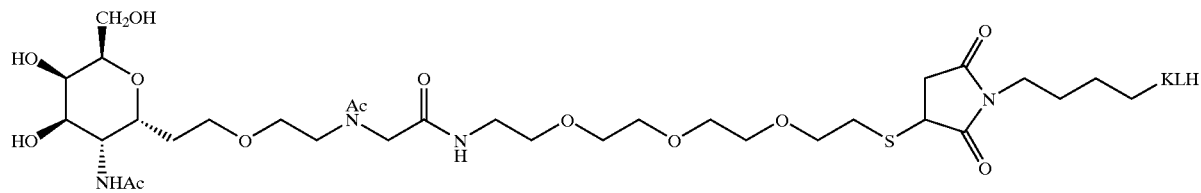

The compound obtained from the above mentioned Example 37 was added to maleimidated KLH with stirring and allowed to stand over 2 h at 4° C. The reaction mixture was dialyzed with phosphate buffered saline (pH7.4) for 48 h and with distilled water for 48 h, followed by byophilization and obtained the objective compound.

What is claimed is:

1. A compound of the general formula (1),

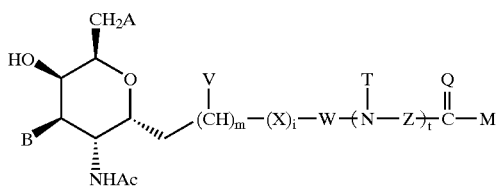

(1)

wherein
A represents OH or sialic acid;
B represents OH or galactose;
T represents H or protecting groups of amine;
M represents H or OH;
X represents oxygen atom, —NH— or $S(O)_z$ where z is 0, 1 or 2;
Q is oxygen atom and can be present or not present;
V represents lower alkyl or H;
W is straight or branched alkylene groups from 0 to 5;
Z is straight or branched alkylene groups from 1 to 5; and
i, m, and t is 0 or 1 with the proviso that i and t cannot be both 0.

2. A compound of the general formula (2),

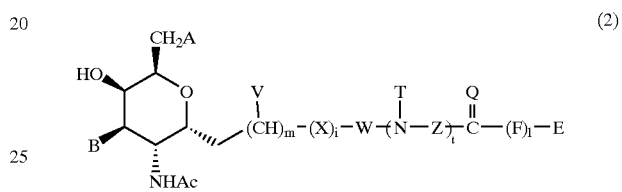

(2)

wherein

A represents OH or sialic acid, and

B represents OH or galactose;

T represents H or protecting groups of amine;

X represents oxygen atom, —NH— or $S(O)_z$ where z is 0, 1 or 2;

Q is oxygen atom and can be present or not present;

V represents lower alkyl or H;

W is straight or branched alkylene groups from 0 to 5;

Z is straight or branched alkylene groups from 1 to 5;

i, m, and t is 0 or 1 with the proviso that i and t cannot be both 0;

E represents pharmaceutically acceptable carrier compounds;

l is 0 or 1;

F is showed followings,

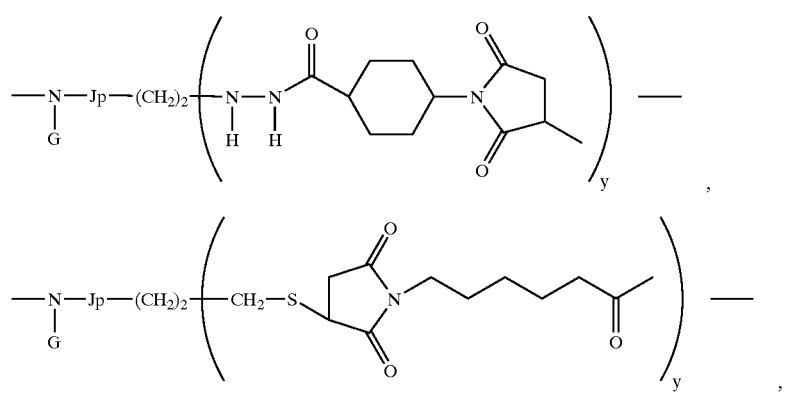

$$-N-Jp-(CH_2)_2-\left(\begin{matrix}N\\|\\H\end{matrix}\right)_y , \quad -N-Jp-(CH_2)_2-\left(\begin{matrix}C\\||\\O\end{matrix}\right)_y \quad \text{and} \quad -N-Jp-\left(CH_2-\begin{matrix}C\\||\\O\end{matrix}\right)_y$$

wherein

J is —CH$_2$CH$_2$X— or —N(L)-CH$_2$CO— where X represents oxygen atom, —NH— or S(O)$_z$ where z is 0, 1 or 2;

L is H or lower alkyl;

G is H or lower alkyl;

p is 0 to 3; and y is 0 or 1.

3. A compound of the general formula (3),

V represents lower alkyl or H;

W is straight or branched alkylene groups from 0 to 5;

Z is straight or branched alkylene groups from 1 to 5;

i, m, and t is 0 or 1;

E represents pharmaceutically acceptable carrier compounds;

l is 0 or 1; and r is from 1 to 4.

4. A compound of the general formula (4), (3)

[Chemical structure of formula (3)]

wherein

A represents OH or sialic acid, and

B represents OH or galactose;

T represents H or protecting groups of amine;

X represents oxygen atom, —NH— or S(O)$_z$ where z is 0, 1 or 2;

Q is oxygen atom and can be present or not present;

(4)

[Chemical structure of formula (4)]

wherein

A represents OH or sialic acid, and

B represents OH or galactose;

T represents H or protecting groups of amine;

X represents oxygen atom, —NH— or $S(O)_z$ where z is 0, 1 or 2;

Q is oxygen atom and can be present or not present;

V represents lower alkyl or H;

W is straight or branched alkylene groups from 0 to 5;

Z is straight or branched alkylene groups from 1 to 5;

J is —$CH_2CH_2X$— or —$N(L)$-$CH_2CO$— where X represents oxygen atom, —NH— or $S(O)_z$ where z is 0, 1 or 2;

i, m, and t is 0 or 1;

p is 0 to 3;

r is from 1 to 4;

U represents H or lower alkyl;

w is 0 to 50; and y is 1 or 50.

5. The compound thereof of claim 1, wherein A is sialic acid and B is OH.

6. The compound thereof of claim 2, wherein A is sialic acid and B is OH.

7. The compound thereof of claim 3, wherein A is sialic acid and B is OH.

8. The compound thereof of claim 4, wherein A is sialic acid and B is OH.

9. The compound thereof of claim 1, wherein A is OH and B is galactose.

10. The compound thereof of claim 2, wherein A is OH and B is galactose.

11. The compound thereof of claim 3, wherein A is OH and B is galactose.

12. The compound thereof of claim 4, wherein A is OH and B is galactose.

13. The compound thereof of claim 1, wherein both A and B are OH.

14. The compound thereof of claim 2, wherein both A and B are OH.

15. The compound thereof of claim 3, wherein both A and B are OH.

16. The compound thereof of claim 4, wherein both A and B are OH.

* * * * *